United States Patent
Loosmore et al.

(10) Patent No.: US 7,785,609 B1
(45) Date of Patent: Aug. 31, 2010

(54) **RECOMBINANT *HAEMOPHILUS INFLUENZAE* ADHESIN PROTEINS**

(75) Inventors: Sheena M. Loosmore, Aurora (CA); Yan-Ping Yang, Toronto (CA); Michel H. Klein, Toronto (CA)

(73) Assignee: Sanofi Pasteur Limited, Toronto, Ontario (CA)

( * ) Notice: Subject to any disclaimer, the term of this patent is extended or adjusted under 35 U.S.C. 154(b) by 0 days.

(21) Appl. No.: 09/936,362

(22) PCT Filed: Mar. 16, 2000

(86) PCT No.: PCT/CA00/00289

§ 371 (c)(1),
(2), (4) Date: Dec. 19, 2001

(87) PCT Pub. No.: WO00/55191

PCT Pub. Date: Sep. 21, 2000

Related U.S. Application Data

(63) Continuation-in-part of application No. 09/268,347, filed on Mar. 16, 1999, now Pat. No. 6,335,182.

(51) Int. Cl.
*A61K 39/102* (2006.01)

(52) U.S. Cl. .............. 424/256.1; 424/185.1; 424/190.1; 530/350

(58) Field of Classification Search ................ 435/69.1, 435/69.3, 71.1, 320; 530/350; 424/256.1, 424/185.1, 190.1; 536/23.7
See application file for complete search history.

(56) References Cited

U.S. PATENT DOCUMENTS

| | | | |
|---|---|---|---|
| 4,258,029 A | 3/1981 | Moloney | 424/88 |
| 4,496,538 A | 1/1985 | Gordon | 424/92 |
| 4,855,283 A | 8/1989 | Lockhoff | 424/27.8 |
| 4,952,496 A | 8/1990 | Studier | 435/91 |
| 5,194,254 A | 3/1993 | Barber | 424/85.8 |
| 5,549,897 A | 8/1996 | Barenkamp et al. | |
| 5,603,938 A | 2/1997 | Barenkamp et al. | |
| 5,646,259 A | 7/1997 | St. Geme, III | 536/23.1 |
| 5,808,024 A | 9/1998 | Sasaki et al. | 536/23.1 |
| 5,843,463 A | 12/1998 | Krivan | 424/256.1 |
| 5,869,065 A | 2/1999 | Barenkamp et al. | |
| 5,869,302 A | 2/1999 | Loosmore et al. | |
| 5,925,362 A | 7/1999 | Spitler et al. | |
| 6,153,406 A | 11/2000 | Tai et al. | |
| 6,218,141 B1 | 4/2001 | Barenkamp et al. | |
| 6,342,232 B1 | 1/2002 | Loosmore et al. | |
| 6,432,669 B1 | 8/2002 | Loosmore et al. | |
| 6,974,581 B1 | 12/2005 | Loosmore et al. | |
| 7,118,749 B2 | 10/2006 | Loosmore et al. | |

FOREIGN PATENT DOCUMENTS

| | | |
|---|---|---|
| EP | 1903055 A3 | 8/2008 |
| EP | 09170138.3 | 2/2010 |
| EP | 2133359 A3 | 3/2010 |
| WO | WO 95/34308 | 12/1995 |
| WO | WO 96/02648 | 2/1996 |
| WO | WO 96/30519 | 10/1996 |
| WO | WO 00135477 A3 | 6/2000 |
| WO | WO 00/51633 A3 | 9/2000 |

OTHER PUBLICATIONS

Berkowitz et al. 1987. J. Pediatr. 110:509.
Claesson et al. 1989. J. Pediatr. 114:97.
Black, S.B., H.R. Shinefield, B. Fireman, R. Hiatt, M. Polen, E. Vittinghoff, The Northern California Kaiser Permanent Vaccine Study Center Pediatrics Group. Efficacy in infancy of oligosaccharide conjugate *Haemophilus influenzae* type b (HbOC) vaccine in a United States population of 61,080 children. 1991. Pediatr. Infect. Dis. J. 10:97-104.
Madore, D.V. 1996. Impact of immunization on *Haemophilus influenzae* type b disease. Infectious Agents and Disease 5:8-20.
Bluestone, C.D. 1982. Current concepts in otolaryngology. Otitis media in children: to treat or not to treat? N. Engl. J. Med. 306:1399-1404.
St. Geme, J.W. and D. Cutter. (1995) Evidence that surface fibrils expressed by *Haemphilus influenzae* type B promote attachment to human epithelial cells. Molec. Microbiol. 15:77-85.
Barenkamp, S.J., and E. Leininger. 1992. Cloning, expression, and DNA sequence analysis of genes encoding nontypeable *Haemophilus influenzae* high-molecular-weight surface-exposed proteins related to filamentous hemagglutinin of *Bordetella pertussis*. Infect. Immun. 60:1302-1313.
Barenkamp, S.J. and J.W. St. Geme. (1996) Identification of a second family of high-molecular-weight adhesion proteins expressed by non-typable *Haemophilus influenzae*. Molec. Microbiol. 19:1215-1223.
St. Geme, J.W. D. Cutter, and S.J. Barenkamp.(1996) Characterization of the genetic locus encoding *Haemophilus influenzae* type b surface fibrils. J. Bact. 178:6281-6287.
St. Geme III, J.W., S. Falkow, and S.J. Barenkamp. 1993. High-molecular-weight proteins of nontypeable *Haemophilus influenzae* mediate attachment to human epithelial cells. Proc. Natl. Acad. Sci. USA 90:2875-2879.
Barenkamp, S.J. 1996. Immunization with high-molecular-weight adhesion proteins of nontypeable *Haemophilus influenzae* modifies experimental otitis media in chinchillas. Infect. Immun. 64:1246-1251.
Tabor, S., and C.C. Richardson. 1985. A bacteriophage T7 RNA polymerase/promoter system for controlled exclusive expression of specific genes. Proc. Natl. Acad. Sci. USA 82:1074-1078.
Patient, M.E., and D.K. Summers. 1993. ColE1 multimer formation triggers inhibition of *Escherichia coli* cell division. Molec. Microbiol. 9:1089-1095.
Yang, Y.-P., S.M. Loosmore, B. Underdown, and M.H. Klein. 1998. Nasopharyngeal colonization with nontypeable *H. influenzae* in chinchillas. Infect. Immun. 66:1973-1980.

(Continued)

*Primary Examiner*—Jennifer E Graser
(74) *Attorney, Agent, or Firm*—Patrick J. Halloran

(57) ABSTRACT

Recombinant production of Hia protein, in full-length and N-terminally truncated forms, of non-typeable strains of *Haemophilus influenzae*, is described. The nucleic acid and deduced amino acid sequences of Hia genes of various strains of non-typeable and type c *Haemophilus influenzae* also are described.

18 Claims, 204 Drawing Sheets

OTHER PUBLICATIONS

O'Hagan, DT. 1992. Oral delivery of vaccines. Formulation and clinical pharmaco kinetic considerations. Clin. Pharmacokinet 22(t): 1-10.

Ulmer et al. 1993. Curr. Opinion Invest. Drugs 2:983-989.

Lockhoff, O., 1991. Glycolipids as immunomodulators: Synthesis and properties.

Nixon-George A., et al., 1990. The adjuvant effect of stearyl tyrosine on a recombinant subunit hepatitis B surface antigen. J. Immunol 144 (12):4798-4802.

Laemmli, U.K. 1970. Cleavage of structural proteins during the assembly of the head of bacteriophage T4. Nature 227:680-685.

Babour, M.L. et al., The impact of conjugate vaccine on carriage of *Haemophilus influenzae* C type B. J. Infect. Dis. 171:93-98.

Nitta, D.M. et al. Pediatr. Infect. Dis. J. 14:157-160.

Waggoner-Fountain, L.A., et al., Clin. Infect. Dis. 21:1322-1324.

Loosmore, S.M. (1997) Infect. Immun. 65: 3701-3707.

Needleman, S.B. and Wunsch, C.D. 1970, J. Mol. Biol. 48:443-453.

Sellers, P.H. (1974) On the theory and computation of evolutionary distances. J. Appl. Math(Siam) 26:787-793.

Waterman, M.S. et al., (1976) Advan. Math. 20: 367-387.

Smith, T.F. and Waterman, M.S. (1981) Indentification of common molecular subsequences. J. Mol. Biol. 147:195-197.

Sobel, E. and Martinez, H.M. (1985) A Multiple Sequence Alignment Program. Nucleic Acid Res. 14:363-374.

St. Geme III W. et al., Infection and Immunity, US, American Society for microbiology. (1998) vol. 66, No. 1 pp. 364-368. XP002137980.

Bernardfz Clark, et al. Refolding of recombinant proteins. Curr. Op. Biotech. 9:157-63(1998).

Loosmore, et al, The Haemophilus influenzae HtrA protein is a protective antigen. Inf, Immun, 66(3): 899-906 (1998).

Yang, et al. A 20-kilodaltron N-terminal fragment of the D15 protein contains a protective epitope(s) against Haemophilus influenzae type a and type b. Inf. Immun. 66(7): 3349-3354 (1998).

Restriction map of DS-2008-2-3, pT7 hia (11).

pT7 hia (11)

Oligonucleotides used to PCR amplify the full-length strain 11 hia gene for expression studies.

FIG.4

Sites for N-terminal truncations of rHia proteins.

MNKIFNVIWNVVTQTWVVVSE$^{21}$LTRTHTKCASAT$^{33}$VAVAV$^{38}$LATLLSATVEANAN$^{52}$TPVINKLKAYGD (SEQ ID NO.6)

Construction of plasmids expressing truncated hia (11) genes.

FIG.5B

Oligonucleotide primers to PCR amplify truncated strain 11 *hia* genes.

E21

EcoR I Nde I

| | | | | |
|---|---|---|---|---|
| | M E L T R T H T K C A | | | SEQ ID NO: 8 |
| 5′ | GGGAATTCATATGGAACTCACTCGCACCCACACCAAATGGGCC | 3′ | 5524.SL | SEQ ID NO: 7 |

T33

| | | | | |
|---|---|---|---|---|
| | M T V A V A V L A T L | | | SEQ ID NO:10 |
| 5′ | GGGAATTCATATGACCGTGGCGGTTGCCGTATTGGCAACCCTG | 3′ | 5525.SL | SEQ ID NO: 9 |

V38

| | | | | |
|---|---|---|---|---|
| | M V L A T L L S A T | | | SEQ ID NO:12 |
| 5′ | GGGAATTCATATGGTATTGGCAACCCTGTTGTCCGCAACG | 3′ | 5526.SL | SEQ ID NO:11 |

FIG.5B'

N52
```
            M  N  T  P  V  T  N  K  L  K  A
5' GGGAATTCATATGAATACTCCTGTTACGAATAAGTTGAAGGCT 3'    5527.SL    SEQ ID NO:14
                                                                SEQ ID NO:13
``` antisense
```
      H  T  I  T  F  A  L  A  K  D  L  G
5' CACACCATTACTTTCGCTAGCGAAAGACCTTGGTTG        3'
3' GTGTGGTAATGAAACGGATCGCTTTCTGGAACCACCTAGGGC  5'    5528.SL    SEQ ID NO:17
                    ↑        ↑          ↑                      SEQ ID NO:16
                  Nhe I    Sty I     BamH I                    SEQ ID NO:15
```

Oligonucleotides used to generate the multiple cloning site and transcription terminators for the expression plasmids

FIG. 7B

Oligonucleotides used to generate the 5'-end of the strain 33 hia gene for expression studies.

```
Nde I
    M  N  K  I  F  N  V  I  W  N  V  M  T  Q  T  W  A  V  V  S  E  L  T  R  A  H  T  K...
    TATGAACAAAATTTTTAAGGTTATTTGGAATGTTATGACTCAAACTTGGGCTGTCG
                                                            TATCTGAACTCACTCGCGCCCACACCA...
    ACTTGTTTTAAAAATTGCAATAAACCTTACAATACTGAGTTT
                                              GAACCCGACAGCATAGACTTGAGTGAGCGCGGGTGTGGT...
                                                                                     ...

...  R  A  S  A  T  V  A  A         SEQ ID NO:54
                                                ...AAGTGCTCCGCAACGTGGCAGCCG          SEQ ID NO:52
                                                ...TTGCACGGAGGGTTGGCACGTC            SEQ ID NO:53
                                                                         ↑
                                                                       AlwN I
                                                ...
```

FIG. 8B

Oligonucleotides used to PCR amplify the strain 33 hia gene from the V38 codon to the SnaB I site.

sense

```
         Nde I
       ↓ M  V  L  A  T  V  L  S  A  T
5' GGGAATTCATATGGTATTGGCGACGGTATTGTCTGCAACG 3'    6286.SL    SEQ ID NO:61
                                                             SEQ ID NO:60
``` antisense

```
                       SnaB I
                         ↓
     D  E  T  T  A  T  V  G  N  L  R  K  L
5' GACGAAACCACCGCAACGTAGCCAATTAGTAAATTGAAGCTTCG 3'             SEQ ID NO:20
3' CTGCTTTGGTGGCGTTGCATCGGTTAATCATTTAACTTCGAAGC 5'   6287.SL   SEQ ID NO:19
                                                               SEQ ID NO:18
```

1. Prestained molecular weight markers
2. E. coli whole cell lysate
3. Crude extract
4. Purified rHia protein Anti-V38 rHia (SB11) Antibody Titers in Guinea Pigs ☐ 25 ug
▨ 50 ug
▧ 100 ug

Oligonucleotides used to PCR amplify additional hia genes.

sense

```
         M  N  K  I  F  N  V
5'  TTAAATATATAAGGTAAATAAAATGAACAAAATTTTTAACGTT  3'   5040.SL   SEQ ID NO:22
                                                                SEQ ID NO:21
``` antisense

```
         K  T  G  V  A  A  A  G  V  G  Y  Q  W  *
5'  AAAACAGGGGTTGCAGCAGGTGTTGGTTACCAGTGGTAATAG                                3'              SEQ ID NO:5
3'  TTTTGTCCCAACGTCGTCCACAACCAATGGTCACCATTATCTTAAGGCCTAGGCG  5'   5039.SL     SEQ ID NO:4
                                            ↑        ↑                        SEQ ID NO:3
                                         EcoR I    BamH I
```

FIG.18A NTHi strain 33 Hia

```
                              MET ASN LYS...       ILE PHE ASN VAL ILE TRP ASN VAL MET THR GLN
G A A T T C G G C T T A A A T A A A A A T G A A C A A . . . A A T T T T T A A C G T T A T T T G G A A T G T T A T G A C T T C A
                        10                    20                  30                40               50                60

THR TRP ALA VAL VAL SER GLU LEU THR...     ARG ALA HIS THR LYS ARG ALA SER ALA THR VAL
A A C T T G G G G C T G T C G T A T C T G A A C T C A C . . . T C G C G C C C A C C A C C A A A C G T G C C C T C C G C A A C C G T
              70                  80                    90                100             110                    120

ALA ALA VAL LEU ALA THR...     SER ALA THR VAL GLN ALA SER ALA GLY SER THR
G G C A G C C G C T G T A T T G G G C G A C C G T A T T . . . G T C T G C A A C G G T T C A G G C G A G T G C A G G C A G T A C
                130                     140                           150             160                    170             180

THR GLY THR ASN SER LEU ASN VAL TYR...
G A C A G G T A C A A A T A G T T T G A A T G T T T A
              190                    200
```

FIG.18B

```
                                 GLY LYS ASN ASN SER ASN PHE ASN SER ALA ASN
                              ...T G G A A A G A A T A A T T C G A A T T T C A A T T C A G C C A A
                                 ...           210           220           230           240

ASN SER ILE ALA ASP LEU ASN LYS GLN...        ASN ASP SER VAL TYR ASP GLY LEU LEU ASN LEU
T A A T T C A A T A G C A G A T T T A A A T A A A C A ...   ...A A A T G A T A G T G T T T A C G A T G G T T T A T T A A A T C T
          250                260                       270           280           290           300

ASN GLU LYS GLY THR ASP LYS SER LYS...              PHE LEU VAL ALA ASP GLU THR ALA THR VAL
G A A T G A A A A A G G T A C G G A T A A G T C A A A ...   ...A T T C C T G G T T G C T G A C G A A A C C A C C G T
          310              320                         330           340           350           360

GLY ASN LEU ARG LYS LEU GLY TRP VAL...              VAL SER THR LYS ASN SER THR LYS GLU GLU SER
A G G C A A T T T A C G T A A A T T G G G T T G G G T ...   ...A G T A T C A A C C A A A A A C A G T A C G A A A G A A A G
          370              380                         390           400           410           420
```

FIG.18C

```
ASN GLN VAL LYS GLN ALA ASP GLU VAL...
CAATCAAGTCAAACAGGCGGATGAAGT...
            430                440
                                    ...LEU PHE GLU GLY LYS ASP GLY VAL THR VAL THR
                                    ...GTTGTTTGAAGGCAAAGACGGTGTAACGGTTAC
                                       ...   450               460               470             480

SER LYS SER GLU ASN GLY LYS HIS THR...
TTCCAAATCTGAAAACGGCAAACACAC...
            490                500
                                    ...VAL THR PHE ALA LEU ALA ASN ASP LEU ASN VAL
                                    ...CGTTACTTTTGCCCCTTGCGAATGACCTTAATGT
                                       ...   510               520               530             540

LYS ASN ALA THR VAL SER ASP LYS LEU...
AAAAACGCAACCGTTAGCGATAAATT...
            550                560
                                    ...SER LEU GLY ALA ASN GLY LYS LYS VAL ASP ILE
                                    ...ATCGCTTGGTGCAAACGGCAAAGAAAGTCGATAT
                                       ...   570               580               590             600

THR SER ASP ALA ASN GLY LEU LYS PHE...
TACCAGTGATGCAAACGGCTTGAAATT...
            610                620
```

FIG. 18D

```
                    ALA LYS GLN GLY THR ASN GLY GLN ASN GLY ASN
                ...TGCGAAACAGGGGTACGAATGGTCAAAACGGTAA
                ...                 640           650          660
                                630

VAL HIS LEU ASN GLY ILE ALA SER THR...         LEU ASP ASP PRO ARG VAL GLY LYS THR ALA
TGTTCACTTAAACGGTATTGCTTCGAC...             ...TTTAGATGATCCTCGTGTGGGTGGAAAACAGC
                670           680                          700           710          720
                                                690

HIS LEU THR LYS GLU ILE SER ASP THR...          GLU ARG ASN ARG ALA ALA SER VAL GLY ASP VAL
ACACCTTACAAAAGAAATCAGCGATAC...              ...AGAACGTAACCGTGCTGCGAGCGTGGGCGATGT
                730           740                          760           770          780
                                750

LEU ASN ALA GLY TRP ASN ILE ARG GLY...          ALA LYS THR ILE GLY GLY THR VAL ASP ASN VAL
ATTGAATGCGGGTTGGAATATTCGTGG...              ...CGCAAAAACGATTGGCGGTACAGTGGATAATGT
                790           800                          820           830          840
                                810
```

FIG.18E

```
ASP PHE VAL SER THR TYR ASP THR VAL...   GLU PHE ALA SER GLY ALA ASN ALA ASN VAL SER
TGATTTTGTTTCAACTTATGACACTGT...      ...TGAATTTGCCAGCGGCGCAAACGCAAATGTGAG
              850                            870           880           890           900

VAL THR THR ASP ASP ASN LYS LYS THR...   THR VAL ARG VAL ASP VAL THR GLY LEU PRO VAL
CGTTACGACTGATGATAACAAAAAAC...       ...AACCGTCCGTGTGGATGTAACAGGCTTGCCGGT
              910           920                     930           940           950           960

GLN TYR VAL THR GLU ASP SER LYS THR...   VAL VAL LYS VAL GLY ASN GLU TYR TYR GLU ALA
CCAATATGTTACGGAAGACAGCAAAAAC...     ...CGTTGTGAAAGTGGGCAATGAGTATTACGAAGC
              970           980                     990           1000          1010          1020

LYS GLN ASP GLY SER ALA ASP MET ASP...
CAAGCAAAGACGGTTCGGCGGATATGGA...
              1030          1040
```

FIG.18F

```
                      LYS  LYS  VAL  GLU  ASN  GLY  LYS  LEU  ALA  LYS  THR
                   ...TAAAAAGTCGAAAATGGCAAGCTGGCGAAAAC
                                    1050                1060                1070                1080

LYS  VAL  LYS  LEU  VAL  SER  ALA  ASN  GLY...           THR  ASN  PRO  VAL  LYS  ILE  SER  ASN  VAL  ALA  ASP
TAAAGTGAAATTGGTATCGGCAAACGG...        ...TACAAATCCGGTGAAAATCAGCAATGTTGCGGA
             1090                1100                              1110                1120                1130                1140

GLY  THR  GLU  ASP  THR  ASP  ALA  VAL  SER...           PHE  LYS  GLN  LEU  LYS  ALA  LEU  GLN  ASP  LYS  GLN
CGGCACGGAAGATACCGATGCGGTCAG...        ...CTTTAAGCAGTTGAAAGCCTTGCAAGATAAACA
             1150                1160                              1170                1180                1190                1200

VAL  THR  LEU  SER  ALA  ASN  ALA  TYR...                ALA  ASN  GLY  GLY  SER  ASP  ALA  ASP  GLY  GLY  LYS
GGTTACGTTAAGTGCCGAGCAATGCTTA...       ...TGCCAATGGCGGTAGCGATGCCGACGGCGCAA
             1210                1220                              1230                1240                1250                1260
```

FIG.18G

```
ALA   THR   GLN   THR   LEU   GLY   ASN   ASP   LEU...       ASN   PHE   LYS   PHE   LYS   SER   THR   ASP   SER   GLU   LEU
GGCAACTCAAACTTTAGGCAATGATTT...              ...GAATTTTAAATTTAAATCCACAGACAGCGAGTT
              1270              1280           ...1290          1300              1310              1320

LEU   ASN   ILE   LYS   ALA   ALA   GLY   ASP   THR...       VAL   THR   PHE   THR   PRO   LYS   LYS   GLY   SER   VAL   GLN
GTTGAACATCAAAGCAGCAGGTGACAC...              ...GGTTACCTTTACGCCGAAAAAGGTTCGGTGCA
              1330              1340           ...1350          1360              1370              1380

VAL   GLY   ASP   ASP   GLY   LYS   ALA   THR   ILE...       GLN   ASP   GLY   ALA   LYS   THR   THR   THR   GLY   LEU   VAL
GGTTGGCGATGATGGCTAAGGCTACGAT...             ...TCAAGACGGCGCGAAAACAACTACCGGTTTGGT
              1390              1400           ...1410          1420              1430              1440

GLU   ALA   SER   GLU   LEU   VAL   ASP   SER   LEU...
TGAGGCTTCTGAATTGGTTGACAGCCT...
              1450              1460
```

FIG. 18H

```
                                    ASN LYS LEU GLY TRP LYS VAL GLY VAL GLY LYS
                                ...G A A C A A A T T G G G C T G G A A A G T G G G C G T T G G T A A
                                ...1470         1480              1490             1500

ASP GLY THR GLY ALA THR ASP GLY THR...       HIS THR ASP THR LEU VAL LYS SER GLY ASP LYS
A G A C G G C A C A G G A G C G A C C G A T G G C A C...G C A T A C C G A C A C T T T A G T G A A G T C G G G C G A T A A
         1510                   1520                     1530             1540             1550             1560

VAL THR LEU LYS ALA GLY ASP ASN LEU...       LYS VAL LYS GLN GLU GLY THR ASN PHE THR TYR
A G T A A C T T T G A A A G C C C G G C G A T A A T C T...G A A G G T C A A A C A A G A G G G T A C A A A C T T C A C T T A
         1570                   1580                     1590             1600             1610             1620

VAL LEU ARG ASP GLU LEU THR GLY VAL...       LYS SER VAL GLU PHE LYS ASP THR GLU ASN GLY
C G T G C T T C A G A G A T G A A T T G A C G G G C G T...A A A G A G C G T G G A G T T T A A A G A C A C G G A G A A T G G
         1630                   1640                     1650             1660             1670             1680
```

FIG.18I

```
ALA ASN GLY ALA SER THR LYS ILE THR...                    LYS ASP GLY LEU THR ILE THR PRO ALA ASN ASP
TGCAAACGGTGCAAGCACGAAGATTAC....             ...CAAAGACGGCTTGACCATTACGCCCGGCAAACGA
           1690                 1700             ...1710                1720                1730                1740

ALA ASN GLY ALA ALA ALA THR ASP ALA...                    ASP LYS ILE LYS VAL ALA SER ASP GLY ILE SER
TGCGAATGGTGCGGCGGCGACTGATGC....              ...TGACAAGATTAAAGTGGCTTCAGACGGCATTAG
           1750                 1760             ...1770                1780                1790                1800

ALA GLY ASN LYS ALA VAL LYS ASN VAL...                    VAL SER GLY LEU LYS LYS PHE GLY ASP ALA ASN
TGCGGGTAATAAAGCAGTTAAAAACGT....              ...TGTGAGCGGACTGAAGAAATTTGGTGATGCCGAA
           1810                 1820             ...1830                1840                1850                1860

PHE ASN PRO LEU THR SER SER ALA ASP...
TTTCAATCCGCTGACTAGCTCAGCCGA....
           1870                 1880
```

FIG. 18J

```
                              ASN  LEU  THR  LYS  GLN  TYR  ASP  ASN  ALA  TYR  LYS
                           ...C A A C T T A A C G A A A C A A T A T G A C A A T G C C T A T A A
                           ...                1900                1910                1920

GLY  LEU  THR  ASN  LEU  ASP  GLU  LYS  SER...                  LYS  GLY  LYS  GLN  THR  PRO  THR  VAL  ALA  ASP  ASN
A G G C T T G A C C A A T C T G G A T G A A A A A A G ....   ...T A A A G G C A A G C A A A C T C C G A C C G T T G C T G A C A A
                1930                1940                                     1950                1960                1970                1980

THR  ALA  ALA  THR  VAL  GLY  ASP  LEU  ARG...                  GLY  LEU  GLY  TRP  VAL  ILE  SER  ALA  ASP  LYS  THR
T A C C G C T G C A A C C G T G T G G G C G A T T T G C G ...   ...C G G T T T G G G C T G G G T C A T T T C T G C A G A C A A A A C
                1990                2000                                     2010                2020                2030                2040

THR  GLY  GLU  SER  LYS  GLU  TYR  SER  ALA...                  GLN  VAL  ARG  ASN  ALA  ASN  GLU  VAL  LYS  PHE  LYS
C A C A G G C G A G T C A A A G G A A T A T A G C G C ....  ...G C A A G T G C C G T A A C G C C A A T G A A G T G A A A T T C A A
                2050                2060                                     2070                2080                2090                2100
```

FIG.18K

```
SER GLY ASN GLY ILE ASN VAL SER GLY...
GAGCGGGCAACGGTATCAATGTTTCCGG...
                      2110            2120
                                    ...TAAAACATTGGATAACGGTACGCGCGAAATTAC
                                       ...2130            2140            2150            2160
                                                    LYS THR LEU ASP ASN GLY THR ARG GLU ILE THR

PHE GLU LEU ALA LYS ASP GLU ASN ALA...
TTTTGAATTGGCTAAAGACGAAAATGC...
                      2170            2180
                                    ...CATTGCTTTCGGTTCTGGCTCAAAAGCCTTGCG
                                       ...2190            2200            2210            2220
                                                    ILE ALA PHE GLY SER GLY SER LYS ALA LEU ARG

ASP ASN THR VAL ALA ILE GLY THR GLY...
CGATAACACGGTGGCGATTGGTACGGGG...
                      2230            2240
                                    ...CAACGTTGTGAATGCGGAAAATCTGGTTGCATT
                                       ...2250            2260            2270            2280
                                                    ASN VAL VAL ASN ALA GLU LYS SER GLY ALA PHE

GLY ASP PRO ASN TYR ILE GLU ASP LYS...
CGGCGATCCGAACTACATCGAAGATAA...
                      2290            2300
```

FIG. 18L

```
                                              ALA GLY GLY SER TYR ALA PHE GLY ASN ASP ASN
                                           ...AGCCGGTGGCAGCTACGCTTTCGGTAACGATAA
                                           ...2310                              2330      2340
                                                                    2320

ARG ILE THR SER LYS ASN THR PHE VAL...            LEU GLY ASN GLY VAL ASN ALA LYS TYR LYS ALA
CCGTATTACTTCTAAAAACACTTTTGT...                 ...GTTGGGTAATGGAGTTAATGCGAAATATAAAGC
            2350                   2360        ...2370                              2390      2400
                                                                    2380

ASN GLY ASP VAL ASP THR GLU THR VAL...            THR VAL LYS ASP LYS ASP GLY LYS GLU THR THR
CAATGGAGATGTTGATACGGAAACCGT...                 ...AACTGTTAAGGACAAAGACGGTAAAGAGACTAC
            2410                   2420        ...2430                              2450      2460
                                                                    2440

VAL THR VAL PRO LYS ALA LEU GLY ALA...            THR VAL GLU ASN SER VAL TYR LEU GLY ASN LYS
CGTTACTGTTCCTAAAGCGTTAGGGGC...                 ...TACGGTTGAAAACTCCGTTTATTTGGGTAATAA
            2470                   2480        ...2490                              2510      2520
                                                                    2500
```

FIG.18M

```
SER THR ALA THR LYS ASP LYS GLY LYS...    ASN LEU LYS SER ASP GLY THR ALA GLY ASN THR
ATCGACTGCGACAAAAGATAAGGGTAA...           ...AAATCTGAAATCTGATGGTACGGGGGGTAACAC
         2530                  2540              2550            2560         2570         2580

THR THR ALA GLY THR THR GLY THR VAL...    ASN GLY PHE ALA GLY ALA THR ALA HIS GLY ALA
TACAAACTGCTGGTACAACGGGTACGGT...          ...AAACGGCTTTGCCGGTGCAACGGCGCACGGTGC
         2590                  2600              2610            2620         2630         2640

VAL SER VAL GLY ALA SER GLY GLU GLU...    ARG ARG ILE GLN ASN VAL ALA ALA GLY GLU ILE
GGTTTCTGTCGGGCGCAAGCGGGCGAAGA...         ...AAGACGTATCCAAAACGTTGCGGCCAGGCGAAAT
         2650                  2660              2670            2680         2690         2700

SER ALA THR SER THR ASP ALA ILE ASN...
TTCCGCTACTTCCACCGATGCGATTAA...
         2710                  2720
```

FIG.18N

```
                                    ... GLY SER GLN LEU TYR ALA VAL ALA LYS GLY VAL
                                    ...CGGCAGCCAGTTGTATGCCGTGGCAAAAGGGGT
                                    ...2730                              2750      2760

THR ASN LEU ALA GLY GLN VAL ASN LYS...
ACAAACCTTGCTGGACAAGTGAATAA...        ...VAL GLY LYS ARG ALA ASP ALA GLY THR ALA SER
              2770            2780   ...AGTGGGCAAACGTGCAGATGCAGGTACAGCAAG
                                     ...2790        2800            2810      2820

ALA LEU ALA ALA SER GLN LEU PRO GLN...
TGCATTAGCGGCTTCACAGTTACCACA...       ...ALA SER MET SER GLY LYS SER MET VAL SER ILE
                2830                 ...AGCCTCTATGTCAGGTAAATCAATGGTTTCTAT
                                     ...2840  2850            2860        2870      2880

ALA GLY SER SER TYR GLN GLN SER...
TGCGGGAAGTAGTTATCAAGGTCAAAG...       ...GLY LEU ALA ILE GLY VAL SER ARG ILE SER ASP
              2890            2900   ...TGGTTTAGCTATCGGGGTATCAAGAATTTCCGA
                                     ...2910              2920          2930      2940
```

FIG. 18O

```
ASN GLY LYS VAL ILE ILE ARG LEU SER...        ... GLY THR THR ASN SER GLN GLY LYS THR GLY VAL
TAATGGCAAAAGTGATTATTCGCTTGTC...      ...AGGCACAACCAATAGCCAAGGTAAAACAGGCGT
              2950              2960              ....2970            2980              2990              3000

ALA ALA GLY VAL GLY TYR GLN TRP ***                    ...ATAGAATTC
TGCAGCAGGTGTTGGTTACCAGTGGGTA...                         ....3030
              3010              3020
```

FIG.19A  NTHi strain 32 hia

```
GAATTCGGCTTTAAATATAAGGTAAATAAA...
         10        20        30 ....
                              MET ASN LYS ILE PHE ASN VAL ILE TRP ASN
                          ...AATGAACAAAATTTTTAACGTTATTTGGAA
                                  40        50        60

VAL VAL THR GLN THR TRP VAL VAL VAL SER...     GLU LEU THR ARG THR HIS THR LYS CYS ALA
TGTTGTGACTCAAACTTGGGTTGTCGTATC...          ...TGAACTCACTCGCACCCACCACCAAATGCGC
      70        80        90                      100       110       120

SER ALA THR VAL ALA VAL ALA VAL LEU ALA...     THR LEU LEU SER ALA THR VAL GLN ALA ASN
CTCCGCCACCGTGGCAGTTGCCGTATTGGC...          ...AACCCTGTTGTCCGCAACGGTTCAGGCGAA
     130       140       150                      160       170       180

ALA THR ASP GLU ASN GLU ASP ASP GLU GLU...
TGCTACCGATGAAAACGAAGATGATGAAGA...
     190       200       210
```

FIG.19B

```
                                    GLU  LEU  GLU  PRO  VAL  GLN  ARG  SER  VAL  LEU
                                 ...A G A G T T A G A A C C C G T A C A A C G C T C T G T T T T
                                  ...                              230                      240

ARG  TRP  SER  PHE  LYS  SER  ALA  LYS  GLU  GLY...
A A G G T G G A G C T T C A A A T C C G C T A A G G A A G G...
                       250                      260        270 ...

THR  GLY  GLU  GLN  GLU  GLY  THR  THR  GLU  VAL
                                 ...C A C T G G A G A A C A A G A G G G A A C A A C A G A G G T
                                  ...                              290                      300

ILE  ASN  LEU  ASN  THR  ASP  SER  SER  GLY  ASN...
A A T A A A T T T G A A C A C A G A T T C A T C A G G A A A...
                       310                      320        330 ...

ALA  VAL  GLY  SER  SER  THR  ILE  THR  PHE  LYS
                                 ...T G C A G T A G G A A G C A G C A C A A T C A C C T T C A A
                                  ...                              350                      360

ALA  GLY  ASP  ASN  LEU  LYS  ILE  LYS  GLN  SER...
A G C C G G C G A C A A C C T G A A A A T C A A A C A A A G...
                       370                      380        390 ...

GLY  ASN  ASP  PHE  THR  TYR  SER  LEU  LYS  LYS
                                 ...C G G C A A T G A C T T C A C C T A C T C G C T G A A A A A
                                  ...                              410                      420
```

FIG.19C

```
GLU LEU LYS ASN LEU THR SER VAL GLU THR...
AGAGCTGAAAAACCTGACCAGTGTTGAAAC...
          430                 440            450 ...
              ... GLU LYS LEU SER PHE GLY ALA ASN GLY ASN
              ...TGAAAAATTATCGTTTTGGCGCAAACGGCAA
                                 460                 470                 480

LYS VAL ASP ILE THR SER ASP ALA ASN GLY....
TAAAGTTGATATTACCAGTGATGCAAATGG....
         490                 500            510 ....
              ... LEU LYS LEU ALA LYS THR GLY ASN GLY ASN
              ...CTTGAAAATTGGCGAAAACAGGTAACGGAAA
                                 520                 530                 540

GLY GLN ASN SER ASN VAL HIS LEU THR LEU ASN GLY....
TGGTCAAAACAGTAATGTTCACTTAAACGG....
         550                 560            570 ....
              ... ILE ALA SER THR LEU THR ASP THR LEU ALA
              ...TATTGCTTCGACTTTGACCGATACGCTTGC
                                 580                 590                 600

GLY GLY THR THR GLY HIS VAL ASP THR ASN....
CGGTGGCACAACAGGACACGTTGACACCAA....
         610                 620            630 ....
```

FIG.19D

```
                            ILE ASP ALA VAL ASN TYR HIS ARG ALA ALA
                         ...CATTGATGCGGTTAATTATCATCGCGCTGC
                         ...                                  660
                            ...                           650
                         ...                                  640

SER VAL GLN ASP VAL LEU ASN SER GLY TRP...
AAGCGTACAAGATGTGTTAAACAGCGGTTG...
                                            690 ...
          670          680

ASN ILE GLN GLY ASN GLY ASN ASN VAL ASP
                         ..GAATATCCAAGGCAAATGGAAACAATGTCGA
                                                                720
                            ...                           710
                         ...                           700

PHE VAL ARG THR TYR ASP THR VAL ASP PHE...
TTTGTCCGTACTTACGACACCGTGGACTT...
                                            750 ...
          730          740

VAL ASN GLY ALA ASN ALA ASN VAL SER VAL
                         ..TGTCAATGGCGCGAATGCCAATGTGAGCGT
                                                                780
                            ...                           770
                         ...                           760

THR ALA ASP THR ALA HIS LYS THR THR...
TACGGGCTGATACGGCTCACAAAAAGACAAC...
                                            810 ...
          790          800

VAL ARG VAL ASP VAL THR GLY LEU PRO VAL
                         ..TGTCCGTGTGGATGTAACAGGCTTGCCCGGT
                                                                840
                            ...                           830
                         ...                           820
```

FIG.19E

GLN TYR VAL THR GLU ASP GLY LYS THR VAL...
TCAATATGTTACGGAAGACGGCAAAACCGT...
                850            870....
                    ...VAL LYS VAL GLY ASN GLU TYR TYR LYS ALA
                    ...TGTGAAAGTGGGCAATGAGTATTACAAAGC
                        860            880            900

LYS ASP ASP GLY SER ALA ASP MET ASN GLN...
CAAAGATGACGGGTTCGGCGGATATGAATCA...
                910            930....
                    ...LYS VAL GLU ASN GLY GLU LEU ALA LYS THR
                    ...AAAGTCGAAAACGGCGAGCTGGCGAAAAC
                        920            940            960

LYS VAL LYS LEU VAL SER ALA SER GLY THR...
CAAAGTGAAATTGGTATCGGCAAGCGGTAC...
                970            990....
                    ...ASN PRO VAL LYS ILE SER ASN VAL ALA ASP
                    ...AAATCCGGTGAAAATTAGCAATGTTGCAGA
                        980            1000            1020

GLY THR GLU ASP THR ASP ALA VAL SER PHE....
CGGCACGGAAGACACCGATGCGGTCAGCTT...
                1030            1050....
                    1040

FIG.19F

```
                         ... LYS GLN LEU LYS ALA LEU GLN ASP LYS GLN
                         ... T A A G C A A T T A A A A G C C T T G C A A G A C A A A A C A
                         ...                       1060             1070             1080

VAL THR LEU SER THR SER ASN ALA TYR ALA ...
G G T T A C G T T G A G C A C G A G C A A T G C T T A T G C ...
        1090             1100             1110    ...

ASN GLY GLY THR ASP ASN ASP GLY GLY LYS
         ... C A A T G G C G G T A C A G A T A A C G A C G G C G G C A A
                       1120             1130             1140

ALA THR GLN THR LEU SER ASN GLY LEU ASN ...
G G C A A C T C A A A C T T T A A G C A A T G G T T T G A A ...
        1150             1160             1170    ...

PHE LYS PHE LYS SER SER ASP GLY GLU LEU
         ... T T T T A A A T T T A A A T C T A G C G G A T G G C G A G T T
                       1180             1190             1200

LEU LYS ILE SER ALA THR GLY ASP THR VAL ...
G T T G A A A A A T T A G C C G C G A C C G G C G A T A C G G T ...
        1210             1220             1230    ...

THR PHE THR PRO LYS GLY SER VAL GLN
         ... T A C T T T T A C G C C G A A A A A G G T T C G G T A C A
                       1240             1250             1260
```

FIG.19G

VAL GLY ASP ASP GLY LYS ALA SER ILE SER...
GGTTGGCGATGATGGCAAGGCTTCAATTTC....
         1270              1280              1290 ...

LYS GLY ALA ASN THR THR GLU GLY LEU VAL
                   ...AAAAGGTGCAAATACAAACTGAAGGTTTGGT
                           1300              1310              1320

GLU ALA SER GLU LEU VAL GLU SER LEU ASN...
TGAGGCTTCTGAATTGGTTGAAAGCCCTGAA....
         1330              1340              1350 ...

LYS LEU GLY TRP LYS VAL GLY VAL GLU LYS
                   ...CAAACTGGGTTGGAAAGTAGGGGTTGAGAA
                           1360              1370              1380

VAL GLY SER GLY GLU LEU ASP GLY THR SER...
AGTCGGCAGCGGCGAGCTTGATGGTACATC....
         1390              1400              1410 ...

LYS GLU THR LEU VAL LYS SER GLY ASP LYS
                   ...CAAGGAAACTTTAGTGAAGTCGGGCGATAA
                           1420              1430              1440

VAL THR LEU LYS ALA GLY ASP ASN LEU LYS...
AGTAACTTTGAAAGCCCGGCGACAAATCTGAA....
         1450              1460              1470 ...

FIG.19H

```
         ...  VAL  LYS  GLN  GLU  GLY  THR  ASN  PHE  THR  TYR
         ...G G T C A A A C A A G A G G G C A C A A A C T T C A C T T A
            ...                       1480                       1490                       1500

ALA  LEU  LYS  ASP  GLU  GLY  LEU  THR  GLY  VAL  LYS...
C G C G C T C A A A G A T G A A T T G A C G G G C G T G A A...
                  1510                       1520                       1530 ...

...  SER  VAL  GLU  PHE  LYS  ASP  THR  ALA  ASN  GLY
                                  ...G A G C G T G G A G T T T A A A G A C A C G G C G A A T G G
                                         ...              1540                       1550                       1560

ALA  ASN  GLY  ALA  SER  THR  LYS  ILE  THR  LYS...
T G C A A A C G G T G C A A G C A C G A A G A T T A C C A A...
                  1570                       1580                       1590 ...

...  ASP  GLY  LEU  THR  ILE  THR  LEU  ALA  ASN  GLY
                                  ...A G A C G G C T T G A C C A T T A C G C T G G C A A A C G G
                                         ...              1600                       1610                       1620

ALA  ASN  GLY  ALA  THR  VAL  THR  ASP  ALA  ASP...
T G C G A A T G G T G C G A C G G T G A C T G A T G C C G A...
                  1630                       1640                       1650 ...

...  LYS  ILE  LYS  VAL  ALA  SER  ASP  GLY  ILE  SER
                                  ...C A A G A T T A A A G T T G C T T C G G A C G G C A T T A G
                                         ...              1660                       1670                       1680
```

FIG. 191

```
ALA GLY ASN LYS ALA VAL LYS ASN VAL ALA...
CGCGGGGTAATAAAGCAGTTAAAAACGTCGC...
       1690                1700              1710
                                        ALA GLY GLU ILE SER ALA THR SER THR ASP
                                    ...GGCAGGCGAAATTTCTGCCACTTCCACCGA
                                           1720             1730             1740

ALA ILE ASN GLY SER GLN LEU TYR ALA VAL...
TGCGATTAACGGAAGCCAGTTGTATGCCGT...
       1750                1760              1770
                                        ALA LYS GLY VAL THR ASN LEU ALA GLY GLN
                                    ...GGCAAAAGGGGTAACAAACCTTGCTGGACA
                                           1780             1790             1800

VAL ASN ASN LEU GLU GLY LYS VAL ASN LYS...
AGTGAATAATCTTGAGGGCAAAGTGAATAA...
       1810                1820              1830
                                        VAL GLY LYS ARG ALA ASP ALA GLY THR ALA
                                    ...AGTGGGCAAACGTGCAGATGCAGGTACTGC
                                           1840             1850             1860

SER ALA LEU ALA ALA SER GLN LEU PRO GLN...
AAGTGCATTAGCGGCTTCACAGTTACCACA
       1870                1880              1890
```

FIG.19J

```
              ALA THR MET PRO GLY LYS SER MET VAL SER
          ...AGCCACTATGCCAGGTAAATCAATGGTTTC
              1900              1910              1920
          ...
ILE ALA GLY SER SER TYR GLN GLY GLN ASN...
TATTGCGGGAAGTAGTTATCAAGGTCAAAA...
              1930              1940              1950 ...
                                               ...
              GLY LEU ALA ILE GLY VAL SER ARG ILE SER
          ...TGGTTTAGCTATCGGGGTATCAAGAATTTC
              1960              1970              1980
                                               ...
ASP ASN GLY LYS VAL ILE ILE ARG LEU SER...
CGATAATGGCAAAGTGATTATTCGCTTGTC
              1990              2000              2010 ...
                                               ...
              GLY THR THR ASN SER GLN GLY LYS THR GLY
          ...AGGCACAACCAATAGTCAAGGTAAAACAGG
              2020              2030              2040
                                               ...
VAL ALA ALA GLY VAL GLY TYR GLN TRP ***
CGTTGCAGCAGGTGTTGGTTACCAGTGGTA...   ...ATAGAATTC
```

FIG.20A

NTHi strain 29 Hia

```
                                    MET ASN LYS....
T T A A A T A T A A G G T A A A T A A A A A T G A A C A A A...
                   10                  20                 30...

ILE PHE ASN VAL ILE TRP ASN VAL VAL THR
...A T T T T T A A C G T T A T T T G G A A T G T T G T G A C T
                   40                  50                 60

GLN THR TRP VAL VAL VAL SER GLU LEU THR....
C A A A C T T G G G T T G T C G T A T C T G A A C T C A C T...
                   70                  80                 90...

ARG ALA HIS THR LYS CYS ALA SER ALA THR
...C G C G C C C A C C A A A T G C G C C T C C G C C A C C
                   100                 110                120

VAL ALA VAL ALA VAL LEU ALA THR ALA LEU....
G T G G C G G T T G C C G T A T T G G C A A C T G C G T T G...
                   130                 140                150...

SER ALA THR ALA GLU ALA ASN ASN THR
...T C T G C A A C G G C T G A A G C G A A C A A T A C T
                   160                 170                180

SER VAL THR ASN GLY LEU ASN ALA TYR GLY....
T C T G T T A C G A A T G G G T T G A A T G C T T A T G G C...
                   190                 200                210...
```

FIG.20B

```
                                          ...ASP THR ASN PHE ASN THR THR ASN ASN SER
                                          ...GATACTAATTTTAATACAACCAATAATTCG
                                                                        230       240

ILE ALA ASP LEU GLU LYS HIS VAL GLN ASP...
ATAGCAGATTTGGAAAAACACGTTCAAGAT...
             250              260             270...

...ALA TYR LYS GLY LEU LEU ASN LEU ASN GLU
                                          ...GCTTATAAAGGCTTATTAAATCTGAATGAA
                                                               280                300

LYS ASP THR ASN LYS SER SER PHE LEU VAL...
AAAGATACAAATAAGTCAAGTTTCTTGGTT...
             310              320              330...

...ALA ASP ASN THR ALA ALA THR VAL GLY ASN
                                          ...GCCGACAATACCGCGGCAACCGTAGGCAAT
                                                     340              350        360

LEU ARG LYS LEU GLY TRP VAL LEU SER SER...
TTGCGTAAATTGGGCTGGGTATTGTCTAGC...
             370              380              390...

...LYS ASN GLY THR ARG ASN GLU LYS SER TYR
                                          ...AAAAACGGCACAAGGAACGAGAAAAGCTAT
                                                     400              410        420
```

FIG.20C

GLN VAL LYS GLN ALA ASP GLU VAL LEU PHE ...
CAAGTAAAACAAGCTGATGAAGTTCTCTTT...
         430                440              450...

THR GLY SER GLY ALA ALA THR VAL SER SER
        ...ACTGGATCTGGTGCTGCAACGGTTAGTTCC
            460              470              480

SER SER LYS ASP GLY LYS HIS THR ILE THR ...
AGCTCTAAAGACGGTAAACATACCATTACC...
         490                500              510...

ILE SER VAL THR LYS GLY SER PHE ALA GLU
        ...ATTTCTGTTACCAAAGGTAGTTTTGCTGAG
            520              530              540

VAL LYS THR ASP ALA THR GLY GLY GLN ...
GTAAAAACTGATGCAACTACTGGAGGTCAA...
         550                560              570...

VAL ASN ALA ASP ARG GLY LYS VAL LYS ALA
        ...GTAAACGCCGACCGTGGTAAAGTGAAAGCT
            580              590              600

GLU ASP GLU ASN GLY ALA ASP VAL ASP LYS ...
GAGGACGAGAATGGAGCTGATGTTGATAAG...
         610                620              630...

FIG.20D

```
                                      ... LYS VAL ALA THR VAL LYS ASP VAL ALA LYS
                                      ... AAAGTTGCAACTGTAAAAGATGTTGCTAAG
                                              640           650            660

ALA ILE ASN ASP ALA ALA THR PHE VAL LYS ...     ... VAL GLU SER THR ASP ASP ILE GLU ASN
GCGATTAACGATGCCGCAACTTTCGTGAAA...               ...GTGGAAAGCACAGATGATGACATTGAAAAT
        670              680          690....           700           710            720

GLY ALA ALA GLY LYS ASN GLU THR THR ASP ...     ... GLN ALA LEU LYS ALA GLY ASP THR LEU THR
GGTGCTGCAGGCAAAAATGAAACTACAGAC...               ...CAAGCTCTCAAAGCAGGCGACACCTTAACC
        730              740          750....           760           770            780

LEU LYS ALA GLY LYS ASN LEU LYS ALA LYS ...     ... LEU ASP GLN ASN GLY LYS SER VAL THR PHE
TTAAAAGCGGGTAAAAACTTAAAAGCTAAG...               ...TTAGACCAAAATGGTAAATCAGTAACCTTT
        790              800          810....           820           830            840
```

FIG.20E

ALA LEU ALA LYS ASP LEU ASP VAL THR SER....
GCTTTAGCGAAAGACCTTGATGTGACCTCT...
          850              860          870....
                  ...ALA LYS VAL SER ASP LYS LEU SER ILE GLY
                  ...GCGAAAGTGAGTGATAAGTTGTCTATTGGT
                            880             890             900

LYS ASP THR ASN LYS VAL ASP ILE THR SER....
AAAGATACGAATAAAGTTGATATTACCAGT...
          910             920           930....
                  ...ASP ALA ASN GLY LEU LYS LEU ALA LYS THR
                  ...GATGCAAATGGCTTGAAATTGGCGAAAACA
                            940             950             960

GLY ASN GLY ASN GLY GLN ASN GLY ASN VAL....
GGTAACGGAAATGGTCAAAACGGTAATGTC...
          970             980           990....
                  ...HIS LEU ASN GLY ILE ALA SER THR LEU THR
                  ...CACTTAAATGGTATTGCTTCGACTTTGACC
                            1000            1010            1020

ASP THR ILE THR GLY MET THR THR GLN ALA....
GATACCATTACAGGTATGACAACACAAGCA...
          1030            1040          1050....

FIG.20F

```
                                              ... SER ASN GLY VAL ALA VAL GLN ASN HIS ASN
                                              ... AGCAATGGCGTGGCTGTGCAGAATCATAAT
                                                  1060                    1070         1080

ARG ALA ALA SER VAL ALA ASP VAL LEU ASN ...           ALA GLY TRP ASN ILE GLN GLY ASN GLY ALA
CGTGCTGCGAGTGTGGCTGATGTATTAAAT...                     GCAGGCTGGAATATTCAAGGCAACGGAGCG
    1090                    1100         1110...         1120                    1130         1140

SER VAL ASP PHE VAL ALA ASN ALA TYR ASP THR ...       VAL ASP PHE VAL ASN GLY THR ASN THR ASN
AGCGTTGATTTTGTCAATGCTTACGACACA...                     GTAGATTTTGTCAATGGTACAAACACCAAT
    1150                    1160         1170...         1180                    1190         1200

VAL ASN VAL THR THR ASP THR ALA HIS LYS ...           LYS THR THR VAL ARG VAL ASP VAL THR GLY
GTGAACGTTACGACTGATACGGCTCACAAA...                     AAGACAACCGTCCGTGTGGATGTAACAGGC
    1210                    1220         1230...         1240                    1250         1260
```

FIG.20G

```
LEU PRO VAL GLN TYR VAL THR GLU ASP GLY...
TTGCCCGGTTCAATATATGTTACGGAAGACGGC...
         1270              1280              1290
                                    ... LYS THR VAL VAL LYS VAL ASP ASN LYS TYR
                                    ...AAAACCGTTGTGAAAGTGGACAATAAGTAT
                                              1300              1310              1320

TYR GLU ALA LYS GLN ASP GLY SER ALA ASP....
TACGAAGCTAAGCAAGACGGTTCGGCGGAT....
         1330              1340              1350
                                    ... MET ASP LYS LYS VAL GLU ASN GLY GLU LEU
                                    ...ATGGATAAAAAGTCGAAAATGGCGAGCTG
                                              1360              1370              1380

ALA LYS THR LYS VAL LYS LEU VAL LYS SER ALA....
GCGAAAACCAAAGTGAAATTGGTGTCGGCA....
         1390              1400              1410
                                    ... SER GLY GLN ASN PRO VAL LYS ILE SER ASN
                                    ...AGCGGTCAAAATCCGGTGAAAATCAGCAAT
                                              1420              1430              1440

VAL ALA GLU GLY THR GLU GLU ASN ASP ALA....
GTTGCGGAAGGCACGGAAGAAAACGATGCG...
         1450              1460              1470
```

FIG.20H

```
                                          ... VAL SER PHE LYS GLN LEU LYS ALA LEU GLN
                                          ... G T C A G C T T T A A G C A A T T G A A A G C C T T G C A A
                                                                          1480           1490          1500

GLU LYS GLN VAL THR LEU THR ALA SER ASN ...
G A G A A A C A G G T T A C T T T A A C T G C G A G C A A T ...
                     1510              1520         1530...

... ALA TYR ALA ASN GLY GLY ASN ASP ALA ASP
                                          ... G C T T A T G C C A A T G G T G G T A A C G A T G C C G A C
                                                                          1540           1550          1560

GLY GLY LYS ALA THR GLN THR LEU ASN ASN ...
G G C G G C A A G G C A A C T C A A A C T T T A A A C A A T ...
                     1570              1580         1590...

... GLY LEU ASN PHE LYS PHE LYS SER THR ASP
                                          ... G G T T T G A A T T T T A A A T T T A A A T C C A C A G A C
                                                                          1600           1610          1620

GLY GLU LEU LEU ASN ILE LYS VAL GLU ASN ...
G G C G A G T T G T T G A A C A T C A A A G T A G A A A A T ...
                     1630              1640         1650...

... ASP THR VAL THR PHE THR PRO LYS LYS GLY
                                          ... G A C A C A G T T A C C T T T A C G C C G A A A A A G G T
                                                                          1660           1670          1680
```

FIG. 20I

```
SER VAL GLN VAL GLY GLU ASP GLY LYS ALA....      THR ILE GLN ASN GLY THR LYS THR THR ASP
T C G G T A C A G G T T G G C G A A G A C G G T A A G G C T...   ...A C G A T T C A A A A T G G T A C G A A A A C A A C C G A C
                        1690                             1700             ...       1710                        1720                        1730                        1740

GLY LEU VAL GLU ALA SER GLU LEU VAL GLU....      SER LEU ASN LYS LEU GLY TRP LYS VAL GLY
G G T T T G G T T G A A G C T T C C G A A T T G G T T G A A...   ...A G C C T G A A C A A A C T G G G C T G G A A A G T G G G C
                        1750                                   1760           ...       1770                        1780                        1790                        1800

VAL ASP LYS ASP GLY SER GLY GLU LEU ASP....      GLY ALA SER ASN GLU THR LEU VAL LYS SER
G T T G A T A A A G A C G G C A G C G G C G A G C T T G A T...   ...G G T G C A T C C A A T G A A A C T T T A G T G A A G T C G
                        1810                                   1820           ...       1830                        1840                        1850                        1860

GLY ASP LYS VAL THR LEU LYS ALA GLY GLU....
G G C G A T A A A G T A A C T T T G A A A G C C C G G A G...
                        1870                                   1880                        1890
```

FIG. 20J

```
                              ASN LEU LYS VAL LYS GLN ASP GLY THR ASN
                          ... A A T C T G A A G G T C A A A A C A A G A C G G C A C A A A C
                          ...                        1900                        1910                        1920

PHE THR TYR ALA LEU LYS ASP GLU LEU THR ...
T T C A C T T A C G C G C T C A A A G A T G A A T T G A C G ...
                        1930                        1940                        1950 ...

GLY VAL LYS SER VAL GLU PHE LYS ASP THR
                          ... G G C G T G A A G A G C G T G G A G T T T A A A G A C A C G
                          ...                        1960                        1970                        1980

ALA ASN GLY SER ASN GLY ALA SER THR LYS ...
G C G A A T G G T T C A A A C G G T G C A A G C A C G A A G ...
                        1990                        2000                        2010 ...

ILE THR LYS ASP GLY LEU THR ILE THR SER
                          ... A T T A C C A A A G A C G G C T T G A C C A T T A C G T C G
                          ...                        2020                        2030                        2040

ALA ASN GLY ALA ASN GLY ALA ALA ALA THR ...
G C A A A C G G T G C G A A T G G T G C G G G G G C G A C T ...
                        2050                        2060                        2070 ...

ASP ALA ASP ASN GLY ILE LYS VAL ALA SER ASP
                          ... G A T G C G G A C A A G A T T A A A G T G G C T T C A G A C
                          ...                        2080                        2090                        2100
```

FIG. 20K

```
GLY ILE SER ALA GLY ASN LYS ALA VAL LYS                    ASN VAL VAL SER GLY LEU LYS LYS PHE GLY
GGCATCAGTGCGGGTAATAAAGCGGTTAAA...               ...AACGTTGTGAGCGGACTGAAGAAATTTGGT
             2110                    2120                  2130...        2140                   2150                 2160

ASP ALA ASN PHE ASN PRO LEU THR SER SER              ...ALA ASP ASN LEU THR LYS GLN TYR ASP ASP
GATGCGAATTTCAATCCACTGACCAGTTCC...             ...GCCGACAACTTAACGAAACAAATATGACGAT
             2170                    2180                 2190...         2200                   2210                 2220

ALA TYR LYS GLY LEU THR ASN LEU ASP GLU           ...LYS GLY ALA ASP LYS GLN THR LEU THR VAL
GCCTATAAAGGCTTGACCAATTTGGATGAA...             ...AAAGGTGCGGACAAGCAAACTCTGACTGTT
             2230                    2240                 2250...         2260                   2270                 2280

ALA ASP ASN THR ALA ALA THR VAL GLY ASP ...
GCCGACAATACTGCCGCAACCGTGGGCGAT...
             2290                    2300                 2310...
```

FIG. 20L

```
        ... LEU ARG GLY LEU GLY TRP VAL ILE SER ALA
        ... T T G C G C G G C T T G G G C T G G G T C A T T T C T G C G
            2320                        2330                        2340
        ...

ASP LYS THR THR GLY GLU LEU ASN LYS GLU ...
G A C A A A A C C A C A G G C G A A C T C A A T A A G G A A ...
            2350                        2360                        2370...
                                                                    ...
                ... TYR ASN ALA GLN VAL ARG ASN ALA ASN GLU
                ... T A C A A C G C C A A G T G C G T A A C G C C A A T G A A
                        2380                        2390                        2400
                                                                                ...

VAL LYS PHE LYS SER GLY ASN GLY ILE HIS ...
G T G A A A T T C A A G A G C G G C A A C G G T A T C C A T ...
            2410                        2420                        2430...
                                                                    ...
                ... VAL SER GLY LYS THR VAL ASN GLY ARG ARG
                ... G T T T C C G G T A A A A C G G T C A A C G G T A G G C G C
                        2440                        2450                        2460

GLU ILE THR PHE GLU LEU ALA LYS ASP GLU ...
G A A A T T A C T T T T G A A T T G G C T A A A G A C G A A ...
            2470                        2480                        2490...
                                                                    ...
                ... ASN ALA ILE ALA PHE GLY TYR GLY SER LYS
                ... A A T G C C A T T G C T T T C G G T T A T G G C T C A A A A A
                        2500                        2510                        2520
                                                                                ...
```

FIG.20M

```
ALA LEU ARG ASP ASN THR VAL ALA ILE GLY ....      THR GLY ASN VAL VAL ASN ALA GLU LYS SER
G C C T T G C G C G A T A A C A C G G T G G C A A T T G G T ...    ... A C G G G C A A C G T T G T G A A T G C G G A A A A A T C T
                   2530                   2540         2550...                              2560                   2570                  2580

GLY ALA PHE GLY ASP PRO ASN TYR ILE GLU ....      ASP LYS ALA GLY GLY SER TYR ALA PHE GLY
G G T G C A T T C G G C G A T C C G A A C T A C A T C G A A...    ... G A T A A A G C C G G T G G C A G C T A C G C T T T C G G T
                   2590                   2600         2610...                              2620                   2630                  2640

ASN ASP ASN ARG ILE THR SER LYS ASN THR ....      PHE VAL LEU GLY ASN GLY VAL ASN ALA LYS
A A C G A T A A C C G T A T T A C T T C T A A A A A C A C T...    ... T T T G T G T T G G G T A A T G G A G T T A A T G C G A A A
                   2650                   2660         2670...                              2680                   2690                  2700

TYR LYS ALA ASN GLY ASP VAL ASP THR GLU ....
T A T A A A G C C A A T G G A G A T G T T G A T A C G G A A...
                   2710                   2720         2730...
```

FIG.20N

```
        ...  THR VAL THR VAL LYS ASP LYS ASP GLY LYS
        ...  A C C G T A A C C G T T A A G G A C A A A G A C G G T A A A
                                    2740            2750            2760

GLU THR THR VAL THR VAL PRO LYS ALA LEU  ...
G A G A C T A C C G T T A C T G T T C C T A A A G C G T T A  ...
        2770            2780            2790      ...

...  GLY ALA THR VAL VAL GLU ASN SER VAL TYR LEU
                            ...  G G G G C T A C G G T T G A A A A C T C C G T T T A T T T G
                                        2800            2810            2820

GLY ASN LYS SER THR ALA THR LYS ASP LYS  ...
G G T A A T A A A T C G A C T G C G A C A A A A G A T A A G  ...
        2830            2840            2850      ...

...  GLY LYS ASN LEU LYS SER ASP GLY THR ALA
                            ...  G G T A A A A A C C T G A A A T C T G A T G G T A C G G C G
                                        2860            2870            2880

GLY ASN THR THR ALA GLY THR THR GLY  ...
G G T A A C A C T A C A G C T G G C A C A A C G G G T  ...
        2890            2900            2910      ...

...  THR VAL ASN GLY PHE ALA GLY ALA THR ALA
                            ...  A C G G T A A A C G G C T T T G C C G G T G C A A C G G C G
                                        2920            2930            2940
```

FIG.20O

HIS GLY ALA VAL SER VAL GLY ALA SER GLY ... GLU GLU ARG ARG ILE GLN ASN VAL ALA ALA
CACGGGTGCGGTTTCTGTCGGCGCAAGCGGC... ...GAAGAAAGACGTATCCAAAACGTCGCGGCA
        2950                      2970....        2980           2990              3000

GLY GLU ILE SER ALA THR SER THR ASP ALA ... ILE ASN GLY SER GLN LEU TYR ALA VAL ALA
GGCGAAATTTCCGCCACTTCCACCGATGCG... ...ATTAACGGCCAGCCAGTTGTATGCTGTGGCA
        3010                      3030....        3040           3050              3060

LYS GLY VAL THR ASN LEU ALA GLY GLN VAL ... ASN LYS VAL GLY LYS ARG ALA ASP ALA GLY
AAAGGGGTAACAAATCTTGCTGGACAAGTG... ...AATAAAGTGGGCAAAACGTGCAGATGCAGGT
        3070                      3090....        3100           3110              3120

THR ALA SER ALA LEU ALA ALA SER GLN LEU ....
ACAGCAAGTGCATTAGCAGCTTCACAGTTA....
        3130                      3150....

FIG.20P

```
                          ...  PRO  GLN  ALA  SER  MET  PRO  GLY  LYS  SER  MET
                          ...C C A C A A G C C T C T A T G C C A G G T A A A T C A A T G
                          ...                            3160                      3170                       3180

VAL  SER  ILE  ALA  GLY  SER  SER  TYR  GLN  GLY  ...
G T T T C T A T T G C G G G A A G T A G T T A T C A A G G T...
              3190                      3200                      3210...

...  GLN  ASN  GLY  LEU  ALA  ILE  GLY  VAL  SER  ARG
                          ...C A A A A T G G T T T A G C T A T C G G G G T A T C A C G A
                          ...                            3220                      3230                       3240

ILE  SER  ASP  ASN  GLY  LYS  VAL  ILE  ILE  ARG  ...
A T T T C C G A T A A T G G C A A A G T G A T T A T T C G C...
              3250                      3260                      3270...

...  LEU  SER  GLY  THR  THR  ASN  SER  GLN  GLY  LYS
                          ...T T G T C A G G C A C A A C C A A T A G C C A A G G T A A A
                          ...                            3280                      3290                       3300

THR  GLY  VAL  ALA  ALA  GLY  VAL  GLY  TYR  GLN  ...
A C A G G C G T T G C A G C A G G T G T T G G T T A C C A G...
              3310                      3320                      3330...

...  TRP  ***
                          ...T G G T A A T A G A A T T C C G G A T C C G C
                          ...                            3340                      3350
```

FIG.21A

NTHi strain M4071 Hia

```
        MET ASN LYS ILE PHE ASN VAL...
        GCGAATTCATATGAACAAAAATTTTAACGT...
                        10              30 ...
                                     20
        ...ILE TRP ASN VAL MET THR GLN THR TRP ALA
        ...TATTTGGAATGTTATGACTCAAACTTGGGC
              40                50              60

VAL VAL SER GLU LEU THR ARG ALA HIS THR....
TGTCGTATCTGAACTCACTCGCGCCCACAC....
            70              80              90 ....

...LYS ARG ALA SER ALA THR VAL ALA THR ALA
    ...CAAACGTGCCTCCGCAACCGTGGCAACCGC
              100             110             120

VAL LEU ALA THR LEU LEU SER THR THR VAL...
CGTATTGGCGACGTTGTGTCTACAACAGT...
            130             140             150 ....

...GLN ALA THR THR THR GLY GLY THR THR SER
    ...TCAGGCGACAACTACTGGCGGTACGACAAG
              160             170             180

THR ASN GLY LEU LEU LYS ALA TYR GLY SER THR....
TACAAACGGTTTGAAAGCTTATGGAAAGTAC....
            190             200             210 ....
```

FIG.21B

```
                          ASN ASN PRO ASN PHE ASN ALA ALA GLY ASN
                       ...GAATAATCCGAATTTCAATGCTGCAGGTAA
                                                        240
                       ...

SER ALA THR ASP LEU ALA ARG GLN PHE ASP...
CTCTGCAACTGATTTAGCTAGACAGTTTGA...
              250                  260              270 ...

GLY ALA TYR ASP GLY LEU LEU ASN LEU ASN
                       ...TGGTGCTTATGACGGTTTATTAAATCTAAA
                                          280                  300
                       ...

GLU LYS ASP ALA ASN LYS ASN LEU LEU VAL...
TGAAAAGATGCGAATAAAAATCTGTTGGT...
              310                  320              330 ...

THR ASP ASP LYS ALA ALA THR VAL GLY ASN
                       ...GACTGATGATAAGGCGGCGACCGTAGGCAA
                                          340                  360
                       ...

LEU ARG LYS LEU GLY TRP VAL LEU SER SER...
TTTGCGTAAATTGGGTTGGGTATTGTCTAG...
              370                  380              390 ...

LYS ASN GLY THR ARG ASN GLU LYS SER GLN
                       ...TAAAAACGGCACAAGGAACGAGAAAAGCCA
                                          400                  420
                       ...
```

FIG.21C

```
GLN VAL LYS HIS ALA ASP GLU VAL LEU PHE...
ACAAGTCAAAACACGCGGATGAAGTGTTGTT....
            430            440           450
                               GLU GLY LYS ASP GLY VAL THR VAL THR SER
                            ...TGAAGGCAAAGACGGTGTAACGGTTACTTC
                                      460           470           480

LYS SER GLU ASN GLY LYS HIS THR VAL THR...
CAAATCTGAAAACGGTAAACACACCGTTAC....
            490            500           510
                               PHE THR LEU GLU LYS ASP LEU ASN VAL LYS
                            ...TTTTACCCTTGAGAAAGACCTTAATGTAAA
                                      520           530           540

ASN ALA THR VAL SER ASP LYS LEU SER LEU...
AAACGCAACCGTTAGCGATAAATTATCGCT....
            550            560           570
                               GLY ALA ASN GLY ASN LYS VAL ASP ILE THR
                            ...TGGTGCAAACGGCAATAAAGTCGATATTAC
                                      580           590           600

SER ASP THR ASN GLY LEU LYS PHE ALA LYS...
CAGTGATACAAACGGCTTGAAATTTGCGAA....
            610            620           630
```

FIG.21D

```
                                            PRO SER THR ASN GLY GLN ASN GLY ASN VAL
                                        ...A C C A A G T A C G A A T G G T C A A A A C G G T A A T G T
                                        ...                                              660
                                                          650

HIS LEU ASN GLY ILE ALA SER THR LEU THR...      ASP THR ILE THR GLY THR THR LYS SER ALA
T C A C T T A A A C G G T A T T G C C T C T A A C... T G A C A C A A T T A C A G G T A C A A A A T C T G C
                      670                    680 ...                      700              720
                                                                                     710

THR ASN GLY VAL ASP VAL GLN ASN HIS ASN...      ARG ALA ALA SER VAL ALA ASP VAL LEU ASN
A A C T A A T G G T G T A G A T G T G C A G A A T C A T A A... T C G T G C T G C G A G T G T A G C T G A T G T A T T G A A
                      730                    740 ...            760                        780
                                                                          770

ALA GLY TRP ASN ILE GLN GLY ASN GLY ALA...      SER VAL ASP PHE VAL ASN THR TYR ASP THR
T G C A G G C T G G A A T A T T C A A G G C A A C G G A G C... G A G C G T T G A T T T T G T C A A T A C T T A C G A C A C
                      790                    800 ...            820                        840
                                                          810                        830
```

FIG. 21E

VAL ASP PHE VAL ASN GLY LEU ASN THR ASN...
AGTAGATTTTGTCAATGGTTTAAATACCAA...
　　　　　850　　　　　　　　860　　　　　　　870....

VAL ASN VAL THR THR ASP THR ALA HIS ASN
　　　　　　　...TGTGAACGTTACGACTGATACGGCTCACAA
　　　　　　　　　　　　　880　　　　　　　890　　　　　　　900

LYS LYS THR THR VAL ARG VAL ASP VAL THR....
CAAAAAGACAACCGTCCGTGTGGATGTAAC...
　　　　　910　　　　　　　　920　　　　　　　930....

GLY LEU PRO VAL GLN TYR VAL THR GLU ASP
　　　　　　　...GGGCTTGCCCGGTCCAATATGTTACGGAAGA
　　　　　　　　　　　　　940　　　　　　　950　　　　　　　960

GLY GLU THR VAL VAL LYS VAL GLY ASN GLU...
CGGCGAAACCGTTGTGTGAAAGTGGGCAATGA...
　　　　　970　　　　　　　　980　　　　　　　990....

TYR TYR GLU ALA LYS GLN ASP GLY SER ALA
　　　　　　　...GTATTACGAAGCCAAGCAAGACGGTTCGGC
　　　　　　　　　　　　　1000　　　　　　1010　　　　　　1020

ASP MET ASP LYS LYS LYS VAL GLU ASN GLY LYS...
GGATATGGATAAAAAGAGTCGAAAATGGCAA...
　　　　　1030　　　　　　　1040　　　　　　1050....

FIG.21F

```
...    LEU ALA LYS THR LYS VAL LYS LEU VAL SER
...GCTGGCGAAAACTAAAGTTAAATTGGTATC
                1070              1080

ALA ASN GLY THR ASN PRO VAL LYS ILE SER...
GGCAAACGGTACAAATCCGGTGAAAATCAG...
           1090             1100       1110 ...

...    ASN VAL ALA ASP GLY THR GLU ASN THR ASP
    ...CAATGTTGCGGATGGCACGGAAAATACCGA
                    1120             1130          1140

ALA VAL SER PHE LYS GLN LEU LYS ALA LEU...
TGCGGTCAGCTTTAAGCAGTTGAAAGCCTT...
          1150              1160      1170 ...

...    GLN ASP LYS GLN VAL THR LEU SER ALA SER
    ...GCAAGACAAACAGGTTACGTTAAGTGCGAG
                    1180             1190          1200

ASN ALA TYR ALA ASN GLY GLY SER ASP ALA...
CAATGCTTATGCCAATGGCGGTAGCGATGC...
         1210              1220      1230 ...

...    ASP GLY GLY LYS GLY ILE GLN THR LEU SER
    ...CGACGGGCGGCAAGGGAATTCAAACTTTAAG
                     1240              1250         1260
```

FIG. 21G

```
ASN GLY LEU ASN PHE LYS PHE LYS SER THR...
CAATGGTTTGAATTTTAAATTTAAATCCAC....
         1270              1280           1290   ...

ASP GLY LEU LEU ASN ILE LYS ALA GLU
                     ...AGACGGCGAGTTGTTGAATATCAAAGCAGA
                            1300              1310           1320

ASN ASP THR VAL THR PHE THR PRO LYS LYS...
AAATGACACGGTTACCTTTACGCCGAAAAAA....
         1330              1340           1350   ...

GLY SER VAL GLN VAL GLY ASP ASP GLY LYS
                     ...AGGTTCGGTGCAGGTTGGCGATGATGGTAA
                            1360              1370           1380

ALA THR ILE GLN ASP GLY ALA LYS THR THR...
GGCTACGATTCAAGACGGCGCAAAAACAAC....
         1390              1400           1410   ...

THR GLY LEU VAL GLU ALA SER GLU LEU VAL
                     ...TACCGGTTTGGTTGAGGCTTCTGAATTGGT
                            1420              1430           1440

ASP SER LEU ASN LYS LEU GLY TRP LYS VAL...
TGACAGCCCTGAACAAATTGGGTTGGAAAGT....
         1450              1460           1470   ...
```

FIG.21H

```
            ...GLY THR GLY ASP GLY THR GLY VAL THR
            ...GGGCACCGGCACTGACGGCACAGGAGTGAC
               1480         1490         1500

ASP GLY THR HIS THR ASP THR LEU VAL LYS...
CGATGGCACGCATACCGACACTTTAGTGAA...
       1510         1520         1530...

...SER GLY ASP LYS VAL THR LEU LYS ALA GLY
            ...GTCGGGCGATAAAGTAACTTTGAAAGCCGG
               1540         1550         1560

ASP ASN LEU LYS VAL LYS GLN GLU GLY THR...
CGACAATCTGAAGGTCAAACAAGAGGGTAC...
       1570         1580         1590...

...ASN PHE THR TYR ALA LEU LYS ASP GLU LEU
            ...AAACTTCACTTATGCGCTCAAAGATGAATT
               1600         1610         1620

THR ASP VAL LYS SER VAL GLU PHE LYS ASP...
GACGGACGTGAAGAGCGTGGAGTTTAAAGA...
       1630         1640         1650...

...THR ALA ASN GLY ALA ASN GLY ALA SER THR
            ...CACGGCGAATGGTGCAAACGGTGCAAGCAC
               1660         1670         1680
```

FIG. 21I

```
LYS  ILE  THR  LYS  ASP  GLY  LEU  THR  ILE  THR...
GAAGATTACCAAAGACGGGCTTGACCATTAC...
             1690              1700       1710 ...
                                             ... PRO  ALA  ASN  GLY  ALA  GLY  ALA  ALA  GLY  ALA
                                             ...GCCGGCAAACGGTGCGGGTGCGGCAGGTGC
                                                      1720              1730              1740

ASN  THR  ALA  ASN  THR  ILE  SER  VAL  THR  LYS...
AAACACTGCAAACACCATTAGCGTAACCAA...
             1750              1760       1770 ...
                                             ... ASP  GLY  ILE  SER  ALA  GLY  ASN  LYS  ALA  VAL
                                             ...AGACGGCATTAGCGCGGGTAATAAAGCAGT
                                                      1780              1790              1800

LYS  ASN  VAL  VAL  SER  GLY  LEU  LYS  LYS  PHE...
TAAAAACGTTGTGTGAGCGGGACTGAAGAAATT...
             1810              1820       1830 ...
                                             ... GLY  ASP  ALA  ASN  PHE  ASP  PRO  LEU  THR  SER
                                             ...TGGTGATGCGAATTTCGATCCGCTGACTAG
                                                      1840              1850              1860

SER  ALA  ASP  ASN  LEU  THR  LYS  GLN  TYR  ASP....
CTCAGCCGACAAACTTAACGAAACAATATGA
             1870              1880              1890
```

FIG.21J

```
              ASN ALA TYR LYS GLY LEU THR ASN LEU ASP
          ...C A A T G C C T A T A A A G G C T T G A C C A A T C T G G A
          ...                   1900              1910              1920

GLU LYS SER LYS GLY LYS GLN THR PRO THR...
T G A A A A A A G T A A A G G C A A A G C A A A C T C C G A C...
            1930              1940              1950      ...

VAL ALA ASP ASN THR ALA ALA THR VAL GLY
          ...C G T T G C T G A C A A T A C C G C T G C A A C C G T G G G
          ...                   1960              1970              1980

ASP LEU ARG GLY LEU GLY TRP VAL ILE SER...
C G A T T T G C G C G G G C T T G G G C T G G G T C A T T T C...
            1990              2000              2010      ...

ALA ASP LYS THR LYS GLY GLU LEU ASN LYS
          ...T G C A G A C A A A A C C A A A G G C T G A A C T C A A T A A
          ...                   2020              2030              2040

GLU TYR ASN ALA GLN VAL ARG ASN ALA ASN...
G G A A T A C A A C G C A C A A G T G C G T A A C G C T A A...
            2050              2060              2070      ...

GLU VAL LYS PHE LYS SER GLY ASN GLY ILE
          ...T G A A G T G A A A T T C A A G A G C G G C A A C G G T A T
          ...                   2080              2090              2100
```

FIG.21K

```
ASN VAL SER GLY LYS THR LEU ASP ASN GLY...
C A A T G T T T C C G G T A A A A C A T T G G A T A A C G G ...
                     2110                      2120                      2130 ...
                         ... THR ARG GLU ILE THR PHE GLU LEU ALA LYS
                         ...T A C G C G C G A A A T T A C T T T T G A A T T G G C T A A
                                 2140                      2150                      2160

ASP GLU ASN ALA ILE ALA PHE GLY SER GLY...
A G A C G A A A A T G C C A T T G C T T T C G G T T C T G G ...
                     2170                      2180                      2190 ...
                         ... SER LYS ALA LEU ARG ASP ASN THR VAL ALA
                         ...C T C A A A A G C C T T G C G C G A T A A C A C G G T G G C
                                 2200                      2210                      2220

ILE GLY THR GLY ASN VAL VAL ASN ALA GLU...
A A T T G G T A C G G G C A A C G T T G T G A A T G C G G A ...
                     2230                      2240                      2250 ...
                         ... LYS SER GLY ALA PHE GLY ASP PRO ASN TYR
                         ...A A A A T C T G G T G C A T T C G G C G A T C C G A A C T A
                                 2260                      2270                      2280

ILE GLU ASP LYS ALA GLY GLY SER TYR ALA...
C A T C G A A G A T A A A G C C G G T G G C A G C T A C G C ...
                     2290                      2300                      2310 ...
```

FIG.21L

```
                           PHE  GLY  ASN  ASP  ASN  ARG  ILE  THR  SER  LYS
                       ...T T T C G G T A A C G A T A A C C G T A T T A C T T C T A A
                                                                              2340
                       ...

ASN  THR  PHE  VAL  LEU  GLY  ASN  SER  VAL  ASN...
A A A C A C T T T T G T G T T G G G T A A T A G T G T T A A ...
                  2350                         2360         ...
                                                            ...

ALA  LYS  ARG  ASP  ALA  ASN  GLY  ASN  VAL  LEU
                   ...T G C G A A A C G T G A T G C A A A T G G C A A T G T T A C T
                                                                              2400
                   ...

THR  GLU  GLU  LYS  GLU  VAL  VAL  GLY  LYS  ASP...
G A C C G A A G A A A A A G A A G T G G T T G G A A A A G A ...
                 2410                         2420          ...
                                                            ...

GLY  ALA  LYS  THR  LYS  VAL  THR  VAL  PRO  GLN
                   ...C G G T G C G A A G A C G A A A G T A A C C G T G C C C G C A
                                                                              2460
                   ...

ALA  LEU  GLY  GLU  THR  VAL  GLU  ASN  SER  VAL...
A G C C C T T A G G C G A A A C C G T A G A A A A T T C T G T ...
                 2470                         2480         ...
                                                           ...

TYR. LEU  GLY  ASN  ALA  SER  THR  ALA  THR  LYS
                   ...T T A T C T C G G T A A T G C T T C A A C T G C G A C A A A A
                                                                              2520
                   ...
```

FIG.21M

```
ASP LYS GLY LYS ASN LEU LYS SER ASP GLY...
A G A T A A G G G T A A A A A C C T G A A A T C T G A T G G ...
                    2530                      2540                    2550

THR ALA GLY ASN THR THR ALA GLY ALA
           ...T A C G G C G G G T A A C A C T A C A A C T G C T G G C G C
                         2560                 2570                 2580
           ...

THR GLY THR VAL ASN GLY PHE ALA GLY ALA...
A A C G G G T A C G G T A A A C G G C T T T G C C G G T G C ...
               2590                   2600                  2610

THR ALA HIS GLY ALA VAL SER VAL GLY ALA
              ...A A C G G C C A C G G T G C G G T T T C T G T C G G C G C
                              2620                2630                 2640
              ...

SER GLY GLU GLU ARG ARG ILE GLN ASN VAL...
A A G T G G C G A A G A A A G A C G T A T C C A A A A C G T ...
                 2650                  2660                2670

ALA ALA GLY ILE GLU ASN ALA THR SER THR
              ...C G C G G C A G G C G A A A T T T C C G C T A C T T C C A C
                                2680                 2690                2700
              ...

ASP ALA ILE ASN GLY SER GLN LEU TYR ALA...
A G A T G C G A T T A A C G G T A G C C A G T T G T A T G C ...
                    2710                   2720                 2730
```

FIG.21N

```
         ...  VAL  ALA  LYS  GLY  VAL  THR  ASN  LEU  ALA  GLY
         ...  TGTGGCAAAAGGGGTAACAAACCTTGCTGG
                                           2750              2760
         ...

GLN  VAL  ASN  LYS  VAL  GLY  LYS  ARG  ALA  ASP ...
ACAAGTGAATAAAGTGGGCAAACGTGCAGA ...
                       2780                    2790 ...

...  ALA  GLY  THR  ALA  SER  ALA  LEU  ALA  ALA  SER
         ...  TGCAGGTACAGCAAGTGCATTAGCGGCTTC
                                  2810                      2820
         ...

GLN  LEU  PRO  GLN  ALA  SER  MET  PRO  GLY  LYS ...
ACAGTTACCACAAGCCCTCTATGCCAGGTAA ...
                       2840                    2850 ...

...  SER  MET  VAL  SER  ILE  ALA  GLY  SER  SER  TYR
         ...  ATCAATGGTTTCTATTGCGGGAAGTAGTTA
                          2860                  2870         2880
         ...

GLN  GLY  GLN  SER  GLY  LEU  ALA  ILE  GLY  VAL ...
TCAAGGTCAAAGTGGTTTAGCTATCGGGGT ...
               2890                      2900        2910 ...

...  SER  ARG  ILE  SER  ASP  ASN  GLY  LYS  VAL  ILE
         ...  ATCAAGAATTTCCGATAATGGCAAAGTGAT
                                    2920         2930        2940
         ...
```

FIG.21O

```
ILE  ARG  LEU  SER  GLY  THR  THR  ASN  SER  GLN...
T A T T C G C T T G T C A G G C A C A A C C A A T A G C C A ...
                        2950                    2970   ...
                                   GLY  LYS  THR  GLY  VAL  ALA  ALA  GLY  VAL  GLY
                             ...A G G T A A A A C A G G C G T T G C A G C A G G T G T T G G
                                   ...           2980                    2990           3000

TYR  GLN  TRP  ***  ***  ASN  SER  GLY  SER
T T A C C A G T G G T A A T A G A A T T C C C G G A T C C G C
                3010                    3030
```

FIG.22A    NTHi strain K9 hia sequence

```
MET ASN LYS ILE PHE ASN VAL ILE TRP ASN ...
ATGAACAAAATTTTTAACGTTATTTGGAAT...
                10              20              30...

VAL MET THR GLN THR TRP ALA VAL VAL SER
        ...GTTATGACTCAAACTTGGGCTGTCGTATCT
              40              50              60

GLU LEU THR ARG ALA HIS THR LYS ARG ALA ...
GAACTCACTCGCGCCCACACCAAACGTGCC...
          70              80              90...

SER ALA THR VAL ALA THR ALA VAL LEU ALA
        ...TCCGCAACCGTGGCGACCGCCGTATTGGCG
              100             110             120

THR GLN LEU SER ALA THR ALA GLU ALA ASN ...
ACGCAGTTGTCTGCAACGGCTGAAGCGAAC...
          130             140             150...

SER SER ALA SER VAL THR SER ARG LEU ASN
        ...AGTAGTGCTTCTGTTACGAGTAGGTTGAAT
              160             170             180

VAL TYR GLY ASP THR ASN THR LYS PHE ASN ...
GTTTATGGCGATACGAATACTAAATTCAAT...
          190             200             210...
```

FIG.22B

```
                            ...  ALA ALA ASN ASN SER ILE ALA ASP LEU ASN
                            ...  G C A G C C A A T A A T T C A A T A G C A G A T T T A A A T
                                                            220                 230                 240

LYS GLN ASN ASP GLY VAL HIS ASP GLY LEU ...          LEU ASN LEU ASN GLU ASN GLY ALA ASN LYS
A A A C A A A A T G A T G G T G T T C A C G A T G G T T T A ...   T T A A A T C T G A A T G A A A A C G G T G C G A A T A A A
                    250                 260          270...                 280                 290                 300

LYS LEU LEU VAL ASP ASP ASN THR ALA ALA ...          THR VAL GLY ASP LEU ARG LYS LEU GLY TRP
A A G C T G T T G G T G G A T G A C A A T A C T G C G G C G ...   A C C G T A G G C G A T T T A C G T A A A T T G G G C T G G
                    310                 320          330...                 340                 350                 360

VAL VAL SER THR LYS ASN GLY LYS GLU ASN ...          GLU LYS SER GLN GLN VAL LYS GLN ALA ASP
G T C G T A T C A A C C A A A A A T G G C A A G G A A A A T ...   G A G A A A A G C C A A C A A G T C A A A C A G G C G G A T
                    370                 380          390...                 400                 410                 420
```

FIG.22C

```
GLU VAL LEU PHE LYS GLY SER LYS GLY GLY ....         VAL GLN VAL THR SER THR SER GLU ASN GLY
GAAGTGTTGTTTAAAGGCAGCAAAGGCGGT...         ...GTGCAGGTTACTTCCACCTCTGAAAACGGC
          430                440                450....         ...          460                470                480

LYS HIS ALA ILE THR PHE ALA LEU ALA LYS ....         ASP LEU ASP MET ARG THR ALA THR VAL SER
AAACACGCCATTACCTTTGCTTTAGCGAAA...         ...GACCCTTGATATGAGAACTGCGACTGTGAGT
          490                500                510....         ...          520                530                540

ASP THR LEU THR ILE GLY GLY SER THR THR ....         THR GLY SER ALA THR THR PRO LYS VAL ASN
GATACCCTTAACGATTGGCGGTAGTACTACT...         ...ACAGGTAGTGCAACAACACCAAAAGTGAAT
          550                560                570....         ...          580                590                600

VAL THR SER THR ALA SER GLY LEU ASN PHE ....
GTGACTAGCACGGCAAGCGGCTTGAACTTT...
          610                620                630....
```

FIG.22D

```
                          ...ALA LYS GLY ALA THR GLY ALA ASN GLY ASP
                          ...GCGAAAGGCGCTACAGGTGCTAATGGCGAT
                                640        650        660

THR THR VAL HIS LEU THR ASN ILE ALA SER...        ...THR LEU GLN ASP THR LEU ASN THR GLY
ACTACGGTTCACTTGACTAATATTGCTTCA...                 ...ACTTTGCAAGATACTCTATTGAATACTGGG
         670        680        690                      700        710        720

VAL VAL SER LYS LEU ASP GLY ASN GLY ILE...        ...THR ALA ASP GLU LYS LYS ARG ALA ALA SER
GTTGTGAGTAAATTAGATGGTAATGGTATT...                 ...ACTGCTGACGAGAAAAAACGTGCGGCAAGC
         730        740        750                      760        770        780

VAL GLN ASP VAL LEU ASN SER GLY TRP ASN...        ...ILE LYS GLY VAL LYS THR GLY ALA THR THR
GTTCAAGATGTTTTAAATAGTGGTTGGAAT...                 ...ATCAAGGGTGTTAAAACAGGTGCGACGACT
         790        800        810                      820        830        840
```

FIG.22E

```
SER ASP ASN VAL ASP PHE VAL ARG THR TYR....
TCTGATAACGTTGATTTTGTCCGTACTTAC...
        850              860         870...

ASP THR VAL GLU PHE LEU SER GLY SER GLU
          ...GACACAGTTGAGTTTTTGAGCGGAAGTGAA
                  880              890              900

GLU THR THR LEU VAL THR VAL ASP SER GLU....
GAAACTACACTGGTTACAGTGGATAGTGAA
        910              920         930...

SER ASN GLY LYS SER THR LYS VAL LYS ILE
          ...AGTAATGGAAAATCTACTAAAGTTAAAATC
                  940              950              960

GLY ALA LYS THR SER VAL ILE LYS GLU LYS....
GGTGCGAAGACCTCTGTTATCAAAGAAAAA
        970              980         990...

ASP GLY LYS LEU PHE THR GLY LYS ALA ASN
          ...GACGGTAAGTTATTTACTGGAAAAGCTAAT
                  1000             1010             1020

LYS ASP THR ASN GLN VAL ALA SER ASN ASN....
AAAGACACAAATCAAGTCGCAAGTAATAAT
        1030             1040        1050...
```

FIG.22F

```
                              ...ALA ALA ASP ASP THR VAL ASP GLU GLY LYS GLY
                              ...GCAGCTGATGATACGGATGAGGCAAAGGC
                                                       1060             1070             1080

LEU VAL THR ALA GLU THR VAL ILE ASN ALA...
TTAGTCACTGCAGAGACTGTTATCAATGCA...
                 1090                  1100            1110...

...VAL ASN LYS ALA GLY TRP ARG ILE LYS THR
                              ...GTAAACAAGGCTGGTTGGAGAATTAAAACA
                                                       1120             1130             1140

THR GLY ALA ASN ASN GLN ALA GLY GLN PHE...
ACGGGTGCTAATAATCAAGCTGGTCAGTTT...
                 1150                  1160            1170...

...GLU THR VAL THR SER GLY THR ASN VAL THR
                              ...GAAACTGTCACATCAGGCACAAATGTAACC
                                                       1180             1190             1200

PHE ALA ASP GLY ASN GLY THR THR ALA VAL...
TTTGCTGATGGCAATGGTACAACTGCAGTC...
                 1210                  1220            1230...

...VAL THR GLY ASP ALA THR ASN GLY ILE THR
                              ...GTAACTGGCGATGCTACCAATGGTATTACT
                                                       1240             1250             1260
```

FIG.22G

| | | | | | |
|---|---|---|---|---|---|
| VAL | LYS | TYR | GLU | ALA | LYS | VAL | GLY | ASP | GLY ... |
| GTT | AAA | TAC | GAA | GCG | AAA | GTT | GGC | GAC | GGC ... |
| | | 1270 | | | | 1280 | | | 1290 ... |

... LEU LYS ILE GLY ASN ASP GLN LYS ILE THR
... TTG AAA GAT TGG TAA CGA CCA AAA ATC ACT
         1300              1310              1320

ALA ASP THR THR ALA LEU THR VAL THR GLY ...
GCA GAT ACG ACC GCA CTT ACT GTG ACG GGC ...
         1330              1340              1350 ...

... GLY LYS VAL THR ALA PRO ASP ALA THR ASN
... GGT AAA GTT ACT GCC CCT GAT GCA ACC AAT
         1360              1370              1380

GLY LYS LYS LEU VAL ASN ALA SER GLY LEU ...
GGT AAA GAA ACT TGT TAA ATG CAA GTG GTT TA ...
         1390              1400              1410 ...

... ALA ASP ALA LEU ASN LYS LEU SER TRP THR
... GCT GAT GCG TTA AAA CAA ATT AAG TTG GAC T
         1420              1430              1440

ALA LYS ALA GLU ALA ASP THR ALA ASN GLY ...
GCA AAA GCT GAA GCA GAT ACT GCT AAT GGC ...
         1450              1460              1470 ...

FIG.22H

```
          ...  GLY GLU GLU LEU ASP GLY THR ALA ASP GLU LYS
          ...  G G C G A G C T T G A T G G A A C T G C A G A T G A A A A A
                                      1480            1490           1500

GLU VAL LYS ALA GLY GLU THR VAL THR PHE ...
G A A G T T A A A G C A G G C G A A A C G G T A A C C T T T...
              1510                  1520           1530...

...  LYS ALA GLY LYS ASN LEU LYS VAL LYS GLN
          ...  A A A G C G G G C A A G A A C T T A A A A G T G A A A C A A
                             1540            1550           1560

ASP GLY ALA ASN PHE THR TYR SER LEU GLN ...
G A T G G T G C G A A C T T T A C T T A C T C A C T G C A A...
              1570                  1580           1590...

...  ASP ALA LEU THR GLY LEU THR SER ILE THR
          ...  G A T G C T T T A A C A G G C T T A A C G A G C A T T A C T
                             1600            1610           1620

LEU GLY THR GLY ASN ASN GLY ALA LYS THR ...
T T A G G T A C A G G A A A T A A T G G T G C G A A A A C T...
              1630                  1640           1650...

...  GLU ILE ASN LYS ASP GLY LEU THR ILE THR
          ...  G A A A T C A A A C A A A G A C G G C T T A A C C A T C A C A
                             1660            1670           1680
```

FIG.22I

PRO ALA ASN GLY ALA GLY ALA ASN ASN ALA...
CCAGCAAATGGTGCGGGTGCAAATAATGCA...
          1690              1700

...ASN THR ILE SER VAL THR LYS ASP GLY ILE
...AACACCATCAGCGTAACCAAAGACGGCATT
       1710          1720          1730          1740

SER ALA GLY GLY GLN SER VAL LYS ASN VAL...
AGTGCGGGCGGTCAGTCGGTTAAAAACGTT...
          1750              1760          1770

...VAL SER GLY ACT LEU LYS LYS PHE GLY ASP ALA
...GTGAGCGGGACTGAAGAAATTTGGTGATGCG
       1780          1790          1800

ASN PHE ASP PRO LEU THR SER SER ALA ASP...
AATTTCGATCCGCTGACTAGCTCCGCCGAC...
          1810              1820          1830

...ASN LEU THR LYS GLN TYR ASP ASP ALA TYR
...AACTTAACGAAACAATATGACGATGCCTAT
       1840          1850          1860

LYS GLY LEU THR ASN LEU ASP GLU LYS GLY ...
AAAGGCTTGACCAATTTGGATGAAAAAGGT...
          1870              1880          1890

FIG. 22J

```
                        ...ALA ASP LYS GLN THR LEU THR VAL ALA ASP
                        ...GCGGACAAGCAAACTCTGACTGTTGCCGAC
                           1900              1910              1920
                        ...

ASN THR ALA ALA THR VAL GLY ASP LEU ARG...
AATACTGCCGCAACCGTGGGCGATTTGCGC...
         1930              1940              1950...
                        ...GLY LEU GLY TRP VAL ILE SER ALA ASP LYS
                        ...GGCTTGGGCTGGGTCATTTCTGCGGACAAA
                           1960              1970              1980
                        ...

THR THR GLY GLU LEU ASP LYS GLU TYR ASN...
ACCACAGGCGAACTCGATAAGGAATACAAC...
         1990              2000              2010...
                        ...ALA GLN VAL ARG ASN ALA ASN GLU VAL LYS
                        ...GCGCAAGTGCGTAACGCCAATGAAGTGAAA
                           2020              2030              2040

PHE LYS SER GLY ASN GLY ILE ASN VAL SER...
TTCAAAAGCGGCAACGGTATCAATGTTTCC...
         2050              2060              2070...
                        ...GLY LYS THR VAL ASN GLY ARG ARG GLU ILE
                        ...GGTAAAACTGTCAACGGTAGGCGTGAAATT
                           2080              2090              2100
                        ...
```

FIG.22K

```
THR PHE GLU LEU ALA LYS GLY GLU VAL VAL...                    LYS SER ASN GLU PHE THR VAL LYS GLU THR
ACTTTTGAATTGGCTAAAGGCGAAGTGGTT...               ...AAAATCGAATGAATTTACTGTCAAAGAAACC
            2110                2120          2130...            2140                2150                2160

ASN GLY LYS GLU THR SER LEU VAL LYS VAL...                    GLY ASP LYS TYR TYR SER LYS GLU ASP ILE
AATGGCAAGGAAACGAGCCTGGTTAAAGTT...               ...GGCGATAAATATTACAGCAAAGAGGATATT
            2170                2180          2190...            2200                2210                2220

ASP PRO ALA THR GLY LYS PRO LYS VAL THR...                    ASN GLY ASN ALA VAL ALA ALA LYS TYR GLN
GACCCAGCAACCGGTAAACCGAAAGTTACA...               ...AATGGCAATGCAGTTGCTGCGAAATATCAA
            2230                2240          2250...            2260                2270                2280

ASP LYS ASP GLY LYS VAL VAL SER ALA ASP...
GATAAAGATGGCAAAGTCGTTTCTGCTGAC...
            2290                2300          2310...
```

FIG.22L

```
                          ...  GLY SER SER ASN THR ALA VAL THR LEU THR
                          ...  G G C A G C A G C A A T A C C G C T G T T A C C C T A A C C
                          ...                                 2320              2330              2340

ASN LYS GLY TYR GLY TYR VAL THR GLY ASN ....          ...  GLN VAL ALA ASP ALA ILE ALA LYS SER GLY
A A C A A A G G T T A T G G C T A T G T A A C A G G T A A C ....  C A A G T G G C A G A T G C G A T T G C G A A A T C A G G C
                2350              2360                          2370 ...              2380              2390              2400

PHE GLU LEU GLY LEU ALA ASP ALA GLU LYS ....          ...  ALA LYS ALA ALA PHE GLY ASP GLU THR LYS
T T T G A G C T T G G T T T G G C T G A T G C A G A A A A A ....  G C G A A A G C T G C G T T T G G C G A T G A A A C A A A A
                2410              2420                          2430 ...              2440              2450              2460

ALA LEU SER SER ASP LYS LEU GLU THR VAL ....          ...  ASN ALA ASN ASP LYS VAL ARG PHE ALA ASN
G C C T T G T C T T C T G A T A A A T T G G A A A C C G T A ....  A A T G C C A A C G A C A A A G T C C G T T T T G C T A A T
                2470              2480                          2490 ...              2500              2510              2520
```

FIG.22M

```
GLY LEU ASN THR LYS VAL SER ALA ALA THR ....
GGTTTAAATACCAAAGTGAGCGCGGCAACG...
              2530                    2550...

VAL GLU SER ILE ASP ALA ASN GLY ASP LYS
                    ...GTGGAAAGCATCGATGCAAACGGCGATAAA
                              2560              2570        2580

VAL THR THR PHE VAL LYS THR ASP VAL ....
GTGACTACAACCTTTGTGAAAACCGATGTG...
           2590                    2610...

GLU LEU PRO LEU THR GLN ILE TYR ASN THR
                    ...GAATTGCCTTTAACGCAAATCTACAATACC
                             2620              2630        2640

ASP ALA ASN GLY LYS LYS ILE VAL LYS ASN ....
GATGCAAACGGTAAGAAAATCGTTAAAAAT...
              2650                    2670...

GLY ASP LYS TRP TYR TYR THR LYS ASP ASP
                    ...GGCGATAAATGGTATTACACGAAAGATGAC
                              2680              2690        2700

GLY SER THR ASP MET THR LYS GLU VAL THR ....
GGCTCAACTGATATGACTAAAGAAGTTACC...
              2710                    2730
```

FIG.22N

```
                    ...  LEU GLY ASN VAL ASP SER ASP GLY LYS LYS
                    ...  C T T G G C A A T G T G G A T T C A G A C G G C A A G A A A
                         2740                    2750                    2760

VAL VAL LYS GLU ASP ASN LYS TRP TYR HIS ...
G T T G T G A A A G A A G A C A A C A A G T G G T A T C A C ...
         2770                    2780              2790 ...

... VAL LYS SER ASP GLY SER THR ASP LYS THR
                    ... G T T A A A T C T G A T G G T T C T A C G G A T A A A A C A
                              2800                    2810                    2820

GLN VAL VAL GLU GLU ALA LYS VAL SER THR ...
C A G G T G G T C G A A G A A G C T A A A G T T T C T A C C ...
         2830                    2840              2850 ...

... ASP GLU LYS HIS VAL VAL SER LEU ASP PRO
                    ... G A T G A A A A A C A C G T T G T C A G C C T T G A T C C A
                              2860                    2870                    2880

ASN ASP GLN SER LYS GLY LYS GLY VAL VAL ...
A A T G A T C A A T C A A A A G G T A A A G G C G T G G T C ...
         2890                    2900              2910 ...

... ILE ASN ASN MET ALA ASN GLY GLU ILE SER
                    ... A T T A A C A A T A T G G C T A A T G G C G A A A T T T C T
                              2920                    2930                    2940
```

FIG.22O

ALA THR SER THR ASP ALA ILE ASN GLY SER....
GCCACTTCCACCGATGCGATTAACGGAAGT...
         2950                2960         2970...

GLN LEU TYR ALA VAL ALA LYS GLY VAL THR
              ...CAGTTGTATGCCGTGGCAAAAGGGGTAACA
                 ...           2980          2990        3000

ASN LEU ALA GLY GLN VAL ASN ASN LEU GLU....
AACCTTGCTGGACAAGTGAATAATCTTGAG...
         3010              3020           3030...

GLY LYS VAL ASN LYS VAL GLY LYS ARG ALA
              ...GGCAAAAGTGAATAAAGTGGGCAAACGTGCA
                 ...          3040           3050         3060

ASP ALA GLY THR ALA SER ALA LEU ALA ALA....
GATGCAGGTACTGCAAGTGCATTAGCGGCT...
         3070              3080          3090...

SER GLN LEU PRO GLN ALA THR MET PRO GLY
              ...TCACAGTTACCACAAGCCACTATGCCAGGT
                 ...          3100           3110         3120

LYS SER MET VAL SER ILE ALA GLY SER SER....
AAATCAATGGTTTCTATTGCGGGAAGTAGT...
         3130              3140          3150...

FIG.22P

```
              ...  TYR  GLN  GLY  GLN  ASN  GLY  LEU  ALA  ILE  GLY
              ...  T A T C A A G G T C A A A A T G G T T T A G C T A T C G G G
                                3160              3170              3180

VAL  SER  ARG  ILE  SER  ASP  ASN  GLY  LYS  VAL ...
G T A T C A A G A A T T T C C G A T A A T G G C A A A G T G ...
              3190              3200              3210

...  ILE  ILE  ARG  LEU  SER  GLY  THR  THR  ASN  SER
              ...  A T T A T T C G C T T G T C A G G C A C A A C C A A T A G T
                                3220              3230              3240

GLN  GLY  LYS  THR  GLY  VAL  ALA  ALA  GLY  VAL ...
C A A G G T A A A A C A G G C G T T G C A G C A G G T G T T ...
              3250              3260              3270

...  GLY  TYR  GLN  TRP  ***
              ...  G G T T A C C A G T G G T A A T A G A A T T C C G G A T C C
                                3280              3290              3300
```

FIG.23A

NTHi strain K22 Hia

```
          MET ASN LYS ILE PHE ASN...
GCGAATTCATATGAACAAAATTTTTAA...
                10              20

VAL ILE TRP ASN VAL VAL THR GLN THR TRP VAL
...CGTTATTTGGAATGTTGTGACTCAAACTTGGGT
          30              40              50              60

VAL VAL SER GLU LEU THR ARG ALA HIS...
TGTCGTATCTGAACTCACTCGCGCCCA...
          70              80

THR LYS CYS ALA SER ALA THR VAL ALA VAL ALA
...CACCAAAATGCGCCCTCCGCCACCGTGGCGGTTGC
          90             100             110             120

VAL LEU ALA THR ALA LEU SER ALA THR...
CGTATTGGCAACTGCCGTTGTCTGCAAC...
         130             140

ALA GLU ALA ASN ASN ASN THR SER VAL THR ASN
...GGCTGAAGCGAACAACAATACTTCTGTTACGAA
        150             160             170             180
```

FIG.23B

```
GLY LEU ASN ALA TYR GLY ASP THR ASN...
TGGGTTGAATGCTTATGGCGATACTAA...
          190                200                                  ...TTTAATACAACCAATAATTCGATAGCAGATTT
                                                                                220                 230                240

PHE ASN THR THR ASN ASN SER ILE ALA ASP LEU

GLU LYS HIS VAL GLN ASP ALA TYR LYS....
GGAAAAACACGTTCAAGATGCTTATAA....                  ...AGGCTTATTAAATCTGAATGAAAAGATACAAA
           250                260                        270            280            290            300

GLY LEU LEU ASN LEU ASN GLU LYS ASP THR ASN

LYS SER SER PHE LEU VAL ALA ASP ASN...
TAAGTCAAGTTTCTTGGTTGCCGACAA...                   ...TACCGCCCGCAACCGTAGGCAATTTGCGTAAATT
           310            320                        330            340            350            360

THR ALA ALA THR VAL GLY ASN LEU ARG LYS LEU

GLY TRP VAL LEU SER SER LYS ASN GLY....
GGGCTGGGTATTGTCTAGCAAAAACGG....
           370            380
```

FIG.23C

```
                                    THR ARG ASN GLU LYS SER TYR GLN VAL LYS GLN
                                ...C A C A A G G A A C G A G A A A A G C T A T C A A G T A A A A C A
                                ...     390                    400                   410                  420

ALA ASP GLU VAL LEU PHE THR GLY SER...       GLY ALA ALA THR VAL SER SER SER LYS ASP
A G C T G A T G A A G T T C T C T T T A C T G G A T C...  T G G T G C T G C A A C G G T T A G T T C C A G C T C T A A A G A
               430                  440                         450                   460                   470                  480

GLY LYS HIS THR ILE THR ILE SER VAL...        THR LYS GLY SER PHE ALA GLU VAL LYS THR ASP
C G G T A A A C A T T A C C A T T T C T G T...   T A C C A A A G G T A G T T T T G C T G A G G T A A A A A C T G A
              490                   500                            510                  520                   530                   540

ALA THR GLY GLY GLN VAL ASN ALA...        ASP ARG GLY LYS VAL LYS ALA GLU ASP GLU ASN
T G C A A C T A C T G G A G G T C A A G T A A A C G C...   C G A C C G T G G T A A A G T G A A A G C T G A G G A C G A G A A
             550                   560                            570                   580                    590                  600
```

FIG.23D

```
GLY ALA ASP VAL ASP LYS LYS VAL ALA...        THR VAL LYS ASP VAL ALA LYS ALA ILE ASN ASP
TGGAGCTGATGTTGATAAGAAAGTTGC...     ...AACTGTAAAAGATGTTGCTAAGGCGATTAACGA
            610                              630                    650                660
                      620                                   640

ALA ALA THR PHE VAL LYS VAL GLU SER...        THR ASP ASP ILE GLU ASN GLY ALA ALA GLY
TGCCCGCAACTTTCGTGAAAGTGGAAAG...     ...CACAGATGATGACATTGAAAATGGTGCTGCAGG
            670                              690                    710                720
                      680                                   700

LYS ASN GLU THR THR ASP GLN ALA LEU...        LYS ALA GLY ASP THR LEU LYS ALA GLY
CAAAAATGAAACTACAGACCAAGCTCT...      ...CAAAGCAGGCGACACCTTAAAAGCGGG
            730                              750                    770                780
                      740                                   760

LYS ASN LEU LYS ALA LYS LEU ASP GLN...
TAAAAACTTAAAAGCTAAGTTAGACCA
            790
                      800
```

FIG.23E

```
                              ASN GLY LYS SER VAL THR PHE ALA LEU ALA LYS
                           ...AAATGGTAAATCAGTAACCTTTGCTTTAGCGAA
                           ...   810            820            830            840

ASP LEU ASP VAL THR SER ALA LYS VAL...
AGACCTTGATGTGACCCTCTGCGAAAGT...
   850                    860

SER ASP LYS LEU SER ILE GLY LYS ASP THR ASN
                           ...GAGTGATAAGTTGTCTATTGGTAAAGATACGAA
                           ...   870            880            890            900

LYS VAL ASP ILE THR SER ASP ALA ASN...
TAAAGTTGATATTACCAGTGATGCAAA...
   910                    920

GLY LEU LYS LEU ALA LYS THR GLY ASN GLY ASN
                           ...TGGCTTGAAATTGGCGAAAACAGGTAACGGAAA
                           ...   930            940            950            960

GLY GLN ASN GLY ASN VAL HIS LEU ASN...
TGGTCAAAACGGTAATGTCCACTTAAA...
   970                    980

GLY ILE ALA SER THR LEU THR ASP THR ILE THR
                           ...TGGTATTGCTTCGACTTTGACCGATACCATTAC
                           ...   990           1000           1010           1020
```

FIG.23F

GLY MET THR GLN ALA SER ASN GLY... ... VAL ALA VAL GLN ASN HIS ASN ARG ALA ALA SER
AGGTATGACAACACAAGCAATGG... ...CGTGGCTGTGTGCAGAATCATAATCGTGCTGCGAG
            1030                                  1040           1050            1060               1070                 1080

VAL ALA ASP VAL LEU ASN ALA GLY TRP... ...ASN ILE GLN GLY ASN GLY ALA SER VAL ASP PHE
TGTGGCTGATGTATTAAATGCAGGCTG... ...GAATATTCAAGGCAACGGAGCGAGCGTTGATTT
              1090                      1100              1110             1120                   1130             1140

VAL ASN ALA TYR ASP THR VAL ASP PHE... ...VAL ASN GLY THR ASN THR ASN VAL ASN VAL THR
TGTCAATGCTTACGACACAGTAGATTT... ...TGTCAATGGTACAAACACCAATGTGAACGTTAC
              1150                      1160              1170             1180                   1190             1200

THR ASP THR ALA HIS LYS LYS THR THR...
GACTGATACGGCTCACAAAAGACAAC...
              1210                      1220

FIG. 23G

```
                              VAL ARG VAL ASP VAL THR GLY LEU PRO VAL GLN
                           ...CGTCCGTGTGGATGTAACAGGCTTGCCGGTTCA
                           ...1230              1240              1250              1260

TYR VAL THR GLU ASP GLY LYS THR VAL...         VAL LYS VAL ASP ASN LYS TYR TYR GLU ALA LYS
ATATGTTACGGAAGACGGCAAAACCGT...                ...TGTGAAAGTGGACAATAAGTATTACGAAGCTAA
              1270              1280           ...1290              1300              1310              1320

GLN ASP GLY SER ALA ASP MET ASP LYS...         LYS VAL GLU ASN GLY LEU ALA LYS THR LYS
GCAAGACGGGTTCGGCGGATATGGATAA...               ...AAAAGTCGAAAATGGCGAGCTGGCGAAAACCAA
              1330              1340           ...1350              1360              1370              1380

VAL LYS LEU VAL SER ALA SER GLY GLN....        ASN PRO VAL LYS ILE SER ASN VAL ALA GLU GLY
AGTGAAATTGGTGGTGTCGGCAAGCGGTCA....            ...AAATCCGGTGAAAATCAGCAATGTTGCGGAAGG
              1390              1400           ...1410              1420              1430              1440
```

FIG.23H

THR GLU ASN ASP ALA VAL SER PHE...
CACGGAAGAAAACGATGCGGGTCAGCTT...
        1450                        1460

...LYS GLN LEU LYS ALA LEU GLN GLU LYS GLN VAL
...TAAGCAAATTGAAAGCCTTGCAAGAGAAACAGGT
        1470                        1480                        1490                        1500

THR LEU THR ALA SER ASN ALA TYR ALA...
TACTTTAACTGCGAGCAATGCTTATGC...
        1510                        1520

...ASN GLY GLY ASN ASP ALA ASP GLY LYS ALA
...CAATGGTGGTAACGATGCCGACGGCGCAAGGC
        1530                        1540                        1550                        1560

THR GLN THR LEU ASN ASN GLY LEU ASN...
AACTCAAACTTTAAACAATGGTTTGAA...
        1570                        1580

...PHE LYS PHE LYS SER THR ASP GLY GLU LEU LEU
...TTTTAAATTTAAATCCACAGACGGCGAGTTTGTT
        1590                        1600                        1610                        1620

ASN ILE LYS VAL GLU ASN ASP THR VAL...
GAACATCAAAGTAGAAAATGACACAGT...
        1630                        1640

FIG.23I

```
                              THR PHE THR PRO LYS LYS GLY SER VAL GLN VAL
                          ...TACCTTTACGCCGAAAAAAGGTTCGGTACAGGT
                          ...1650              1660              1670              1680

GLY GLU ASP GLY LYS ALA THR ILE GLN...
TGGCGAAGACGGTAAGGCTACGATTCA...
              1690              1700

ASN GLY THR LYS THR THR ASP GLY LEU VAL GLU
                          ...AAATGGTACGAAACAACCGACGGTTTGGTTGA
                          ...1710              1720              1730              1740

ALA SER GLU LEU VAL GLU SER LEU ASN...
AGCTTCCGAATTGGTTGAAAAGCCCTGAA...
              1750              1760

LYS LEU GLY TRP LYS VAL GLY VAL ASP LYS ASP
                          ...CAAACTTGGGCTGGAAAGTGGGCGTTGATAAAGA
                          ...1770              1780              1790              1800

GLY SER GLY GLU LEU ASP GLY ALA SER...
CGGCAGCGGCGAGCTTGATGGTGCATC...
              1810              1820

ASN GLU THR LEU VAL LYS SER GLY ASP LYS VAL
                          ...CAATGAAACTTTAGTGAAGTCGGGCGATAAAGT
                          ...1830              1840              1850              1860
```

FIG.23J

THR LEU LYS ALA GLY GLU ASN LEU LYS...
AACTTTGAAAGCCGGGCGAGAATCTGAA...
                               1870

VAL LYS GLN ASP GLY THR ASN PHE THR TYR ALA
                    ...GGTCAAACAAGACGGCACAAACTTCACTTACGC
                       1880        1890        1900        1910        1920

LEU LYS ASP GLU LEU THR GLY VAL LYS...
GCTCAAAGATGAATTGACGGGCGTGAA...
                               1930

SER VAL GLU PHE LYS ASP THR ALA ASN GLY SER
                    ...GAGCGTGGAGTTTAAAGACACGGCGAATGGTTC
                       1940        1950        1960        1970        1980

ASN GLY ALA ALA SER THR LYS ILE THR LYS...
AAACGGGTGCAAGCACGAAGATTACCAA...
                               1990        2000

ASP GLY LEU THR ILE THR SER ALA ASN GLY ALA
                    ...AGACGGGCTTGACCATTACGTCGGCAAACGGGTGC
                       2010        2020        2030        2040

ASN GLY ALA ALA THR ASP ALA ASP...
GAATGGTGCCGGCGGCGACTGATGCGGA...
                       2050        2060

FIG.23K

```
                    LYS ILE LYS VAL ALA SER ASP GLY ILE SER ALA
              ...CAAGATTAAAGTGGCTTCAGACGGCATCAGTGC
                 ...2070                    2080                    2090                    2100

GLY ASN LYS ALA VAL LYS ASN VAL VAL...          SER GLY LEU LYS LYS PHE GLY ASP ALA ASN PHE
GGGTAATAAAGCGGGTTAAAAACGTTGT...              ...GAGCGGGACTGAAGAAATTTGGTGATGCGAATTT
              2110                    2120                              2130                    2140                    2150                    2160

ASN PRO LEU THR SER SER ALA ASP ASN...          LEU THR LYS GLN TYR ASP ASP ALA TYR LYS GLY
CAATCCCACTGACCAGTTCCGCCGACAA...              ...CTTAACGAAACAATATGACGATGCCTATAAAAGG
              2170                    2180                              2190                    2200                    2210                    2220

LEU THR ASN LEU ASP GLU LYS GLY ALA...          ASP LYS GLN THR LEU THR VAL ALA ASP ASN THR
CTTGACCAATTTGGATGAAAAAGGTGC...              ...GGACAAGCAAACTCTGACTGTTGCCGACAATAC
              2230                    2240                              2250                    2260                    2270                    2280
```

FIG.23L

```
ALA ALA THR VAL GLY ASP LEU ARG GLY...                                           LEU GLY TRP VAL ILE SER ALA ASP LYS THR THR
TGCCGCAACCGTGGGCGATTTGCGCGG...                                                ...CTTGGGCTGGGGTCATTTCTGCGGACAAAACCAC
              2290                    2300                                              ...2310                2320                2330              2340

GLY GLU LEU ASN LYS GLU TYR ASN ALA...                                           GLN VAL ARG ASN ALA ASN GLU VAL LYS PHE LYS
AGGCGAACTCAATAAGGAATACAACGC...                                                ...GCAAGTGCGTAACGCCAATGAAGTGAAATTCAA
              2350                    2360                                              ...2370                2380                2390              2400

SER GLY ASN GLY ILE HIS VAL SER GLY...                                           LYS THR VAL ASN GLY ARG ARG GLU ILE THR PHE
GAGCGGGCAACGGGTATCCATGTTTCCGG...                                              ...TAAAACGGTCAACGGTAGGCGCGAATTACTTT
              2410                    2420                                              ...2430                2440                2450              2460

GLU LEU ALA LYS ASP GLU ASN ALA ILE...
TGAATTGGCTAAAGACGAAAATGCCAT...
              2470                    2480                                              ...
```

FIG.23M

```
                             ALA PHE GLY TYR GLY SER LYS ALA LEU ARG ASP
                         ...TGCTTTCGGTTATGGCTCAAAAGCCCTTGCGCGA
                         ...                              2510          2520
                            2490

ASN THR VAL ALA ILE GLY THR GLY ASN...
TAACACGGGTGGCAATTGGTACGGGCAA....
                     2530                2540
                   VAL VAL ASN ALA GLU LYS SER GLY ALA PHE GLY
              ...CGTTGTGAATGCGGAAAAATCTGGTGCATTCGG
              ...                        2560                  2570           2580
                 2550

ASP PRO ASN TYR ILE GLU ASP LYS ALA....
CGATCCGAACTACATCGAAGATAAAGC....
                2590                2600
                     GLY GLY SER TYR ALA PHE GLY ASN ASP ASN ARG
                ...CGGTGGCAGCTACGCTTTCGGTAACGATAACCG
                ...                        2620                 2630             2640
                    2610

ILE THR SER LYS ASN THR PHE VAL LEU....
TATTACTTCTAAAAACACTTTTGTGTT....
                2650                2660
                    GLY ASN GLY VAL ASN ALA LYS TYR LYS ALA ASN
                ...GGGTAATGGAGTTAATGCGAAATATAAAGCCAA
                ...                       2680                  2690            2700
                   2670
```

FIG.23N

GLY ASP VAL ASP THR GLU THR VAL THR...
TGGAGATGTTGATACGGAAACCGTAAC...
 2710                    2720         ...2730

VAL LYS ASP LYS ASP GLY LYS GLU THR THR VAL
                        ...CGTTAAAGGACAAAGACGGTAAAGAGACTACCGT
                            2740                 2750             2760

THR VAL PRO LYS ALA LEU GLY ALA THR...
TACTGTTCCTAAAGCGTTAGGGGCTAC...
        2770                  2780  ...2790

VAL GLU ASN SER VAL TYR LEU GLY ASN LYS SER
                        ...GGTTGAAAACTCCGTTTATTTGGGTAATAAATC
                            2800                 2810             2820

THR ALA THR LYS ASP LYS GLY LYS ASN...
GACTGCGACAAAAGATAAGGGTAAAAA...
        2830                  2840  ...2850

LEU LYS SER ASP GLY THR ALA GLY ASN THR THR
                        ...CCTGAAATCTGATGGTACGGCGGGTAACACTAC
                            2860                 2870             2880

THR ALA GLY THR THR GLY THR VAL ASN...
AACTGCTGGCACAAACGGGTACGGTAAA...
        2890                  2900

FIG. 230

```
            ... GLY PHE ALA GLY ALA THR ALA HIS GLY ALA VAL
            ...CGGCTTTGCCGGTGCAAACGGCGCACGGTGCGGT
            ...2910              2920              2930              2940

SER VAL GLY ALA SER GLY GLU GLU ARG...
TTCTGTCGGGCGCAAGCGGGCGAAGAAAG...
           2950              2960

... ARG ILE GLN ASN VAL ALA ALA GLY GLU ILE SER
            ...ACGTATCCAAAACGTCGCGGCCAGGCGAAATTTC
            ...2970              2980              2990              3000

ALA THR SER THR ASP ALA ILE ASN GLY...
CGCCACTTCCACCGATGCGATTAACGG...
            3010              3020

... SER GLN LEU TYR ALA VAL ALA LYS GLY VAL THR
            ...CAGCCAGTTGTATGCTGTGGCAAAAGGGGTAAC
            ...3030              3040              3050              3060

ASN LEU ALA GLY GLN VAL ASN LYS VAL...
AAATCTTGCTGGACAAGTGAATAAAGT...
            3070              3080

... GLY LYS ARG ALA ASP ALA GLY THR ALA SER ALA
            ...GGGCAAACGTGCAGATGCAGGTACAGCAAGTGC
            ...3090              3100              3110              3120
```

FIG.23P

```
LEU ALA ALA SER GLN LEU PRO GLN ALA...
ATTAGCAGCTTCACAGTTACCACAAGC...
         3130                ...3140
                                        SER MET PRO GLY LYS SER MET VAL SER ILE ALA
                                    ...CTCTATGCCAGGTAAATCAAATGGTTTCTATTGC
                                        ...3150              3160              3170              3180

GLY SER SER TYR GLN GLY GLN ASN GLY...
GGGAAGTAGTTATCAAGGTCAAAATGG
      3190              3200
                                        LEU ALA ILE GLY VAL SER ARG ILE SER ASP ASN
                                    ...TTTAGCTATCGGGGTATCACGAATTTCCGATAA
                                        ...3210              3220              3230              3240

GLY LYS VAL ILE ILE ARG LEU SER GLY...
TGGCAAAGTGATTATTCGCTTGTCAGG
      3250              3260
                                        THR THR ASN SER GLN GLY LYS THR GLY VAL ALA
                                    ...CACAACCAATAGCCAAGGTAAAACAGGCGTTGC
                                        ...3270              3280              3290              3300

ALA GLY VAL GLY TYR GLN TRP ***
AGCAGGTGTTGGTTACCCAGTGGTAATA...                                    ...GAATTGATCCGC
      3310              3320                                           ...3330
```

FIG.24A

*H. influenzae* type c strain API *hia* sequence

```
MET ASN LYS ILE PHE ASN VAL ILE TRP ASN ...
A T G A A C A A A A T T T T T A A C G T T A T T T G G A A T...
                10            20            30...
                              ... VAL MET THR GLN THR TRP VAL VAL VAL SER
                              ... G T T A T G A C T C A A A C T T G G G T T G T C G T A T C T
                              ...              40            50            60

GLU LEU THR ARG THR HIS THR LYS ARG ALA ...
G A A C T C A C T C G C A C C C A C A C C A A A C G C G C C...
                70            80            90...
                              ... SER ALA THR VAL GLU THR ALA VAL LEU ALA
                              ... T C C G C A A C C G T G G A G A C C G C C G T A T T G G C G
                              ...              100           110           120

THR LEU LEU PHE ALA THR VAL GLN ALA ASN ...
A C A C T G T T G T T T G C A A C G G T T C A G G C G A A T...
                130           140           150...
                              ... ALA THR ASP GLU ASP GLU GLU LEU ASP PRO
                              ... G C T A C C G A T G A A G A T G A A G A G T T A G A C C C C
                              ...              160           170           180

VAL VAL ARG THR ALA PRO VAL LEU SER PHE ...
G T A G T A C G C A C T G C T C C C G T G T T G A G C T T C...
                190           200           210...
```

FIG.24B

```
                                   ... HIS SER ASP LYS GLU GLY THR GLY GLU LYS
                                   ... C A T T C C G A T A A A G A A G G C A C G G G G A G A A A A A
                                                                                                240
                                                           ...
GLU VAL THR GLU ASN SER ASN TRP GLY ILE ...         TYR PHE HIS ASN LYS GLY VAL LEU LYS ALA
G A A G T T A C A G A A A A T T C A A A T T G G G G A A T A ... T A T T T C C A C A A T A A A G G A G T A C T A A A A G C C
                          250                   260          ...                   280                   300
                                                270 ...
GLY ALA ILE THR LEU LYS ALA GLY ASP ASN ...         LEU LYS ILE LYS GLN SER THR ASN ALA SER
G G A G C A A T C A C C C T C A A A G C C G G C G A C A A A C ... C T G A A A A T C A A A C A A A G C A C C A A T G C C A G T
                          310                   320          ...                   340                   360
                                                330 ...                                      350
SER PHE THR TYR SER LEU LYS LYS ASP LEU ...         THR ASP LEU THR SER VAL ALA THR GLU LYS
A G C T T C A C C T A C T C G C T G A A A A A G A C C T C ... A C A G A T C T G A C C A G T G T T G C A A C T G A A A A A
                          370                   380          ...                   400                   420
                                                390 ...                                      410
                                                             ...
```

FIG.24C

LEU SER PHE GLY ALA ASN GLY ASP LYS VAL...
TTATCGTTTGGCGCAAACGGCGATAAAGTT...
          430              440              450...

...ASP ILE THR SER ASP ALA ASN GLY LEU LYS
         ...GATATTACCAGTGATGCAAATGGCTTGAAA
                    460              470              480

LEU ALA LYS THR GLY ASN VAL HIS...
TTGGCGAAAACAGGTAACGGAAATGTTCAT...
          490              500              510...

...LEU ASN GLY LEU ASP SER THR LEU PRO ASP
         ...TTGAATGGTTTGGATTCAACTTTGCCTGAT
                    520              530              540

ALA VAL THR ASN THR GLY VAL LEU SER SER...
GCGGTAACGAATACAGGTGTGTTAAGTTCA...
          550              560              570...

...SER SER PHE THR PRO ASN ASP VAL GLU LYS
         ...TCAAGTTTTACACCTAATGATGTTGAAAAA
                    580              590              600

THR ARG ALA ALA THR VAL LYS ASP VAL LEU...
ACAAGAGCTGCAACTGTTAAAGATGTTTTA...
          610              620              630

FIG.24D

```
                         ASN ALA GLY TRP ASN ILE LYS GLY ALA LYS
                      ...AATGCAGGTTGGAACATTAAAGGTGCTAAA A
                      ...            640         650          660

THR ALA GLY GLY ASN VAL GLU SER VAL ASP...
ACTGCTGGAGGTAATGTTGAGAGTGTTGAT...
            670             680      690...

LEU VAL SER ALA TYR ASN ASN VAL GLU PHE
                      ...TTAGTGTCCGCTTATAATAATGTTGAATT T
                      ...            700         710          720

ILE THR GLY ASP LYS ASN THR LEU ASP VAL....
ATTACAGGCGATAAAAACACGCTTGATGTT....
            730             740      750...

VAL LEU THR ALA LYS GLU ASN GLY LYS THR
                      ...GTATTAACAGCTAAAGAAAACGGTAAAAC A
                      ...            760         770          780

THR GLU VAL LYS PHE THR PRO LYS THR SER....
ACCGAAGTGAAATTCACACCGAAAACCTCT....
            790             800      810...

VAL ILE LYS GLU LYS ASP GLY LYS LEU PHE
                      ...GTTATCAAAGAAAAAGACGGTAAGTTATT T
                      ...            820         830          840
```

FIG.24E

```
THR GLY LYS GLU ASN ASP THR ASN LYS ....
ACTGGAAAAGAGAATAACGACACAAATAAA....
         850              860          870....
                    ... VAL THR SER ASN THR ALA THR ASP ASN THR
                    ...GTTACAAGTAACACGGCGACTGATAAATACA
                              880           890            900

ASP GLU GLY ASN GLY LEU VAL THR ALA LYS ....
GATGAGGGTAATGGCTTAGTCACTGCAAAA....
          910             920          930....
                    ... ALA VAL ILE ASP ALA VAL ASN LYS ALA GLY
                    ...GCTGTGATTGATGCTGTGAACAAGGCTGGT
                              940           950            960

TRP ARG VAL LYS THR THR ALA ASN GLY ....
TGGAGAGTTAAAACTACTGCTAATGGT....
          970             980          990....
                    ... GLN ASN GLY ASP PHE ALA THR VAL ALA SER
                    ...CAAAATGGCGACTTCGCAACTGTTGCGTCA
                              1000          1010           1020

GLY THR ASN VAL THR PHE GLU SER GLY ASP ....
GGCACAAATGTAACCTTTGAAAGTGGCGAT....
          1030            1040         1050....
```

FIG.24F

```
                            ... GLY THR THR ALA SER VAL THR LYS ASP THR
                            ...GGTACAACAGCGTCAGTAAACTAAAGATACT
                                    1060          1070          1080

ASN GLY ASN GLY ILE THR VAL LYS TYR ASP ...
AACGGGCAATGGCATCACTGTTAAGTACGAC...
        1090          1100

... ALA LYS VAL GLY ASP GLY LEU LYS PHE ASP
                            ...GCGAAAGTTGGCGACGGCTTGAAATTTGAT
                                    1120          1130          1140

SER ASP LYS LYS ILE VAL ALA ASP THR THR ...
AGCGATAAAAAAATCGTTGCAGATACGACC...
        1150          1160          1170

... ALA LEU THR VAL THR GLY GLY LYS VAL ALA
                            ...GCACTTACTGTGACAGGTGGTAAGGTAGCT
                                    1180          1190          1200

GLU ILE ALA LYS GLU ASP ASP LYS LYS ...
GAAATTGCTAAAGAAGATGACAAGAAAAAA...
        1210          1220          1230

... LEU VAL ASN ALA GLY ASP LEU VAL THR ALA
                            ...CTTGTTAATGCAGGCGATTTGGTAACAGCT
                                    1240          1250          1260
```

FIG.24G

```
LEU GLY ASN LEU SER TRP LYS ALA LYS ALA                      ASP THR ASP GLY ALA LEU
TTAGGTAATCTAAGTTGGAAAGCAAAAGCT...     ...GAGGCTGATACTGATGGTGCGCTT
            1270              1280                     1290...       1300          1310          1320

GLU GLY ILE SER LYS ASP GLN GLU VAL LYS                       VAL THR PHE LYS ALA GLY
GAGGGGATTTCAAAAGACCAAGAAGTCAAA...     ...GCAGGCGAAACGGTAACCTTTAAAGCGGGC
            1330              1340                    1350...       1360          1370          1380

LYS ASN LEU LYS VAL LYS GLN ASP GLY ALA                       TYR SER LEU GLN ASP ALA LEU
AAGAACTTAAAAGTGAAACAGGATGGTGCG...     ...AACTTTACTTATTCACTGCAAGATGCTTTA
            1390              1400                     1410...       1420          1430          1440

THR GLY LEU THR SER ILE THR LEU GLY GLY
ACGGGTTTAACGAGCATTACTTTAGGTGGT...
            1450              1460          1470
```

FIG.24H

```
                              ...  THR  THR  ASN  GLY  GLY  ASN  ASP  ALA  LYS  THR
                              ...  A C A A A C T A A T G G C G G A A A T G A T G C G A A A A C C
                                                            1480                      1490                      1500

VAL  ILE  ASN  LYS  ASP  GLY  LEU  THR  ILE  THR  ...                ...  PRO  ALA  GLY  ASN  GLY  GLY  THR  THR  GLY  THR
G T C A T C A A A G A C G G T T T A A C C A T C A C G ...            ... C C A G C A G G T A A T G G C G G T A C G A C A G G T A C A
                    1510                      1520                1530                      1540                      1550                      1560

ASN  THR  ILE  SER  VAL  THR  LYS  ASP  GLY  ILE  ...                ...  LYS  ALA  GLY  ASN  LYS  ALA  ILE  THR  ASN  VAL
A A C A C C A T C A G C G T A A C C A A A G A T G G C A T T ...      ... A A A G C A G G T A A T A A A G C T A T T A C T A A T G T T
                    1570                      1580                1590                      1600                      1610                      1620

ALA  SER  GLY  LEU  ARG  ALA  TYR  ASP  ASP  ALA  ...                ...  ASN  PHE  ASP  VAL  LEU  ASN  ASN  SER  ALA  THR
G C G A G T G G T T T A A G A G C T T A T G A C G A T G C G ...      ... A A T T T T G A T G T T T T A A A T A A C T C T G C A A C T
                    1630                      1640                1650                      1660                      1670                      1680
```

FIG. 24I

```
ASP LEU ASN ARG HIS VAL GLU ASP ALA TYR ....
GATTTAAATAGACACGTTGAAGATGCTTAT...
         1690              1700         1710....
                                                      ...LYS GLY LEU LEU ASN LEU ASN GLU LYS ASN
                                                      ...AAAGGTTTATTAAATCTAAATGAAAAAAT
                                                              1720         1730         1740

ALA ASN LYS GLN PRO LEU VAL THR ASP SER ....
GCAAATAAACAAACCGTTGGTGACTGACAGC...
         1750              1760         1770....
                                                      ...THR ALA ALA THR VAL GLY ASP LEU ARG LYS
                                                      ...ACGGGCGGCGACTGTAGGCGATTTACGTAAA
                                                              1780         1790         1800

LEU GLY TRP VAL VAL SER THR LYS ASN GLY ....
TTGGGTTGGGTAGTATCAACCAAAAACGGT...
         1810              1820         1830....
                                                      ...THR LYS GLU GLU LYS SER ASN GLN VAL LYS GLN
                                                      ...ACGAAAGAAGAAAAGCAATCAAGTTAAACAA
                                                              1840         1850         1860

ALA ASP GLU VAL LEU PHE THR GLY ALA GLY ....
GCTGATGAAGTCCTCTTTACCGGAGCCCGGT...
         1870              1880         1890....
```

FIG.24J

```
                                        ... ALA ALA THR VAL THR SER LYS SER GLU ASN
                                        ... GCTGCTACGGGTTACTTCCAAATCTGAAAAC
                                                                       1900               1910               1920

GLY LYS HIS THR ILE THR VAL SER VAL ALA ...         ... GLU THR LYS ALA ASP SER GLY LEU GLU LYS
GGTAAACATACGATTACCGTTAGTGTGGCT...                   ...GAAACTAAAGCGGATAGCGGGTCTTGAAAAA
                  1930               1940  1950                       1960               1970               1980

ASP GLY ASP THR ILE LYS LEU LYS VAL ASP ...         ... ASN GLN ASN THR ASP ASN VAL LEU THR VAL
GATGGCGATACTATTAAGCTCAAAGTGGAT...                   ...AATCAAAACACTGATAATGTTTTAACTGTT
                  1990               2000  2010                       2020               2030               2040

GLY ASN ASN GLY THR ALA VAL THR LYS GLY ...         ... GLY PHE GLU THR VAL LYS THR GLY ALA THR
GGTAATAATGGTACTGCTGTCACTAAAGGT...                   ...GGCTTTGAAACTGTTAAAACTGGAGCGACT
                  2050               2060  2070                       2080               2090               2100
```

FIG. 24K

ASP ALA ASP ARG GLY LYS VAL THR VAL LYS ....
GATGCAGATCGCGGGTAAAGTAACTGTAAAA....
         2110                    2120             2130....

.... ASP ALA THR ALA ASN ASP ALA ASP LYS LYS
   ....GATGCTACTGCTAATGACGCTGATAAGAAA
   ....              2140             2150             2160

VAL ALA THR VAL LYS ASP VAL ALA THR ALA ....
GTCGCAACTGTAAAAGATGTTGCAACCGCA....
         2170                    2180             2190....

.... ILE ASN SER ALA ALA THR PHE VAL LYS THR
   ....ATTAATAGTGCGGCGACTTTTGTGAAAACA
   ....              2200             2210             2220

GLU ASN LEU THR THR SER ILE ASP GLU ASP ....
GAGAATTTAACTACCTCTATTGATGAAGAT....
         2230                    2240             2250....

.... ASN PRO THR ASP ASN GLY LYS ASP ASP ALA
   ....AATCCTACAGATAACGGCAAAGATGACGCA
   ....              2260             2270             2280

LEU LYS ALA GLY ASP THR LEU THR PHE LYS ....
CTTAAAGCGGGCGATACCCTTAACCTTTAAA....
         2290                    2300             2310....

FIG. 24L

```
                            ... ALA GLY LYS ASN LEU LYS VAL LYS ARG ASP
                            ... G C A G G T A A A A C C T G A A A G T A A A C G T G A T
                            ...                          2320                 2330                 2340

GLY LYS ASN ILE THR PHE ASP LEU ALA LYS ....
G G A A A A A A T A T T A C T T T T G A C T T G G C G A A A ....
               2350                 2360                 2370....

... ASN LEU GLU VAL LYS THR ALA LYS VAL SER
                            ... A A C C T T G A G G T G A A A A C T G C G A A A G T G A G T
                            ...                          2380                 2390                 2400

ASP THR LEU THR ILE GLY GLY ASN THR PRO ....
G A T A C T T T A A C G A T T G G C G G G A A T A C A C C T ....
               2410                 2420                 2430....

... THR GLY GLY THR THR ALA THR PRO LYS VAL
                            ... A C A G G T G G C A C T A C T G C G A C G C C A A A A G T G
                            ...                          2440                 2450                 2460

ASP THR SER THR ALA ASP GLY LEU ASN ....
A A T A T T A C T A G C A C G G G C T G A T G G T T T G A A T ....
               2470                 2480                 2490....

... PHE ALA LYS THR GLU THR ALA ASP ALA SER GLY
                            ... T T T G C A A A A A C A G A A A C A G C C G A T G C C T C G G G T
                            ...                          2500                 2510                 2520
```

FIG.24M

```
SER  LYS  ASN  VAL  TYR  LEU  LYS  GLY  ILE  ALA ...
TCT AAG AAT GTT TAT TTG AAA GGT ATT GCG ...
                              2540           2550...
                                  THR  THR  LEU  THR  GLU  PRO  SER  ALA  GLY  ALA
                                 ...ACA AAC TTT AAC TGA GCC AAG CCG CGG GGA GCG
                                             2560              2570              2580

LYS  SER  SER  HIS  VAL  LEU  ASP  LEU  ASN  VAL  ASP ...
AAG TCT TTC ACA CGT TGA TTT AAA TGT GGA T ...
                2590              2600              2610...
                                     ALA  THR  LYS  SER  LYS  SER  ASN  ALA  ALA  SER  ILE
                                    ...GCG ACG AAA AAT CCA ATG CAG CAA GTA TT
                                             2620              2630              2640

GLU  ASP  VAL  LEU  ARG  ALA  GLY  TRP  ASN  ILE ...
GAA GAT GTA TTG CGC GCA GGT TGG AAT ATT ...
                2650              2660              2670...
                                     GLN  GLY  ASN  GLY  ASN  ASN  VAL  ASP  TYR  VAL
                                    ...CAA GGT AAT GGT AAT AAT GTT GAT TAT GTA
                                             2680              2690              2700

ALA  THR  TYR  ASP  THR  VAL  ASN  PHE  THR  ASP ...
GCG ACG TAT GAC ACA GTA AAC TTT ACC GAT ...
                2710              2720              2730...
```

FIG.24N

```
      ... ASP SER  GLY  THR  THR  THR  VAL  THR  VAL
      ... GACAGCACAGGTACAACAACGGTAACCGTA
                              2750            2760
      ...
THR GLN LYS ALA ASP GLY LYS GLY ALA ASP ....
ACCCAAAAAGCAGATGGCAAAGGTGCTGAC....
            2770              2780        2790....

... VAL LYS ILE GLY ALA LYS THR SER VAL ILE
      ... GTTAAAATCGGTGCGAAACTTCTGTTATC
                              2810            2820
      ...
LYS ASP HIS ASN GLY LYS LEU PHE THR GLY ....
AAAGACCACAACGGCAAACTGTTTACAGGC....
            2830              2840        2850....

... LYS ASP LEU LYS ASP ALA ASN ASN GLY ALA
      ... AAAGACCTGAAAGATGCGAATAATGGTGCA
                              2870            2880
      ...
THR VAL SER GLU ASP ASP GLY LYS ASP THR ....
ACCGTTAGTGAAGATGATGGCAAAGACACC....
            2890              2900        2910....

... GLY THR GLY LEU VAL THR ALA LYS THR VAL
      ... GGCACAGGCTTAGTTACTGCAAAAACTGTG
                              2930            2940
      ...
```

FIG. 24O

ILE ASP ALA VAL ASN LYS SER GLY TRP ARG ....
ATTGATGCAGTAAATAAAAGCGGTTGGAGG...
          2950              2960         2970....

... VAL THR GLY GLU GLY ALA THR ALA GLU THR
...GTAACCGGTGAGGGCGCGACTGCCGAAACC
         2980              2990              3000

GLY ALA THR ALA VAL ASN ALA GLY ASN ALA ....
GGTGCAACCGCCGTGAATGCGGGTAACGCT...
          3010              3020         3030....

... GLU THR VAL THR SER GLY THR SER VAL ASN
...GAAACCGTTACATCAGGCACGAGCGTGAAC
         3040              3050              3060

PHE LYS ASN GLY ASN ALA THR THR ALA THR ....
TTCAAAAACGGCAATGCGACCACAGCGACC...
          3070              3080         3090....

... VAL SER LYS ASP ASN GLY ASN ILE ASN VAL
...GTAAGCAAAGATAATGGCAACATCAATGTC
         3100              3110              3120

LYS TYR ASP VAL ASN VAL GLY ASP GLY LEU ....
AAATACGATGTAAATGTTGGTGACGGGCTTG...
          3130              3140         3150....

FIG.24P

```
            ... LYS ILE GLY ASP ASP LYS LYS ILE VAL ALA
            ...A A G A T T G G C G A T G A C A A A A A A T C G T T G C A
                                 3160                  3170              3180

ASP THR THR LEU THR VAL THR GLY GLY ...        ... LYS VAL SER PRO ALA GLY ALA ASN SER
G A C A C G A C C A C A C T T A C T G T A A C A G G T G G T...     ...A A G G T G T C T G T T C C C T G C T G G T G C T A A T A G T
            3190                  3200                                  3220                  3230              3240

VAL ASN ASN LYS LYS LEU VAL ASN ALA ...        ... GLU GLY LEU ALA THR ALA LEU ASN ASN LEU
G T T A A T A A C A A T A A G A A A C T T G T T A A T G C A...     ...G A G G G T T T A G C G A C T G C T T T A A A C A A C C T A
            3250                  3260                                  3280                  3290              3300

SER TRP THR ALA LYS ALA ASP LYS TYR ALA ...    ... ASP GLY GLU SER GLU GLY GLU THR ASP GLN
A G C T G G A C G G C A A A A G C C G A T A A A T A T G C A...  ...G A T G G C G A G T C A G A G G G C G A A A C C G A C C A A
            3310                  3320                                  3340                  3350              3360
```

FIG.24Q

```
GLU VAL LYS ALA GLY ASP LYS VAL THR PHE....                    ASN LEU LYS VAL LYS GLN
GAAGTCAAAGCAGGCGACAAAGTAACCTTT...               ...AAAGCAGGCAAGAACTTAAAAGTGAAACAG
           3370              3380                        3400              3410         3420
                                            ...LYS ALA GLY LYS
                                                         3390...

SER GLU LYS ASP PHE THR TYR SER LEU GLN....                    GLY LEU THR SER ILE THR
TCTGAAAAAGACTTTACTTATTCACTGCAA...               ...GACACTTTAACAGGCTTAACGAGCATTACT
           3430              3440                        3460              3470         3480
                                            ...ASP THR LEU THR
                                                         3450...

LEU GLY GLY THR ALA ASN GLY ARG ASN ASP....                    ILE ASN LYS ASP GLY LEU
TTAGGTGGTACAGCTAATGGCAGAAATGAT...               ...ACGGGAACCGTCATCAACAAAGACGGCTTA
           3490              3500                        3520              3530         3540
                                            ...THR GLY THR VAL
                                                         3510...

THR ILE THR LEU ALA ASN GLY ALA ALA ALA....
ACCATCACGCTGGCAAATGGTGCTGCGGCA...
           3550              3560              3570
```

FIG.24R

```
                                    ... GLY THR ASP ALA SER ASN GLY ASN THR ILE
                                    ... GGCACAGATGCGTCTAACGGAAACACCATC
                                            3580              3590              3600

SER VAL THR LYS ASP GLY ILE SER ALA GLY ...
AGTGTAACCAAAGACGGCATTAGTGCGGGT...
        3610              3620              3630 ...

... ASN LYS GLU ILE THR ASN VAL LYS SER ALA
                                    ... AATAAAGAAATTACCAATGTTAAGAGTGCT
                                            3640              3650              3660

LEU LYS THR TYR LYS ASP THR GLN ASN THR ...
TTAAAAACCTATAAAGATACTCAAAACACT...
        3670              3680              3690 ...

... ALA GLY ALA THR GLN PRO ALA ALA ASN THR
                                    ... GCAGGTGCAACCTGCAACCTGGCTAATACA
                                            3700              3710              3720

ALA GLU VAL ALA LYS GLN ASP LEU VAL ASP ...
GCTGAAGTAGCCAAACAAGACTTGGTTGAT...
        3730              3740              3750 ...

... LEU THR LYS PRO ALA THR GLY ALA ALA GLY
                                    ... TTAACTAAACCTGCGACAGGTGCAGCTGGA
                                            3760              3770              3780
```

FIG.24S

ASN GLY ALA ASP ALA LYS ALA PRO ASP THR ....
AATGGTGCAGATGCAAAAAGCTCCCGATACC...
       3790                  3800
                    ... THR ALA ALA THR VAL GLY ASP LEU ARG GLY
                    ...ACAGCTGCAACCGTAGGCGACTTGCGTGGT
                          3810              3820              3830              3840

LEU GLY TRP VAL LEU SER ALA LYS LYS THR ....
TTGGGCTGGGTGCTTTCAGCTAAGAAAACT...
       3850                  3860
                    ... ALA ASP GLU THR GLN ASP LYS GLU PHE HIS
                    ...GCAGATGAAACACAAGATAAAGAGTTCCAC
                          3870              3880              3890              3900

ALA ALA VAL LYS ASN ALA ASN GLU VAL GLU ....
GCCGCCGTTAAAAACGCAAATGAAGTTGAG...
       3910                  3920
                    ... PHE VAL GLY LYS ASN GLY ALA THR VAL SER
                    ...TTCGTGGGTAAAAACGGTGCAACCGTGTCT
                          3930              3940              3950              3960

ALA LYS THR ASP ASN ASN GLY LYS HIS THR ....
GCAAAAACTGATAACAACGGAAAACATACT...
       3970                  3980                  3990

FIG.24T

```
                          ... VAL THR ILE ASP VAL ALA GLU ALA LYS VAL
                          ... G T A A C G A T T G A T G T T G C A G A A G C C A A A G T T
                                                   4000              4010             4020

GLY ASP GLY LEU GLU LYS ASP THR ASP GLY ...
G G T G A T G G T C T T T G A A A A A G A T A C T G A C G G C ...
                   4030                       4040 ...
                                         ... LYS ILE LYS LEU LYS VAL ASP ASN THR ASP
                                         ... A A G A T T A A A C T C A A A G T A G A T A A T A C A G A T
                                                          4060              4070              4080

GLY ASN ASN LEU LEU THR VAL ASP ALA THR ...
G G G A A T A A T C T A T T A A C C G T T G A T G C A A C A ...
                   4090                      4100                4110 ...
                                         ... LYS GLY ALA SER VAL ALA LYS GLY GLU PHE
                                         ... A A A G G T G C A T C C G T T G C C A A G G G C G A G T T T
                                                          4120              4130              4140

ASN ALA VAL THR THR ASP ALA THR THR ALA ...
A A T G C C G T A A C A A C A G A T G C A A C T A C A G C C ...
                   4150                        4160                 4170 ...
                                         ... GLN GLY THR ASN ALA ASN GLU ARG GLY LYS
                                         ... C A A G G C A C A A A T G C C A A T G A G C G C G G T A A A
                                                         4180              4190              4200
                          ...
```

FIG. 24U

```
VAL VAL VAL LYS GLY SER ASN GLY ALA THR ...
GTGGTTGTCAAGGGGTTCAAATGGTGCAACT...
          4210                    4220
                ... ALA THR GLU THR ASP LYS LYS VAL ALA
                ...GCTACCGAAACTGACAAGAAAAAGTGGCA
                      4240            4250          4260

THR VAL GLY ASP VAL ALA LYS ALA ILE ASN ....
ACTGTTGGCGACGTTGCTAAAGCGATTAAC...
         4270                    4280
                ... ASP ALA ALA THR PHE VAL LYS VAL GLU ASN
                ...GACGCAGCAACTTTCGTGAAAGTGGAAAAT
                      4300              4310          4320

ASP SER ALA THR ILE ASP ASP SER PRO ....
GACGACAGTGCTACGATTGATGATAGCCCA...
         4330                    4340
                ... THR ASP ASP GLY ALA ASN ASP ALA LEU LYS
                ...ACAGATGATGGCAAATGATGCTCTCAAA
                      4360              4370          4380

ALA GLY ASP THR LEU THR LEU LYS ALA GLY ....
GCAGGCGACACCTTGACCTTAAAAGCGGGT...
         4390                    4400          4410
```

FIG. 24V

```
                        ... LYS ASN LEU LYS VAL LYS ARG ASP GLY LYS
                        ... A A A A A C T T A A A A G T T A A A C G T G A T G G T A A A
                                                              4430                4440
                            4420

ASN ILE THR PHE ALA LEU ALA ASN ASP LEU ...
A A T A T T A C T T T T G C C C T T G C G A A C G A C C T T ...
                4450                    4470...
                                         ... SER VAL LYS SER ALA THR VAL SER ASP LYS
                                         ... A G T G T A A A A A G C G C A A C C G T T A G C G A T A A A
                            4480                              4490                4500

LEU SER LEU GLY THR ASN GLY ASN LYS VAL ...
T T A T C G C T T G G T A C A A A C G G C A A T A A A G T C ...
                4510                    4530...
                                         ... ASN ILE THR SER ASP THR LYS GLY LEU ASN
                                         ... A A T A T C A C A A G C G A C A C C A A A G G C T T G A A C
                            4540                              4550                4560

PHE ALA LYS ASP SER LYS THR GLY ASP ASP ...
T T C G C T A A A G A T A G T A A G A C A G G C G A T G A T ...
                4570                    4590...
                                         ... ALA ASN ILE HIS LEU ASN GLY ILE ALA SER
                                         ... G C T A A T A T T C A C T T A A A T G G C A T T G C T T C A
                            4600                              4610                4620
```

FIG.24W

THR LEU THR ASP THR LEU LEU ASN SER GLY....
ACTTTAACTGATACATTGTTAAATAGTGGT...
   4630     4640   4650....

ALA THR THR ASN LEU GLY GLY ASN GLY ILE
...GCGACAACCAATTTAGGTGGTAATGGTATT
        4660     4670     4680

THR ASP ASN GLU LYS LYS ARG ALA ALA SER....
ACTGATAACGAGAAAAAACGCGGGCGAGC...
   4690     4700   4710....

VAL LYS ASP VAL LEU ASN ALA GLY TRP ASN
...GTTAAAGATGTCTTGAATGCGGGTTGGAAT
        4720     4730     4740

VAL ARG GLY VAL LYS PRO ALA SER ALA ASN....
GTTCGTGGTGTTAAACCGGCATCTGCAAAT...
   4750     4760   4770....

ASN GLN VAL GLU ASN ILE ASP PHE VAL ALA
...AATCAAGTGGAGAATATCGACTTTGTAGCA
        4780     4790     4800

THR TYR ASP THR VAL ASP PHE VAL SER GLY....
ACCTACGACACAGTGGACTTTGTTAGTGGA...
   4810     4820   4830....

FIG.24X

```
                     ... ASP LYS ASP THR THR SER VAL THR VAL GLU
                     ... G A T A A A G A C A C C A C G A G T G T A A C T G T T G A A
                                     4840              4850              4860

SER LYS ASP ASN GLY LYS ARG THR GLU VAL ...        ... LYS ILE GLY ALA LYS THR SER VAL ILE LYS
A G T A A A G A T A A T G G C A A G A G A A C C G A A G T T ...   ... A A A A T C G G T G C G A A G A C T T C T G T T A T C A A A
            4870              4880              4890                           4900              4910              4920

ASP HIS ASN GLY LYS LEU PHE THR GLY LYS ...        ... GLU LEU LYS ASP ALA ASN ASN GLY VAL
G A C C A C A A C G G C A A A C T G T T T A C A G G C A A A ...   ... G A G C T G A A G G A T G C T A A C A A T A A T G G C G T A
            4930              4940              4950                           4960              4970              4980

THR VAL THR GLU THR ASP GLY LYS ASP GLU ...        ... GLY ASN GLY LEU VAL THR ALA LYS ALA VAL
A C T G T T A C C G A A A C C G A C G G C A A A G A C G A G ...   ... G G T A A T G G T T T A G T G A C T G C A A A A G C T G T G
            4990              5000              5010                           5020              5030              5040
```

FIG.24Y

```
ILE ASP ALA VAL ASN LYS ALA GLY TRP ARG ...
ATTGATGCCGTGAATAAGGCTGGTTGGAGA...
          5050                5060           5070....
                      ... VAL LYS THR THR GLY ALA ASN GLY GLN ASN
                      ...GTTAAAACAACAGGTGCTAATGGTCAGAAT
                                    5080              5090            5100

ASP ASP PHE ALA THR VAL ALA SER GLY THR ....
GATGACTTCGCAACTGTTGCGTCAGGCACA...
          5110                5120           5130....
                      ... ASN VAL THR PHE ALA ASP GLY ASN GLY THR
                      ...AATGTAACCTTTGCTGATGGTAATGGCACA
                                    5140              5150            5160

THR ALA GLU VAL THR LYS ALA ASN ASP GLY ....
ACTGCCGAAGTAACTAAAGCAAACGACGGT...
          5170                5180           5190....
                      ... SER ILE THR VAL LYS TYR ASN VAL LYS VAL
                      ...AGTATTACTGTTAAATACAATGTTAAAGTG
                                    5200              5210            5220

ALA ASP GLY LEU LYS LEU ASP GLY ASP LYS ....
GCTGATGGCTTAAAACTAGACGGCGATAAA...
          5230                5240           5250....
```

FIG.24Z

```
                                    ILE VAL ALA ASP THR THR VAL LEU THR VAL
                                ... A T C G T T G C A G A C A C G A C C G T A C T T A C T G T G
                                                        5260                    5270              5280
                                ...

ALA ASP GLY LYS VAL THR ALA PRO ASN ASN ...
G C A G A T G G T A A A G T T A C A G C T C C G A A T A A T ...
            5290                    5300          5310 ...

GLY ASP GLY LYS LYS PHE VAL ASP ALA SER
                                ... G G C G A T G G T A A G A A A T T T G T T G A T G C A A G T
                                                        5320                    5330              5340
                                ...

GLY LEU ALA ASP ALA LEU ASN LYS LEU SER ...
G G T T T A G C G G A T G C G T T A A A T A A G C T A A G C ...
            5350                    5360          5370 ...

TRP THR ALA THR ALA GLY LYS GLU GLY THR
                                ... T G G A C G G C A A C T G C T G G T A A A G A A G G C A C T
                                                        5380                    5390              5400
                                ...

GLY GLU VAL ASP PRO ALA ASN SER ALA GLY ...
G G T G A A G T T G A T C C T G C A A A T T C A G C A G G G ...
            5410                    5420          5430 ...

GLN GLU VAL LYS ALA GLY ASP LYS VAL THR
                                ... C A A G A A G T C A A A G C G G G C G A C A A A G T A A C C
                                                        5440                    5450              5460
                                ...
```

FIG.24A'

```
PHE LYS ALA GLY ASP ASN LEU LYS ILE LYS....
TTTAAAGCCCGGCGACAAACCTGAAAATCAAA....
             5470              5480         5490....
                 ...GLN SER GLY LYS ASP PHE THR TYR SER LEU
                 ...CAAAGCGGCAAAGACTTTACCTACTTCGCTG
                              5500              5510             5520

LYS LYS GLU LEU LYS ASP LEU THR SER VAL....
AAAAAAGAGCTGAAAGACCTGACCAGCGTA....
             5530              5540         5550....
                 ...GLU PHE LYS ASP ALA ASN GLY GLY THR GLY
                 ...GAGTTCAAAGACGCAAACGGCGGTACAGGC
                              5560              5570             5580

SER GLU SER THR LYS ILE THR LYS ASP GLY....
AGTGAAAGCACCAAGATTACCAAAGACGGC....
             5590              5600         5610....
                 ...LEU THR ILE THR PRO ALA ASN GLY ALA GLY
                 ...TTGACCATTACGCCGGCAAACGGTGCGGGT
                              5620              5630             5640

ALA ALA GLY ALA ASN THR ALA ASN THR ILE....
GCGGCAGGTGCAAACACTGCAAACACCATT....
             5650              5660         5670....
```

FIG.24B'

```
          ...    SER  VAL  THR  LYS  ASP  GLY  ILE  SER  ALA  GLY
          ...    AGCGTAACCAAAGATGGCATTAGCCGGGT
                              5680            5690            5700

ASN  LYS  ALA  VAL  THR  ASN  VAL  VAL  SER  GLY  ...
AATAAAGCAGTTACAAACGTTGTGAGCGGA...
              5710            5720            5730...

LEU  LYS  LYS  PHE  GLY  ASP  GLY  HIS  THR  LEU
                    ...  CTGAAGAAATTTGGTGATGGTCATACGTTG
                                   5740            5750            5760

ALA  ASN  GLY  THR  VAL  ALA  ASP  PHE  GLU  LYS  ...
GCAAATGGCACTGTTGCTGATTTTGAAAAG...
              5770            5780            5790...

HIS  TYR  ASP  ASN  ALA  TYR  LYS  ASP  LEU  THR
                    ...  CATTATGACAATGCCTATAAAGACTTGACC
                                   5800            5810            5820

ASN  LEU  ASP  GLU  LYS  GLY  ALA  ASP  ASN  ASN  ...
AATTTGGATGAAAAGGCGCGGATAATAAT...
              5830            5840            5850...

PRO  THR  VAL  ALA  ASP  ASN  THR  ALA  ALA  THR
                    ...  CCGACTGTTGCCGACAATACCGCTGCAACC
                                   5860            5870            5880
```

FIG.24C'

```
VAL GLY ASP LEU ARG GLY LEU GLY TRP VAL ...
GTGGGCGATTTGCGCGGCCTTGGGCTGGGTC...
         5890              5900         5910...

ILE SER ALA ASP LYS THR THR GLY GLU PRO
                ...ATTTCTGCGGACAAAACCACAGGCGAACCC
                               5920         5930         5940

ASN GLN GLU TYR ASN ALA GLN VAL ARG ASN ....
AATCAGGAATACAACGCGCAAGTGCGTAAC...
         5950              5960         5970...

ALA ASN GLU VAL LYS PHE LYS SER GLY ASN
                ...GCCAATGAAGTGAAATTCAAGAGCGGCAAC
                               5980         5990         6000

GLY ILE ASN VAL SER GLY LYS THR LEU ASN ....
GGTATCAATGTTTCCGGTAAAACATTGAAC...
         6010              6020         6030...

GLY THR ARG VAL ILE THR PHE GLU LEU ALA
                ...GGTACGCGCGTGATTACCTTTGAATTGGCT
                               6040         6050         6060

LYS GLY VAL VAL LYS SER ASN GLU PHE ....
AAAGGCGAAGTGGTTAAATCGAAATGAATTT...
         6070              6080         6090
```

FIG.24D'

```
ASN LEU VAL LYS VAL GLY ASP MET THR GLY LYS VAL GLY ASP MET TYR TYR ...
AACTTGGTTAAAGTTGGCGATGACAGGTAAAACTGAAAAATAT...      ...ACCGTTAAAGAATGCCGATGGTTCGGAAAACG
     6130                6140                                    6100         6110         6120

ASN LEU VAL LYS VAL GLY ASP MET TYR TYR ...
AACTTGGTTAAAGTTGGCGATATGTATTAC...
     6130              6140

... SER LYS GLU ASP ILE ASP PRO ALA THR SER
                                              ... AGCAAAGAGGATATTGACCCGGCAACCAGT
                                                       6160         6170         6180

LYS PRO MET THR GLY LYS THR GLU LYS TYR ...
AAACCGATGACAGGTAAAACTGAAAAATAT...
     6190              6200

... LYS VAL GLU ASN GLY LYS VAL VAL SER ALA
                                              ... AAGGTTGAAAACGGCAAAGTCGTTTCTGCT
                                                       6220         6230         6240

ASN GLY SER LYS THR GLU VAL THR LEU THR ...
AACGGCAGCAAGACCGAAGTTACCCTAACC...
     6250              6260

... ASN LYS GLY TYR SER GLY TYR VAL THR GLY ASN
                                              ... AACAAAGGTTCCGGCTATGTAACAGGTAAC
                                                       6280         6290         6300
```

FIG.24E'

```
GLN VAL ALA ASP ALA ILE ALA LYS SER GLY...
CAAGTGGCTGATGCGATTGCGAAATCAGGC...
        6310              6320              6330...
                    ...PHE GLU LEU GLY LEU ALA ASP ALA ALA GLU
                    ...TTTGAGCTTGGTTTGGCTGATGCGGCAGAA
                            6340              6350              6360

ALA GLU LYS ALA PHE ALA GLU SER ALA LYS....
GCTGAAAAAGCCTTTGCAGAAAGCGCAAAA....
        6370              6380              6390....
                    ...ASP LYS GLN LEU SER LYS ASP LYS ALA GLU
                    ...GACAAGCAATTGTCTAAAGATAAAGCGGAA
                            6400              6410              6420

THR VAL ASN ALA HIS ASP LYS VAL ARG PHE...
ACTGTAAATGCCCACGATAAAGTCCGTTTT...
        6430              6440              6450...
                    ...ALA ASN GLY LEU ASN THR LYS VAL SER ALA
                    ...GCTAATGGTTTAAATACCAAAGTGAGCGCG
                            6460              6470              6480

ALA THR VAL GLU SER THR ASP ALA ASN GLY...
GCAACGGTGGAAAGCACTGATGCAAACGGC...
        6490              6500              6510...
```

FIG.24F'

```
                                         ASP LYS VAL THR THR THR PHE VAL LYS THR
                                      ...GATAAAGTGACCACAACCTTTGTGAAAACC
                                         6520              6530         6540

ASP VAL GLU LEU PRO LEU THR GLN ILE TYR ....
GATGTGGAATTGCCCTTTAACGCAAATCTAC...
         6550              6560....

ASN THR ASP ALA ASN GLY ASN LYS ILE VAL
                                      ...AATACCGATGCAAACGGTAATAAGATCGTT
                                         6580              6590         6600

LYS ALA ASP GLY LYS TRP TYR GLU LEU ....
AAAAAGCTGACGGAAAATGGTATGAACTG...
         6610              6620....

ASN ALA ASP GLY THR ALA SER ASN LYS GLU
                                      ...AATGCTGATGGTACGGCGAGTAACAAAGAA
                                         6640              6650         6660

VAL THR LEU GLY ASN VAL ASP ALA ASN GLY ....
GTGACACTTGGTAACGTGGATGCAAACGGT...
         6670              6680....

LYS LYS VAL VAL LYS VAL THR GLU ASN GLY
                                      ...AAGAAAGTTGTGAAAGTAACCGAAAATGGT
                                         6700              6710         6720
```

FIG.24G'

```
ALA ASP LYS TRP TYR TYR THR ASN ALA ASP ...
GCG GAT AAG TGG TAT TAC ACC AAT GCT GAC ...
                  6730                    6740                    6750...

... GLY ALA ALA ASP LYS THR LYS GLY GLU VAL
                    ... GGT GCT GCG GAT AAA ACC AAA GGC GAA GTG
                                6760                    6770                    6780

SER ASN ASP LYS VAL SER THR ASP GLU LYS ...
AGC AAT GAT AAA GTT TCT ACC GAT GAA AAA ...
                  6790                    6800                    6810...

... HIS VAL VAL ARG LEU ASP PRO ASN ASN GLN
                    ... CAC GTT GTC CGC CTT GAT CCG AAC AAT CAA
                                6820                    6830                    6840

SER ASN GLY LYS GLY VAL VAL ILE ASP ASN ...
TCG AAC GGC AAA GGC GTG TGG TCA TTG ACA AAT ...
                  6850                    6860                    6870...

... VAL ALA ASN GLY GLU ILE SER ALA THR SER
                    ... GTG GCT AAT GGC GAA ATT TCT GCC ACT TCC
                                6880                    6890                    6900

THR ASP ALA ILE ASN GLY SER GLN LEU TYR ...
ACC GAT GCG ATT AAC GGA AGT CAG TTG TAT ...
                  6910                    6920                    6930...
```

FIG.24H'

```
                              ...  ALA VAL ALA LYS GLY VAL THR ASN LEU ALA
                              ...  GCCGTGGCAAAAGGGGTAACAAACCTTGCT
                                                  6940           6950           6960

GLY GLN VAL ASN ASN LEU GLU GLY LYS VAL ...      ... ASN LYS VAL GLY LYS ARG ALA ASP ALA GLY
GGACAAAGTGAATAATCTTGAGGGCAAAGTG...               ...AATAAAGTGGGCAAACGTGCAGATGCAGGT
              6970           6980           6990                  7000           7010           7020

THR ALA SER ALA LEU ALA ALA SER GLN LEU ...      ... PRO GLN ALA THR MET PRO GLY LYS SER MET
ACAGCAAGTGCATTAGCGGCTTCACAGTTA...                ...CCACAAGCCACTATGCCAGGTAAATCAATG
              7030           7040           7050                  7060           7070           7080

VAL ALA ILE ALA GLY SER SER TYR GLN GLY ...      ... GLN ASN GLY LEU ALA ILE GLY VAL SER ARG
GTTGCTATTGCGGGAAGTAGTTATCAAGGT...                ...CAAAATGGTTTAGCTATCGGGGTATCAAGA
              7090           7100           7110                  7120           7130           7140
```

FIG.24I'

```
ILE SER ASP ASN GLY LYS VAL ILE ILE ARG ....
ATTTCCGATAATGGCAAAGTGATTATTCGC...
              7150              7160          7170....

... LEU SER GLY THR THR ASN SER GLN GLY LYS
      ... TTGTCAGGCACAACCAATAGTCAAGGTAAA
                7180              7190              7200

THR GLY VAL ALA ALA GLY VAL GLY TYR GLN ....
ACAGGCGTTGCAGCAGGTGTTGGTTACCAG...
              7210              7220          7230....

... TRP ***
      ... TGGTAATAGAATTCCCGGATCCGC
                7240              7250
```

FIG.25A

NTHi strain 12 hia locus

```
    TYR TYR HIS TRP *** PRO THR PRO ...
GAATTCTATTACCACTGGTAACCAAACCT...
             10              20              30
                                    ...ALA ALA THR PRO GLU THR ALA GLN GLN ILE
                                    ...GCTGCAAACGCCAGAAACAGCAACAAATT
                                                    40              50              60

HIS TRP LEU HIS GLN PHE THR LYS ALA ARG ...
CACTGGCTACATCAATTTACCAAAGCTCGC...
             70              80              90
                                    ...ILE GLN TRP ARG LYS THR HIS SER LEU PHE
                                    ...ATTCAATGGCGCAAAACCCATTCCTTATTC
                                                   100             110             120

PHE LYS GLU LYS PRO ASP TYR ALA PHE VAL ...
TTTAAAGAAAAACCCGATTATGCCTTTGTG...
            130             140             150
                                    ...LEU ALA GLU ASN GLY LYS VAL GLN GLU ILE
                                    ...CTGGCAGAAAACGGCAAAGTGCAAGAAATC
                                                   160             170             180

LYS ALA GLU TYR ARG ARG ILE ALA ASN GLN ...
AAAGCAGAATATCGCCGCATTGCCAATCAA...
            190             200             210
```

FIG.25B

```
                        ...ILE VAL GLU GLU ALA MET ILE ILE ALA ASN
                        ...A T T G T G G A A G A A G C A A T G A T T A T T G C C A A A C
                                               220                 230                 240

ILE CYS ALA ALA GLN PHE LEU HIS GLU GLN ...
...A T C T G C G C C G C C C A A T T T T T A C A C G A A C A G ...
                    250                 260                 270 ...

...ALA LYS THR GLY ILE PHE ASN ALA HIS SER
                                               ...G C A A A A A C A G G C A T T T T C A A C G C C C A C A G C
                                                                   280                 290                 300

GLY PHE ASP LYS LYS TYR LEU GLU ASN ALA ...
...G G T T T T G A T A A A A A A T A C T T A G A A A A T G C G ...
                    310                 320                 330 ...

...HIS HIS PHE LEU MET ALA ASN LEU ALA ASN
                                                       6431.SL (
                                       ...C A C C A T T T C T T A A T G G C A A A T T T A G C C A A T
                                                                   340                 350                 360

GLU GLN ASN GLN THR GLU LEU ALA GLU ARG ...
...G A A C A A A A T C A A A C T G A A C T G G C A G A A C G T ...
                    370                 380                 390 ...

...TYR SER VAL GLU ASN LEU ALA THR LEU ASN
                                               ...T A T T C A G T A G A A A A C T T A G C A A C C T T A A A C
                                                                   400                 410                 420
```

FIG.25C

GLY TYR CYS GLN MET ARG HIS ASP ILE GLU ...
GGCTATTGCCAAATGCGTCACGATATTGAA...
430         440         450

... PRO ILE GLU SER ASP TYR LEU GLU LEU ARG
...CCCATCGAAAGCGATTATTTAGAACTGCGT
    460         470         480

LEU ARG ARG TYR LEU THR PHE ALA GLU PHE ...
TTACGCCGTTATTTAACTTTCGCCGAATTT...
490         500         510

... LYS SER GLU ASN ALA PRO HIS PHE GLY LEU
...AAATCAGAAAATTAGCACCGCACTTTGGTCTT
    520         530         540

GLY LEU GLU GLY TYR ALA THR TRP THR SER ...
GGTTTAGAAGGCTATGCCACTTGGACATCG...
550         560         570

... PRO ILE ARG LYS TYR SER ASP MET VAL ASN
...CCCATCCGCAAATATTCAGATATGGTTAAT
    580         590         600

HIS ARG LEU ILE LYS ALA VAL LEU ALA LYS ...
CATCGCTTAATCAAAGCCGTGCTGGCAAAA...
610         620         630

FIG.25D

```
                                    ... GLN  PRO  TYR  GLU  LYS  PRO  GLN  ASN  ASP  VAL
                                    ...                                              
                                    ... C A G C C T T A T G A A A A C C A C A A A T G A C G T G
                                              640            650            660

LEU  ALA  ARG  LEU  GLN  GLU  SER  ARG  ARG  GLN ...
         6432.SL (
T T G G C A C G T T T G C A A G A G T C T C G C C G C C A A ...
              670            680            690

... ASN  ARG  LEU  VAL  GLU  ARG  ASP  ILE  ALA  ASP
                     ...
                     ... A A T C G C C T A G T G G A A C G T G A T A T T G C C G A T
                              700            710            720

TRP  LEU  TYR  CYS  ARG  TYR  LEU  ALA  ASP  LYS ...
T G G C T A T A T T G C C G T T A T C T T G C T G A C A A A ...
              730            740            750

... VAL  ALA  GLU  ASN  VAL  GLU  PHE  ASN  ALA  GLU
                     ... G T G G C T G A A A A T G T G G A A T T T A A T G C C G A G A A
                              760            770            780

VAL  GLN  ASP  VAL  MET  ARG  ALA  GLY  LEU  ARG ...
G T G C A A G A T G T A A T G C G T G C A G G C T T A C G C ...
              790            800            810
```

FIG. 25E

```
                                ...VAL GLN LEU LEU GLU ASN GLY ALA SER LEU
                                ...GTACAACTGCTCGAAAATGGTGCATCGCTA
                                    820                    830           840
                                ...
PHE ILE PRO ALA ALA THR LEU HIS ASN ASN  ....
TTTATTCCTGCCGCCACGTTGCACAACAAC T  ....
            850                  860    870  ....

...LYS GLU GLU ILE GLN LEU ASN PRO ASP GLU
                                ...AAAGAAGAAATACAGCTAAACCCTGACGAA
                                        880                 890           900
                                ...
LEU ALA LEU TYR ILE LYS GLY GLU ARG THR  ....
CTCGCCCTCTATATAAAAGGCGAACGCACT  ....
            910                  920     930 ....

...TYR LYS ILE GLY ASP ILE VAL LYS VAL LYS
                                ...TACAAAATAGGCGACATTGTGAAAGTGAAA
                                        940                 950           960
                                ...
LEU THR GLU VAL LYS GLU ALA THR ARG SER  ....
CTCACAGAAGTGAAAGAAGCAACTCGCAGT  ....
            970                  980     990 ....

...ILE VAL GLY GLU ILE LEU GLN  ***  LEU PRO
                                ...ATTGTGGGCGAAATACTTCAATAAAATTGCC
                                        1000               1010           1020
                                ...
```

FIG.25F

```
PHE GLN TYR VAL THR GLU ASP GLY LYS THR...
GTTCCAATATGTTACGGAAGACGGCAAAAC...
         1030           1040          1050
                     VAL VAL LYS VAL GLY ASN GLU TYR TYR GLU
                  ...CGTTGTGAAAGTGGGCAATGAGTATTACGA
                        1060           1070          1080

ALA LYS GLN ASP GLY SER ALA ASP MET ASP...
AGCCAAGCAAGACGGTTCGGCGGATATGGA
         1090           1100
                        6295.SL
                                 1110
                     LYS LYS VAL LYS ASN GLY GLU LEU VAL LYS
                  ...TAAAAAAGTCAAAAATGGCCGAGCTGGTGAA
                        1120           1130          1140

THR LYS VAL LYS LEU VAL SER ALA ASN GLY...
AACTAAAAGTGAAATTGGTATCGGCAAACGG
         1150           1160          1170
                     THR ASN PRO VAL LYS ILE SER ASN VAL ALA
                  ...TACAAATCCGGTGAAAATCAGCAATGTTGC
                        1180           1190          1200

GLU GLY THR GLU ASP THR ASP ALA VAL SER...
GGAAGGCACGGAAGATACCGATGCCGGTCAG
         1210           1220          1230
```

FIG.25G

```
                                      ...  PHE LYS GLN LEU LYS ALA LEU GLN ASN LYS
                                      ...C T T T A A G C A G T T G A A A G C C T T G C A A A A C A A
                                                                                              1250       1260

GLN VAL THR LEU SER ALA SER ASN ALA TYR...        ALA ASN GLY GLY SER ASP ALA ASP VAL GLY
A C A G G T T A C G T T A A G C G C G A G C A A T G C T T A ...   ...T G C C A A T G G C G G T A G C G G A T G C C G A C G T C G G
                      1270                1280         1290 ...                1300              1310               1320

LYS VAL THR GLN THR LEU SER ASN GLY LEU...        ASN PHE LYS SER THR ASP GLY GLU
C A A G G T A A C T C A A A C T T T A A G C A A T G G T T T ...   ...G A A T T T T A A A T T T A A A T C C A C A G A C G G C G A
                      1330                1340         1350 ...                1360              1370               1380

LEU LEU ASN ILE LYS ALA ASP LYS ASP THR...        VAL THR ILE THR ARG ALA SER GLY ALA ASN
G T T G T T G A A C A T C A A A A G C A G A C A A G G A C A C ...   ...G G T T A C C A T T A C G C G G G C A A G C G G T G C G A A
                      1390                1400         1410 ...                1420              1430               1440
```

FIG.25H

```
GLY ALA ALA ALA THR ASP ALA ASP LYS ILE...
TGGTGCGGGCGGCGACTGATGCCGACAAGAT....
                1450              1460              1470
                              ...TAAAGTGGCTTCAGACGGCATTAGCGCGGG
                                 LYS VAL ALA SER ASP GLY ILE SER ALA GLY
                                  1480              1490              1500

ASN LYS ALA VAL LYS ASN VAL ALA ALA GLY...
TAATAAAGCAGTTAAAAACGTCGCGGCAGG...
                1510              1520              1530
                              ...CGAAATTTCCGCCACTTCCACCGATGCCGAT
                                 GLU ILE SER ALA THR SER THR ASP ALA ILE
                                  1540              1550              1560
                                                  (6271.SL)

ASN GLY SER GLN LEU TYR ALA VAL ALA LYS...
TAACGGCAGTCAGTTGTATGCCGTGGCAAAA...
                1570              1580              1590
                              ...GGGGGTAAACAAACCTTGCTGGACAAGTGAA
                                 GLY VAL THR ASN LEU ALA GLY GLN VAL ASN
                                  1600              1610              1620

LYS VAL GLY LYS ARG ALA ASP ALA GLY THR...
TAAAGTGGGCAAACGTGCAGATGCAGGTAC...
                1630              1640              1650
```

FIG. 25I

```
                              ALA SER ALA LEU ALA ALA SER GLN LEU PRO
                          ...AGCAAGTGCATTAGCGGCTTCACAGTTACC
                                        1660          1670          1680

GLN ALA SER MET PRO GLY LYS SER MET VAL...
ACAAGCCCTCTATGCCGGGTAAATCAATGGT...
          1690                1700          1710 ...

SER ILE ALA GLY SER SER TYR GLN GLY GLN
                          ...TTCTATTGCGGGAAGTAGTTATCAAGGTCA
                                        1720          1730          1740

SER GLY LEU ALA ILE GLY VAL SER ARG ILE...
AAGTGGTTTAGCTATCGGGGTATCAAGAAT...
          1750                1760          1770 ...

SER ASP ASN GLY LYS LEU ILE ILE ARG LEU
                          ...TTCCGATAATGGCAAATTGATTATTCGCTT
                                        1780          1790          1800

SER GLY THR THR ASN SER GLN GLY LYS THR...
GTCAGGCACAACCAATAGCCAAGGTAAAAC...
          1810                1820          1830 ...

GLY VAL ALA ALA GLY VAL GLY TYR GLN TRP
                          ...AGGCGTTGCAGCAGGTGTTGGTTACCAGTG
                                        1840          1850          1860

*** ***
GTAATAGAATTC
     1870
```

FIG.26A

| | |
|---|---|
| ATG AAC AAA ATT TTT AAC GTT ATT TCG AAT GTT GTG ACT CAA ACT TGG<br>Met Asn Lys Ile Phe Asn Val Ile Trp Asn Val Val Thr Gln Thr Trp<br>2130                                                              2135                                                            2140 | 48 |
| GTT GTC GTA TCT GAA CTC ACT CGC ACC CAC ACC AAA TGC GCC TCC GCC<br>Val Val Val Ser Glu Leu Thr Arg Thr His Thr Lys Cys Ala Ser Ala<br>2145                                                              2150                                                            2155 | 96 |
| ACC GTG GCG GTT GCC GTA TTG GCA ACC CTG TTG TCC GCA ACG GTT GAG<br>Thr Val Ala Val Ala Val Leu Ala Thr Leu Leu Ser Ala Thr Val Glu<br>2160                                                              2165                                                            2170                      2175 | 144 |
| GCG AAC AAC AAT ACT CCT GTT ACG AAT AAG TTG AAG GCT TAT GGC GAT<br>Ala Asn Asn Asn Thr Pro Val Thr Asn Lys Leu Lys Ala Tyr Gly Asp<br>2180                                                              2185                                                            2190 | 192 |
| GCG AAT TTT AAT TTC ACT AAT AAT TCG ATA GCA GAT GCA GAA AAA CAA<br>Ala Asn Phe Asn Phe Thr Asn Asn Ser Ile Ala Asp Ala Glu Lys Gln<br>2195                                                              2200                                                            2205 | 240 |
| GTT CAA GAG GCT TAT AAA GGT TTA AAT CTA AAT GAA AAA AAT GCG<br>Val Gln Glu Ala Tyr Lys Gly Leu Leu Asn Leu Asn Glu Lys Asn Ala<br>2210                                                              2215                                                            2220 | 288 |

FIG.26B

AGT GAT AAA CTG TTG GTG GAG GAC AAT ACT GCG GCG ACC GTA GGC AAT        336
Ser Asp Lys Leu Leu Val Glu Asp Asn Thr Ala Ala Thr Val Gly Asn
            2225                    2230                    2235

TTG CGT AAA TTG GCC TGG GTA TTG TCT AGC AAA AAC GGC ACA AGG AAC        384
Leu Arg Lys Leu Gly Trp Val Leu Ser Ser Lys Asn Gly Thr Arg Asn
2240                    2245                    2250                    2255

GAG AAA AGC CAA CAA GTC AAA CAT GCG GAT GAA GTG TTG TTT GAA GGC        432
Glu Lys Ser Gln Gln Val Lys His Ala Asp Glu Val Leu Phe Glu Gly
                    2260                    2265                    2270

AAA GGC CGT GTG CAG GTT ACT TCC ACC TCT GAA AAC GGC AAA CAC ACC        480
Lys Gly Val Gln Val Thr Ser Thr Ser Glu Asn Gly Lys His Thr
2275                    2280                    2285

ATT ACC TTT GCT TTA GGG AAA GAC CTT GGT GTG AAA ACT GCG ACT GTG        528
Ile Thr Phe Ala Leu Gly Lys Asp Leu Gly Val Lys Thr Ala Thr Val
            2290                    2295                    2300

AGT GAT ACC TTA ACG ATT GGC GGT GCT GCA GGT GCT ACA ACA               576
Ser Asp Thr Leu Thr Ile Gly Gly Ala Ala Gly Ala Thr Thr
2305                    2310                    2315

FIG.26C

```
ACA CCG AAA GTG AAT GTA ACT AGT ACA ACT GAT GGC TTG AAG TTC GCT    624
Thr Pro Lys Val Asn Val Thr Ser Thr Thr Asp Gly Leu Lys Phe Ala
2320                        2325                    2330        2335

AAA GAT GCT GCG GGT GCT AAT GGC GAT ACT ACG GTT CAC TTG AAT GGT    672
Lys Asp Ala Ala Gly Ala Asn Gly Asp Thr Thr Val His Leu Asn Gly
           2340                        2345                    2350

ATT GGT TCA ACC TTG ACA GAC ACG CTT GTG GGT TCT CCT GCT ACT CAT    720
Ile Gly Ser Thr Leu Thr Asp Thr Leu Val Gly Ser Pro Ala Thr His
       2355                        2360                    2365

ATT GAC GGA GGA GAT CAA AGT ACG CAT TAC ACT CGT GCA GCA AGT ATC    768
Ile Asp Gly Gly Asp Gln Ser Thr His Tyr Thr Arg Ala Ala Ser Ile
   2370                        2375                        2380

AAG GAT GTC TTG AAT GCG GGT TGG AAT ATC AAG GGT GTT AAA GCT GGC    816
Lys Asp Val Leu Asn Ala Gly Trp Asn Ile Lys Gly Val Lys Ala Gly
2385                        2390                    2395

TCA ACA ACT GGT CAA TCA GAA AAT GTC GAT TTT GTT CAT ACT TAC GAT    864
Ser Thr Thr Gly Gln Ser Glu Asn Val Asp Phe Val His Thr Tyr Asp
       2400                        2405                    2410        2415
```

FIG.26D

ACT GTT GAG TTC TTC AGT GCG GAT ACA GAG ACC ACG ACT GTT ACT GTA    912
Thr Val Glu Phe Leu Ser Ala Asp Thr Glu Thr Thr Val Thr Val
2420                          2425                      2430

GAT AGC AAA GAA AAC GGT AAG AGA ACC GAA GTT AAA ATC GGT GCG AAG    960
Asp Ser Lys Glu Asn Gly Lys Arg Thr Glu Val Lys Ile Gly Ala Lys
      2435                       2440                      2445

ACT TCT GTT ATC AAA GAA AAA GAC GGT AAG TTA TTT ACT GGA AAA GCT   1008
Thr Ser Val Ile Lys Glu Lys Asp Gly Lys Leu Phe Thr Gly Lys Ala
      2450                       2455                     2460

AAC AAA GAG ACA AAT AAA GTT GAT GGT GCT AAC GCG ACT GAA GAT GCA   1056
Asn Lys Glu Thr Asn Lys Val Asp Gly Ala Asn Ala Thr Glu Asp Ala
      2465                      2470                      2475

GAC GAA GGC AAA GGC TTA GTG ACT GCG AAA GAT GTG ATT GAC GCA GTG   1104
Asp Glu Gly Lys Gly Leu Val Thr Ala Lys Asp Val Ile Asp Ala Val
      2480                      2485                      2490      2495

AAT AAG ACT GGT TGG AGA ATT AAA ACA ACC GAT GCT AAT GGT CAA AAT   1152
Asn Lys Thr Gly Trp Arg Ile Lys Thr Thr Asp Ala Asn Gly Gln Asn
      2500                      2505                      2510

FIG.26E

```
GGC GAC TTC GCA ACT GTT GCA TCA GGC ACA AAT GTA ACC TTT GCT AGT      1200
Gly Asp Phe Ala Thr Val Ala Ser Gly Thr Asn Val Thr Phe Ala Ser
                2515                    2520                2525

GGT AAT GGT ACA ACT GCG ACT GTA ACT AAT GGC ACC GAT GGT ATT ACC      1248
Gly Asn Gly Thr Thr Ala Thr Val Thr Asn Gly Thr Asp Gly Ile Thr
                2530                    2535                2540

GTT AAG TAT GAT GCG AAA GTT GGC GAC GGC TTA AAA CTA GAT GGC GAT      1296
Val Lys Tyr Asp Ala Lys Val Gly Asp Gly Leu Lys Leu Asp Gly Asp
                2545                    2550                2555

AAA ATC GCT GCA GAT ACG ACC GCA CTT ACT GTG AAT GAT GGT AAG AAC      1344
Lys Ile Ala Ala Asp Thr Thr Ala Leu Thr Val Asn Asp Gly Lys Asn
                2560                    2565                2570        2575

GCT AAT AAT CCG AAA GGT AAA GTG GCT GAT GTT GCT TCA ACT GAC GAG      1392
Ala Asn Asn Pro Lys Gly Lys Val Ala Asp Val Ala Ser Thr Asp Glu
                2580                    2585                2590

AAG AAA TTG GTT ACA GCA AAA GGT TTA GTA ACA GCC TTA AAC AGT CTA      1440
Lys Lys Leu Val Thr Ala Lys Gly Leu Val Thr Ala Leu Asn Ser Leu
                2595                    2600                2605
```

FIG. 26F

```
AGC TGG ACT ACA ACT GCT GAG GCG GAC GGT GGT ACG CTT GAT GGA    1488
Ser Trp Thr Thr Thr Ala Ala Glu Ala Asp Gly Gly Thr Leu Asp Gly
2610                            2615                      2620

AAT GCA AGT GAG CAA GAA GTT AAA GCG GCC GAT AAA ACC TTT AAA    1536
Asn Ala Ser Glu Gln Glu Val Lys Ala Gly Asp Lys Val Thr Phe Lys
2625                            2630                      2635

GCA GGC AAG AAC TTA AAA GTG AAA CAA GAG GGT GCG AAC TTT ACT TAT    1584
Ala Gly Lys Asn Leu Lys Val Lys Gln Glu Gly Ala Asn Phe Thr Tyr
2640                            2645                      2650                2655

TCA CTG CAA GAT GCT TTA ACA GGC TTA ACG AGC ATT ACT TTA GGT ACA    1632
Ser Leu Gln Asp Ala Leu Thr Gly Leu Thr Ser Ile Thr Leu Gly Thr
2660                            2665                      2670

GGA AAT AAT GGT GCG AAA ACT GAA ATC AAC AAA GAC TTA ACC ATC    1680
Gly Asn Asn Gly Ala Lys Thr Glu Ile Asn Lys Asp Gly Leu Thr Ile
2675                            2680                      2685

ACA CCA GCA AAT GGT GCG GGT GCA AAT AAT GCA AAC ACC ATC AGC GTA    1728
Thr Pro Ala Asn Gly Ala Gly Ala Asn Asn Ala Asn Thr Ile Ser Val
2690                            2695                      2700
```

FIG.26G

```
ACC AAA GAC GCC ATT AGT GCG GGT CAG TCG GTT AAA AAC GTT GTG      1776
Thr Lys Asp Gly Ile Ser Ala Gly Gly Gln Ser Val Lys Asn Val Val
2705                              2710                    2715

AGC GGA CTG AAG AAA TTT GGT GAT GCG AAT TTC GAT CCG CTG ACT AGC  1824
Ser Gly Leu Lys Lys Phe Gly Asp Ala Asn Phe Asp Pro Leu Thr Ser
2720                              2725                    2730                     2735

TCC GCC GAC AAC TTA ACG AAA CAA AAT GAC GAT GCC TAT AAA GGC TTG  1872
Ser Ala Asp Asn Leu Thr Lys Gln Asn Asp Asp Ala Tyr Lys Gly Leu
2735                              2740                    2745                     2750

ACC AAT TTG GAT GAA AAA GGT ACA GAC AAG CAA ACT CCA GTT GTT GCC  1920
Thr Asn Leu Asp Glu Lys Gly Thr Asp Lys Gln Thr Pro Val Val Ala
2755                              2760                    2765

GAC AAT ACC GCC GCA ACC GTG GGC GAT TTG CGC CTT GGC TGG GTC      1968
Asp Asn Thr Ala Ala Thr Val Gly Asp Leu Arg Gly Leu Gly Trp Val
2770                              2775                    2780

ATT TCT GCG GAC AAA ACC ACA GGC TCA ACG GAA TAT CAC GAT CAA      2016
Ile Ser Ala Asp Lys Thr Thr Gly Gly Ser Thr Glu Tyr His Asp Gln
2785                              2790                    2795
```

FIG. 26H

```
GTT CCG AAT GCG AAC GAA GTG AAA TTC AAA AGC GGC AAC GGT ATC AAT     2064
Val Arg Asn Ala Asn Glu Val Lys Phe Lys Ser Gly Asn Gly Ile Asn
2800                          2805                          2810                          2815

GTT TCC GGT AAA ACG GTC AAC GGT ACG CGT GAA ATT ACT TTT GAA TTG     2112
Val Ser Gly Lys Thr Val Asn Gly Arg Arg Glu Ile Thr Phe Glu Leu
                              2820                          2825                          2830

GCT AAA GGT GAA GTG GTT AAA TCG AAT GAA TTT ACC GTC AAA GAA ACC     2160
Ala Lys Gly Glu Val Val Lys Ser Asn Glu Phe Thr Val Lys Glu Thr
2835                          2840                          2845

AAT GGA AAG GAA ACG AGC CTG GTT AAA GTT GGC GAT AAA TAT TAC AGC     2208
Asn Gly Lys Glu Thr Ser Leu Val Lys Val Gly Asp Lys Tyr Tyr Ser
                              2850                          2855                          2860

AAA GAG GAT ATT GAC TTA ACA ACA GGT CAG CCT AAA TTA AAA GAT GGC     2256
Lys Glu Asp Ile Asp Leu Thr Thr Gly Gln Pro Lys Leu Lys Asp Gly
2865                          2870                          2875

AAT ACA GTT GCT GCG AAA TAT CAA GAT AAA GGT GGC AAA GTC GTT TCT     2304
Asn Thr Val Ala Ala Lys Tyr Gln Asp Lys Gly Gly Lys Val Val Ser
2880                          2885                          2890                          2895
```

FIG. 26I

GTA ACG GAT AAT ACT GAA GCT ACC ATA ACC AAC AAA GGT TCT GGC TAT    2352
Val Thr Asp Asn Thr Glu Ala Thr Ile Thr Asn Lys Gly Ser Gly Tyr
2900                          2905                          2910

GTA ACA GGT AAC CAA GTG GCA GAT GCG ATT GCG AAA TCA GGC TTT GAG    2400
Val Thr Gly Asn Gln Val Ala Asp Ala Ile Ala Lys Ser Gly Phe Glu
2915                          2920                          2925

CTT GGC TTG GCT GAT GAA GCT GAT GCG AAA CGG GCG TTT GAT GAT AAG    2448
Leu Gly Leu Ala Asp Glu Ala Asp Ala Lys Arg Ala Phe Asp Asp Lys
2930                          2935                          2940

ACA AAA GCC TTA TCT GCT GGT ACA ACG GAA ATT GTA AAT GCC CAC GAT    2496
Thr Lys Ala Leu Ser Ala Gly Thr Thr Glu Ile Val Asn Ala His Asp
2945                          2950                          2955

AAA GTC CGT TTT GCT AAT GGT TTA AAT ACC AAA GTG AGC GCG GCA ACG    2544
Lys Val Arg Phe Ala Asn Gly Leu Asn Thr Lys Val Ser Ala Ala Thr
2960                          2965                          2970                          2975

GTG GAA AGC ACC GAT GCA AAC GGC GAT AAA GTG ACC ACA ACC TTT GTG    2592
Val Glu Ser Thr Asp Ala Asn Gly Asp Lys Val Thr Thr Thr Phe Val
2980                          2985                          2990

FIG.26J

```
AAA ACC GAT GTG GAA TTG CCT TTA ACG CAA ATC TAC AAT ACC GAT GCA    2640
Lys Thr Asp Val Glu Leu Pro Leu Thr Gln Ile Tyr Asn Thr Asp Ala
             2995                      3000                 3005

AAC GGT AAG AAA ATC ACT AAA GTT GTC AAA GAT GGG CAA ACT AAA TGG    2688
Asn Gly Lys Lys Ile Thr Lys Val Val Lys Asp Gly Gln Thr Lys Trp
             3010                      3015                 3020

TAT GAA CTG AAT GCT GAC GGT ACG GCT GAT ATG ACC AAA GAA GTT ACC    2736
Tyr Glu Leu Asn Ala Asp Gly Thr Ala Asp Met Thr Lys Glu Val Thr
             3025                      3030                 3035

CTC GGT AAC GTG GAT TCA GAC GCC AAG AAA GTT GTG AAA GAC AAC GAT    2784
Leu Gly Asn Val Asp Ser Asp Ala Lys Lys Val Val Lys Asp Asn Asp
             3040                      3045                 3055
                                                       3050

GGC AAG TGG TAT CAC GCC AAA GCT GAC GGT ACT GCG GAT AAA ACC AAA    2832
Gly Lys Trp Tyr His Ala Lys Ala Asp Gly Thr Ala Asp Lys Thr Lys
             3060                      3065                 3070

GGC GAA GTG AGC AAT GAT AAA GTT TCT ACC GAT GAA AAA CAC GTT GTC    2880
Gly Glu Val Ser Asn Asp Lys Val Ser Thr Asp Glu Lys His Val Val
             3075                      3080                 3085
```

FIG.26K

```
ACC CTT GAT CCA AAT GAT CAA TCA AAA GGT AAA GGT GTC GTG ATT GAC    2928
Ser Leu Asp Pro Asn Asp Gln Ser Lys Gly Lys Gly Val Val Ile Asp
            3090                3095               3100

AAT GTG GCT AAT GCC GAT ATT TCT GCC ACT TCC ACC GAT GCG ATT AAC    2976
Asn Val Ala Asn Gly Asp Ile Ser Ala Thr Ser Thr Asp Ala Ile Asn
            3105                3110               3115

GGA AGT CAG TTG TAT GCT GTG GCA AAA GGG GTA ACA AAC CTT GCT GGA    3024
Gly Ser Gln Leu Tyr Ala Val Ala Lys Gly Val Thr Asn Leu Ala Gly
3120            3125                3130               3135

CAA GTC AAT AAT CTT GAG GGC AAA GTG AAT AAA GTG GGC AAA CGT GCA    3072
Gln Val Asn Asn Leu Glu Gly Lys Val Asn Lys Val Gly Lys Arg Ala
            3140                3145               3150

GAT GCA GGT ACA GCA AGT GCA TTA GCG GCT TCA CAG TTA CCA CAA GCC    3120
Asp Ala Gly Thr Ala Ser Ala Leu Ala Ala Ser Gln Leu Pro Gln Ala
            3155                3160               3165

ACT ATG CCA GGT AAA TCA ATG GTT GCT ATT GCG GGA AGT TAT CAA         3168
Thr Met Pro Gly Lys Ser Met Val Ala Ile Ala Gly Ser Ser Tyr Gln
            3170                3175               3180
```

FIG.26L

```
GGT CAA AAT GGT TTA GCT ATC GGG GTA TCA AGA ATT TCC GAT AAT GGC    3216
Gly Gln Asn Gly Leu Ala Ile Gly Val Ser Arg Ile Ser Asp Asn Gly
    3185                    3190                    3195

AAA GTC ATT ATT CGC TTG TCA GGC ACA ACC AAT AGT CAA GGT AAA ACA    3264
Lys Val Ile Ile Arg Leu Ser Gly Thr Thr Asn Ser Gln Gly Lys Thr
    3200                    3205                    3210       3215

GGC GTT GCA GCA GGT GTT GGT TAC CAG TGG                            3294
Gly Val Ala Ala Gly Val Gly Tyr Gln Trp
    3220                    3225
```

FIG. 27A

Alignment of NTHi strain 12 5' ORF with HI1733 from H. influenzae strain Rd

```
          10         20         30         40         50         60         70
X         PTPAATPETAQQIHWLHQFTKARIQWRKTHSLFFKEKPDYAFVLAENGKVQEIKAEYRRIANQIVEEAMIIA
          ||||||||||||||||||||||||||||||||||||||||||||||||||||||||||||||||||||||
          AWQPEMPETAQQIHWLHQFTKARIQWRKTHSLFFKEKPDYAFVLAENGKVQEIKAEYRRIANQIVEEAMIIA
          330        340        350        360        370        380        400

80         90        100        110        120        130        140
          NICAAQFLHEQAKTGIFNAHSGFDKKYLENAHHFLMANLANEQNQTELAERYSVENLATINGYCQMRHDIEP
          ||||||||||||||||||  ||||||| ||||||||||||||||||||||||||||||||||||||||||
          NICAAQFLHEQAKTGIFNHSGFDKKFLENAHHFLMANLANEQNQTELAERYSVENLATINGYCQMRHDIEP
          410        420        430        440        450        460        470

150        160        170        180        190        200        210
          IESDYLELRLRRYLITFAEFKSELAPHFGLGLEGYATIWTSPIRKYSDMNHRLIKAVLAKQPYEKPQNDVLAR
          |||||||||||||||||||||||||||||||||||||||||||||||||||||||||||||||||||||||
          IESDYLELRLRRYLITFAEFKSELAPHFGLGLEGYATIWTSPIRKYSDMNHRLIKAVLAKQPYEKPQNDVLAR
          480        490        500        510        520        530        540

220        230        240        250        260        270        280
          LQESRRQNRLVERDIADWLYCRYLADKVAENVEFNAEVQDMRAGLRVQLLENGASLFIPAATLHNNKEEIQ
          |||   |||||||||||||||||||||| ||  ||| |||||||||||||||||||||||||||||||||
          LQEARRQNRLVERDIADWLYCRYLADKVASNAEFFEAEVQDMRAGLRVQLLENGASLFIPAATLHNNKEEIQ
          550        560        570        580        590        600        610
```

FIG.27B

```
                   290       300       310       320       330
              LNPDELALYIKGERIYKIGDIVKKLTEVKEATRSIVGEILQ
              ||||||||||||||||||||||||||||||||||||||||
              LNPDELALYIKGERIYKIGDMVKVKLTEVKEATRSIVGEILQ X
                   620       630       640       650
```

```
##cross-references GB:L42023; TIGR:HI1733
##note              named as homolog to a protein from Escherichia coli
SUMMARY             #length 659    #molecular-weight 75782    #checksum 8365

A64139
MFQDNPLLAQLKQQIHDSKEQVEGVVKSIDKAYGFLECDKKIYFIAPPSMKKVMHGDKIKATTEKQGDKE
QAEPEALIEPMLITRFIAKVRFNKDKKLQVLVDHPSINQPIGAQQAKSVKEELQEGIMVVANLKTHPLRDD
RFFYATINQLICRADDELAPAWVTLARHEQSRYPVRGAEPYEMLDQKIRENLTAIHFVTIDSESIMDMDD
ALYIEPIAQNSIQTGMKLVVAIADPTAYIALDSQIEQEAKQRCFINYLPGFNIPMLPRELSDELCSLIAN
EITRPALVCYIETDLTGNITAKPHFVSAYVQSKAKLAYNKVSDYLEQADIVAWQPEMPETAQQIHMLHQFTK
ARIQWRKTHSLFFKEKPDYAFVLAENGKVQEIKAEYRRIANQIVEEAMITANICAAQFLHEQAKTGIFNT
HSGFDKKFLENAHNFLMANLANEQNQTELAERYSVENLATINGYCQMRHDIEPIESDYLELRLRRYLITFA
EFKSELAPHFGLGLEGYATWTSPIRKYSDMVNHRLIKAVLAKQPYEKPQNDVLARLQEARRQNRLVERDI
ADMLYCRYLADKVASNAEFEAEVQDMVRAGLRVQLLENGASLFTIPAATLHNNKEEIQLNPDELALYIKGE
RIYKIGDMVKLTEVKEATRSIVGEILQ
```

FIG.28A

Alignment of *H. influenzae* Hia/Hsf and *M. catarrhalis* 200 kDa proteins

```
          10        20        30        40        50
MNKIFNVIWNVMIQIWAVVSELTRAHTKRASATVAAVLATVLSATVQA-S------------  33
.............V....V.....T..C....V.....L....N------------  32
.............V....V.....T..C....V.....A...AE.NN-----------  29
.............V....V.....C.........V.....A...AE.NN-----------  K22
.............V....V.....C........T....L..T...TT------------  M4071
.............V....V.....T..C....V.....L....E.NN------------  11
.....N.......V....V.....T..........T...Q...AE.NS------------  K9
..K....V....V..............T......T..T.....ET.....L.F....NATDEDEELDPVV.  HSF
..H.YK..F.KA.G.FMA.A.YAKS.STQGGSCATGQ.GSVCTLSFARIAALAVLVIGATLS...
..H.YK..F.KA.G.FMA.A.CAKS.SGGSSSSTAGQ.GSSFVIRLTRVATLAILVIGATLN...
*.** **.****  *** **   ***  ****  **   *   *  *
                                                              :
                                                              :
                                                              :
                                                              :    ------------  33
                                                              :    ------------  32
                                                              :    ------------  29
                                                              :    ------------  K22
                                                              :    ------------  M4071
                                                              :    ------------  11
                                                              :    ------------  K9
                      ...RTAPVLSFHSDKEGIGEKEVTENSMGIYFDNKGVLKA------------  HSF
```

FIG. 28B

```
...RTAPVLSFHSDKEGIGEKVTENSMMGIYFHNKGVLKA------------              API
...GTFVKVQSTEDDIEDSAATKDINKNQALKAGDILTLKA------------              Rd
...GSAYAQKKDTKHIAIGEQNQPRRSGTAKADGDRAIAIGENANAQCG                  4223
...GSAYAQN-NSK-AIFGTTGNNDN---ASASNFASIAIGSLAKAHAN                  LES-1
       *                                   *

GAITLKAGINLKIKQNIDESTNASSFTYSLKKDLTDLTSVATEKLSFGANGDKVDITSDANG... 33
GAITLKAGINLKIKQ----SINASSFTYSLKKDLTDLTSVATEKLSFGANGDKVDITSDANG... 32
GKN-LKAKLDQQGKSVTFALAKDLLVKTAKVSDTLTIGGNTPAAQGATP---KVSITSTADG... 29
QAIAIGSSNKTVNG-SSLEKIGTDITGQESIAIGGDVKASGDASIAIGSDDLHLLDQHGNPK... K22
QAIAIGGSKPDPRNQAANQKAGSHAKGKESIAIGGDVLAEGDASIAIGSDDLYLDRNSINSK... M4071
  **                               *****  *                  *   11
```

FIG.28C

```
                                                                                                     K9
                                                                                                     HSF
                                                                                                     API
                                                                                                     Rd
                                                                                                     4223
                                                                                                     LES-1

...LKLAKTGNGN--VHLNGLDSTLPDAVINIGVLSSSS-FTPNDVEKTR
...LKLAKTGNGN--VHLNGLDSTLPDAVINIGVLSSSS-FTPNDVEKTR
...LKLAKGINGDTAVHLNGLASTLPDVTNIGASTSVT-FSPSDIEKTR
...HPKGTLINDLINGHAVLKEIRSSKINDVKYRKTTASGHASTAVGAMS
...YPNGLLSTLIQN-HTVLRQIFDSNGSQ-KYRRTAAEGHASTAVGAMA
      *          *      * **

33
                                                                                                     32
                                                                                                     29
                                                                                                     K22

.....AATVKDVLNAGMNIKGAKTAGGNVESVDLVSAYNNVEFITGDKNTLDVVLTAKENGKTTEVK
.....AATVKDVLNAGMNIKGAKTAGGNVESVDLVSAYNNVEFITGDKNTLDVVLTAKENGKTTEVK
.....AATIKDVLNAGMNIKGAKVAGGNTESVDLVAGYDNVEFITGDKNTLDVVLTAKENGKTTEVK
.....YAQGHFSNAFGTRA-TAKSAYSLAVGLAATAEGQSTIAIGSDATSSSLGAIAIGAGTRAQLQ
.....YAKGHFANAFGTRS-TAEGNYSKAVGLTAKAEKGYTIAIGSNAQAINYGALALGADTRVDLD
  *      *   *   **    **        ***   ****   *                **
```

FIG. 28D

```
                                                                                        M4071
                                                                                        11
                                                                                        K9
                                                                                        HSF
                                                                                        API
                                                                                        Rd
                                                                                        4223
                                                                                        LES-1
                                                                                                33

...........FTPKT----SVIKEKD-----GKLFTGKENDINKV--TSNTA------
...........FTPKT----SVIKEKD-----GKLFTGKENDINKV--TSNTA------
...........FTPKT----SVIKDNN-----GKLLTGKQLKDANIG--TAINA------
...........GSIALGQGSVVTQSD-NNSRPAYTPNIQALDPKFQ-AINNIKAGPLSIG
...........YGIALGYGSQIINNNNNNNNKAYVPEGNGSNIKSSKATGNGLF---SIG
               *                              **      *

TDNIDEGNGLVTAKAVI-DAVNKAGMVIKTITTANGQNGDFATVASGINVTFESGDGTTASVT...
TDNIDEGNGLVTAKAVI-DAVNKAGMVIKTITTANGQNGDFATVASGINVTFESGDGTTASVT...
TEDITDEAMA*
*RYRRGNGLVTAKIVI-EAVNKSGMVRVKTITTANGQNDDFATVASGINVTFANGNGITASVT...
SNSIKRKIINVGAGVNKTDAVNVAQLEAVVKAKERRITFQGDNSTDVKIGLDNTLTIKGG...
SSTIKRKIINVGAGYEDTDAVNVAQLKAVENLAK-RQITFKGDINGTGVKKKLGETLTIKGG...
  *             *   * ***   *   **          *    * ***   *
```

FIG. 28E

```
                                                                                    32
                                                                                    29
                                                                                    K22
                                                                                    M4071
                                                                                    11
                                                                                    K9
                                                                                    HSF
                                                                                    API
                                                                                    Rd
                                                                                    Rd
                                                                                    4223
                                                                                    LES-1

...----------------------------------------:
...----------------------------------------:
...----------------------------------------:
...----------------------------------------:
...----------------------------------------:
...----------------------------------------:
...KDINGNGITVKYD-ALVGDGLKFDSDKKIVADITALTVIG--:
...KDINGNGITVKYD-ALVGDGLKFDSDKKIVADITALTVIG--:
...----------------------------------------:
...NSTD--GITVKYE-ALVGDGLKIDGDQKIVADITALTVIG--:
...AETNA--LTDNN-  IGVVKEADNSGLKVKLAKTLNLTEVTTTL:
...ETQADKLTDNNIGVVTD-NNIGLKVKLAKNLSGLETVSTKNL:
   ****  **              ** **       *  *

:
                                                              :
                                                              :
                                                              :
                                                              :
                                                              :
                                                              :...GALEGISKDQEVKAGETVTFK..
                                                              :...GALEGISKDQEVKAGETVTFK..
                                                              :
                                                              :...GALEGISKDQEVKAGETVTFK..
                                                              :...GALEGTSKDQEVKAGETVTFK..
                                                              :...NAETTAALGTT-R..
                                                                       *

GKVAEIAKEDDKKKLVNAGDLVTALGNLSWKAKAEADITD--GALEGISKDQEVKAGETVTFK..
GKVAEIAKEDDKKKLVNAGDLVTALGNLSWKAKAEADITD--GALEGISKDQEVKAGETVTFK..
GKVAEIAKEDDKKKLVNAGDLVTALGNLSWKAKAEADITDGALEGISKDQEVKAGETVTFK..
GKVAEIAKEDDKKKLVNAGDLVTALGNLSWKAKAEADITD--GALEGTSKDQEVKAGETVTFK..
NATTTVKVGSSSSTTAELLSDSLTFTQPNTGSQSTSKTVVGVNGVKFTNNAETTAALGTT-R..
```

FIG.28F

```
TASEKVTVGSGNN-TAELQSGGLTFT-PTTNA-STDKTVGTDGLKFTDNSN-TALEDTT-R...
    *                *                *                    * **              * *..
                                                                              ...  33
                                                                              ...  32
                                                                              ...  29
                                                                              ...  K22
                                                                              ...  M4071
                                                                              ...  11
                                                                              ...  K9
..AGKNLKVKQDGANFTYSLQDALTGLTSATLGGTTNGENDA                                    HSF
..AGKNLKVKQDGANFTYSLQDALTGLTSATLGGTTNGENDA                                    API
..AGKNLKVKQDGANFTYSLQDALTGLTSATLGGTTNGENDA                                    Rd
..ITRDKIGFARD-GDVDE------                                                     4223
..ITKDKIGFSNKAGTVDENKPYLDKDKLKVGNSTLNMCGLT                                    LES-1
  ***          *                                  * * * * *
              60                  70
-------AGSTTGTNSLNVYGK-NNSNFNSANNSIA...
-------NN--.SV..G..A..D---T...TT........
-------N--.SV..G..A..D---T...TT........
-------T.G..S..G.KA..ST..P..A.G..AT..
-------N--.PV..K.KA..D-A.F..--T.........
-------.ASV.CR.....D-T.TK..A............
KTVINKDGLTITPAGNGGTTGTNTISBTKDGIK..NKAI..VASGLRAYDDA..DVL...AT...
```

FIG. 28G

```
KTVINKDGLTITPAGNQGTTGTNTISBTKDGIK..NKAI..VASGLRAYDDA..DVL...AT...
KTVINKDGLTITPAGNQGTTGTNTISBTKDGIK..NKAI..VASGLRAYDDA..DVL...AT...
---------------------------------------------------------------
------------VNNTIGGSNKQIQVGADGIKFADMVNVSNAAKFGTTRITEEEIGFAD.....
           **  ***   * ** *****              *   *
                   ...80         90        100        110        120
                   ...DLNKQNDSVYDGLLNLNEKGTDKSKFLVADETTATVGNLRKL------    33
                                  ------ATDENED..EELEPVQRSV.------    32
                      E.HVQDA.K......D.N.S......N.A...------         29
                      E.HVQDA.K......D.N.S......N.A...------         K22
                      AR.F.GA.......DAN.N-L..T.DKA...------          M4071
                      AE..VQEA.K......NAS-D.L..E.N.A....D...------   11
                      ......G.H......N.AN-..L..D.N.A.....D...------  K9
                      ......RHVEDA.K......NAN.QP-..T.S.A....D...------ HSF
                      ......RHVEDA.K......NAN.QP-..TDS.A....D...------ API
                      ......RHVEDA.K......NAN.QP-......S.A....D...------ Rd
                      ----KQAP.LDKKQ..KVGSVAITIDNGI..AGNKIS..A.GSSANDA  4223
                      ......GKVDKK..P.LDKKQ..QVG..VKIT.DSGINAGDQKISNVKDATDDTDA LES-1
                                *   **                              *

FIG.28G
                   130       140        150        160
GMVVSTKNSTKEE-SNQVKQADEVLFEG-KDGVTVTSKSENGKHTVT------
R.SFKSAKEGTG.QEGTTEV--------------------------------
...L.S..G.RN.K.Y........T.-SGAA..S:S.KD....I..:------
...L.S..G.RN.K.Y........T.-SGAA..S.S.KD....I..:------
```

FIG. 28H

```
                                                                              33
                                                                              32
                                                                              29
...L.S..G.RN.K.Q...H.........                    ----------------             K22
...L.S..G.RN.K.Q...H.........-.G..Q..T.....I.... ----------------             M4071
.......GKEN.K.Q.............K.S.G..Q..T......AI. ----------------             11
.............................G...-........T.-AGAA...........I.VSVAETKADCGLEKD..  K9
.............................G...-........T.-AGAA...........I.VSVAETKADSGLEKD..  HSF
.............................G...-........T.-AGAA...........I.VSVAETKADSGLEKD..  API
VTIEQL.AAKPILNAGAGISVTPTEISVDAKSGN..APTY.IGVKT.ELNSDGTSDKFSVKG...              Rd
VTYKQL.-----------------------------------------                              4223
           *    ***  *   *      * *****     *  *                              LES-1

:...:                                    33
                                     :...:                                    32
                                     :...:                                    29
                                     :...:                                    K22
                                     :...:                                    M4071
                                     :...:                                    11
                                     :...:GDTIKLKVDNQMTDNVLTVGNGTAVTKGGFETVKTGATDADRGKVT  K9
                                     :...:GDTIKLKVDNQMTDNVLTVGNGTAVTKGGFETVKTGATDADRGKVT  HSF
                                     :...:GDTIKLKVDNQMTDNVLTVGNGTAVTKGGFETVKTGATDADRGKVT  API
                                     :...:SGINNSLVTAEHLASYLNEWNRTADSALQSF-TVKEED-DDDANAIT  Rd
                                     :...:-------QVQQDADGALQSF-SIRDEK-GQEFTISN  4223
                                     :...:      *       *  ******   *    *         LES-1
```

FIG. 28I

```
VKDATANDADKKVATVKDVATAINSAATFVKTENLTTSIDEDNPTDNGKDDALKAGDILTFK...          33
VKDATANDADKKVATVKDVATAINSAATFVKTENLTTSIDEDNPTDNGKDDALKAGDILTFK...          32
VKDATANDADKKVATVKDVATAINSAATFVKTENLTTALDEADAKDQG-DDALKAGDILTFK...          29
VAKUITRKNAGAVSILKLKGKNGLTVATKKD-GTVTFGLSQDSGLFIGKSTLNNDGLTVKDIN...         K22
LYSNGNTPNTFETITFA-GENGISISNDIAKGKVKGIDPINGLTTPKLTVGSDKDGKTQLV...          M4071
                                                                          11
                                                                          K9
..AGRNLKVKRDGKNITFDLAKNLEVKTAKVSDILTIGGNTPTGTTAT--                        HSF
..AGRNLKVKRDGKNITFDLAKNLEVKTAKVSDILTIGGNTPTGTTAT--                        API
..AGRNLKVKRDGKNITFDLAKNLEVKTATFSDRLTIG--                                  Rd
   EQIQVGANGI.FTNVNGSNPGTGIANPARITRDKIGFAGSDGAVDINK                       4223
   IEQVASGN-.T...IR------                                                 LES-1
   *        *   **
```

FIG.28J

```
                                                                                                    33
                                                                                                    32
                                                                                                    29
                                                                                                    K22
                                                                                                    M4071
                                                                                                    11
                                                                                                    K9
                                                                                                    HSF
                                                                                                    API
                                                                                                    Rd
                                                                                                    4223
                                                                                                    LES-1

------------------------------------------------------------------------------------------------
------------------------------------------------------------------------------------------------
------------------------------------------------------------------------------------------------
------------------------------------------------------------------------------------------------
------------------------------------------------------------------------------------------------
------------------------------------------------------------------------------------------------
...PKVNITTSTADGLNFAKETADASGSKNVYLKGIATTLTEPSAGAKSSHVDLNVDATK-KSNAA...
...PKVNITTSTADGLNFAKETADASGSKNVYLKGIATTLTEPSAGAKSSHVDLNVDATK-KSNAA...
...PYLDQDKLQVGNVKITNIGINAGGKAITGLSPTLPSIADQSS-RNIELGNTI-QDKDKSNAA...
                                      ---GLSPTL[SITNAGGVRTTEQGNTITSDEDKSKAA...
 *  ***   *    *****    **    ***    **   **    *    *          ***  **
                                                                                ...SIEDVLRAGMINQGNGNNVDYVATYDTVNFTDDSTGTTTVTVTQKADG
                                                                                ...SIEDVLRAGMINQGNGNNVDYVATYDTVNFTDDSTGTTTVTVTQKADG
------------------------------------------------------------------------------------------------
                                                                                ...SNDILNTGFNLRNNSNSVGFVSTYNTVDFIDGNATTAKVTY-DEINQ
                                                                                ...SIGDILNTGFNLRNNSNSVGFVSTYNTVDFIDGNATTAKVTY-TEINQ
```

FIG. 28K

```
                    .   ** *** ****** *  * * ******* ***   * **** *** * ** 
                    :   :    :    :    :    :    :    :    :    :    :  --- 33
                    :    :    :    :    :    :    :    :    :    :    :  --- 32
                    :    :    :    :    :    :    :    :    :    :    :  --- 29
                    :    :    :    :    :    :    :    :    :    :    :  --- K22
        KGADVKIGAKTSVIKDHNGKLFTGKDLKDANNGATVSEDDGKDTGTGLVTAKTVIDAVNKSG...  --- M4071
        KGADVKIGAKTSVIKDHNGKLFTGKDLKDANNGATVSEDDGKDTGTGLVTAKTVIDAVNKSG...  --- 11
                    :    :    :    :    :    :    :    :    :    :    :  --- K9
TSKVVYDVNVDDTTIHLIGTDDNK-KLGVKTTKLNKTDANGNTATNFNVNSSDEDALVNAKD......     --- HSF
TSKVTYDVNVDEKTIELIGDNGKTNKIGVKTTLTTINANGK-ATNF-STIINDALVNAKDI......     --- API
                *    *    *                    *  * *                   --- Rd

...WRVTGEGATAETGATAVNAGNAETVTSGTSVNFKNGNATTATVSKDNGNIN  HSF
                                                              ...WRVTGEGATAETGATAVNAGNAETVTSGTSVNFKNGNATTATVSKDNGNIN  API
                                                                                                                  :  Rd
```

FIG. 28L

```
...IAENLNTLAKEIHTTKGTADTALQTFTVKKVDENNNADDANAIT----        4223
...AENLNTLAKEIHTTKGTADTALQTFTVKKK----DGATDDETIT            LES-1
    * ****    *         **         *      ***

...:                                                       33
...:                                                       32
...:                                                       29
VKYDVNVGDGLKIGDDKKIVADTITLIVTGGKVSVPAGANSVNNKKLVNAEGLATALNNLS...  K22
VKYDVNVGDGLKIGDDKKIVADTITLIVTGGKVSVPAGANSVNNKKLVNAEGLATALNNLS... M4071
VGQKNANNQ--VNTLTLKGENGLNIKTDKNGIVTFGIN---                   11
VGKDGIQNGKTVNTLKLKGENGLIVATNKDGIVTFGIN                      K9
*                       *     *   * ***

...:WTAKADKYADGESEGETDQEVKAGDKVIF-KAGKNLKVKQSEKDFTYSLQD     HSF
```

FIG. 28M

```
...WTAKADKYADGESEGETDQEVKAGDKVTF-KAGNLKVKQSEKDFTYSLQD                              API
------------------------TTSGLKAGKST-LNDGLSIKNPTGSEQIQVGADG                        Rd
------------------------TQSGLKAGDSTTLNKDGKSIKNPASNEQIQVGADG                       4223
                        *  ****              *    * * * *                        LES-1

TLTGLTSITLGGTANGRNDIGTVINKDGLTITLANGAAAGTDASNGNT----ISVTKDGISA..
TLTGLTSITLGGTANGRNDIGTVINKDGLTITLANGAAAGTDASNGNT----ISVTKDGISA..
VKFAKVNNNGVVGAGIDGTTRITRDEIGFTGINGSLDKSKPHL-----------SLDGINA..
VKFAKVDK-GNSSTGIDGTSRITKDQIGFTGANGSLDTTKPHLTKDKLKVGEVEITNTGINA..
 *                 **                                        ** *

```
                                    K9
                                    HSF
                                    API
                                    Rd
                                    4223
                                    LES-1

...GNKEITNVKSA----------LKTYKDIQNIA
        ...GNKEITNVKSA----------LKTYKDIQNIA
        ...GGKKTINIQSGEIAQNSHDAVTGGKIYDLKT
        ...GGKKTINIQSGDITQNSNDAVTGGRVYDLKT
        :.* **** ********** ***  *

33
                                                    32
                                                    29
                                                    K22

---DE.
                                            ---EI.
                                            ---EI.
                                               *
GATQPAANTAEVAKQDLVDLTKPATGAAGNGADAKAPDTTPAATVGDLRGLGWLSAKKTADE...
```

FIG. 280

```
M4071  ----------------------------------------
11     ----------------------------------------
K9     ...TQDKEFHAAVKNANEVEFVGKNGATVSAKT--------
HSF    ...TQDKEFHAAVKNANEVEFVGKNGATVSAKT--------
SPI    ...ENKISSTAKTAQNSLHEFSVADEQGNNFTV--------
Rd     ...ESKINSAAKTAQNSLHEFSVADEQGNNFTV--------
4223   ----------------------------------------
LES-1  ----------------------------------------
         *  **   *    **

M4071  ----------------------------------------
11     ----------------------------------------
K9     ----------------------------------------
HSF    ----------------------------------------
SPI    ---ISVTKGSFAEVKT-------------------------
Rd     ---ISVTKGSFAEVKT-------------------------
4223   ----------------------------------------
LES-1  ----------------------------------------

M4071  DNNGKHTVTIDVAEAKVGDGLEKDITDGKIKLIVDNTDGNNLLTVDATKGASVAKGEFNAVTT...
11     DNNGKHTVTIDVAEAKVGDGLEKDITDGKIKLIVDNTDGNNLLTVDATKGASVAKGEFNAVTT...
K9     ----------------------------------------
HSF    ----------------------------------------
SPI    SNPYSSYDTSKTSDVITFAGENGITTKVNKGVVRVGIDQIKGLTTPKLTVGNNNGKIVIDS...
Rd     SNPYSSYDTSKTSDVITFAGENGITTKVNKGVVRVGIDQIKGLTTPKLTVGNNNGKIVIDS...
4223   ----------------------------------------
LES-1  ----------------------------------------
         *  **                         *

M4071  ----------------------------------- 33
11     ----------------------------------- 32
K9     ----------------------------------- 29
HSF    ----------------------------------------
SPI    ----------------------------------------
Rd     ----------------------------------------
4223   ...DATTGGQMAD-RGKVK----AEDENGADVDKKV-----
LES-1  ----------------------------------------
```

FIG.28P

```
                                        ...DATTQGQVNAD-RGKVK----AEDENGADVDKKV----------               K22
                                        ---------------------------------------------               M4071
                                        ---------------------------------------------               11
                                        ---------------------------------------------               K9
                                        ...DATTAQGTNANERGKVVVKGSNGATATETDKKKV---------               HSF
                                        ...DATTAQGTNANERGKVVVKGSNGATATETDKKKV---------               API
                                        ...QNCQVNTTGLSNILANVINDKGSVRTTEQGNIIKDEDKTRA               Rd
                                        ...KDGQNTTTGLSNILANVINDGAGHSLS-QGLAN-DTDKTRA               LES-1
                                                              *
                                                                                200

INLNIDSSGNAVGSSTITFKAGDNLKIKQSGN...

ATVKDVAKAINDAATFVKVESTDDDIENGAAGKNETTDQALKAGDTLTLKAGRNLKAKLLDQN...
ATVKDVAKAINDAATFVKVESTDDDIENGAAGKNETTDQALKAGDTLTLKAGRNLKAKLLDQN...

ATVGDVAKAINDAATFVKVEN-DDSATIDDSPIDDGANDALKAGDTLTLKAGRNLKVRDG...
ATVGDVAKAINDAATFVKVEN-DDSATIDDSPIDDGANDALKAGDTLTLKAGRNLKVRDG...

ASIVDVLSAGFNLQGNGEAVDFVSTYDIVNFADGNATTAKVTYDDTSKTSKVVVDVNVDITT...
ASIGDVLNAGFNLQGNGEAVDFVSTYDIVDFIDGNATTAKVTYDDTSKTSKVVVDVNVDNKT...
****                *  *   *                    *           *
                170                180              190                200
```

FIG.28Q

```
                                                                              33
                                                                              32
                                                                              29
                                                                              K22
                                                      ------FALANDINVKNATVSDKLSLGANGKVDITSDANG----    M4071
                                                  ..D--FTYS.KRE.RNLTSVETE.F...N..............----    11
                                                  ...GKSVT....K..D.TS.K......I.KDIN.............----    K9
                                                  ...GKSVT....K..D.TS.K......I.KDIN.............----    HSF
                                                  .........T.EK..................N......T......----    API
                                                  ..............K..G..T....T.TI.GGAAAGAT.TPKVNVTSTIDG    Rd
                                                  ..............K..SMRT....T.TI.GSTTTGSA.TPKVNVTSTASG    4223
                                                  ...-KNIT.............S..S.........T..N..N....TK.----    LES-1
                                                  ...-KNIT.............S..S.........T..N..N....TK.----
                                                  ......................N.........T....-
                                                                                  *
           ...IEVK-DKKLGVKTTLTSIGTGANKFALSNQATGDALVKASDIVA---
           ...IEVTSDKKLGVKTTLTLTKTSANGNATKFSA-ADGDALVKASDIAT--
                                *          *                     *
LKFAKQGT-NGQNGN--VHLNGIASTLDDPRVGGKTAHLIKEISDTERN--RAASVGDVLNA....
..L..T.NG.....S..-...............T.TLA.T.G.VDTN.DAVNYH-......Q...S.
..L..T.NG...............-........T.TIT.MT.QASNGVAVQ-NH--.........A.
..L..T.NG...............-........T.TIT.MT.QASNGVAVQ-NH--.........A.
......PS.-...............-........T.TIT.TTKSATNGVDVQNH-.........A.
.....DAA--..A..DIT.......G...T.TK..SPAT.IDGGDQS.HYT--.....IK......
..V....GA.GANGDIT-....TN......Q.TLLNTGVSKLLDGNGITADEKK......Q...S.
.........DSKT-..DDA..--I..........T.TLLNSGATTNLGGNGITDNEKK.......K.
.........x..DSKT-..DDA..--I..........T.TLLNSGATTNLGGNGITDNEKK.......K.
......P.-...
     210       220       230       240       250
```

FIG. 28R

```
         ...TLSGDIQTAKGASQANNSAGYVDADGNKVIYDSTDNKYYQA...
         ...TLSGDIQTAKGASQASSSASYVDADGNKVIYDSTDNKYYQV...
* ***  * ***  ***  *                          **  *
        260       270       280       290       300
        ...QMNIRGAK--TIGG-TVDNDFVSTYDIVEFASGANANVSVTTDDN--    33
        ...Q.NGNNVDFVR.Y.T...N------............A.TAH-       32
        ...Q.NGASVDFVNAY.T...N------.......T.T..N....TAH-    29
        ...Q.NGASVDFVNAY.T...N------.......T.T..N....TAH-    K22
        ...Q.NGAS--------...N......D.VN.L.T.N....TAHN        M4071
        ...K.V.AGSTT-GQSE.....H.......L..DIETTTV.V.S--       11
        ...K.V.TGAT---.S.....R.......L.SEETTL..V.S--         K9
        ...V..V.PASANNQ-.E.I..A.....D.V..DKDTT...VES---      HSF
        ...V..V.PASANNQ-.E.I..A.....D.V..DKDTT...VES---      API
                       -.-..................-.-             Rd
        ...KNDGTVD.TKEVAKDKLVAQAQTPDGTLAQMNVKSVI.KEQVN.A.--  4223
        ...NDKGQVD.NKEVAKDKLVAQAQTPDGTLAQMNVKSVI.KEQVN.A.--  LES-1
                                     *
        310       320       330       340       350       360
KKITVRVDVTGLPVQYVTEDSKTVVKVGNEYYEAKQDGSADMDKKV-ENGKLAKTKVKLVSA...
.................G......K..D......NQ.--..E.-...
.................G......D.K................E...
.................G......D.K................E...
................GE..............................
...............F......G.........................-K..E.V.
```

FIG.28S

```
                                                                                                        33
. ENGK. TE. KIGAKTS. IKEKDGKLFT. KANK. TNKVDG. NATEDA-DE. . GLV. AKDVID. . . . .
ESNGKSTK. KIGAKTSGIKEKDGKLFT. KANKDIN. VASNNAADT-DE. GLV. AETVIN. . . . .                               32
. DNGK. TE. KIGAKTS. IK. HNGKLFT. K. LKD. NNN. VTVTETDGKDE. NGLV. AKAVID. . . . .                       29
. DNGK. TE. KIGAKTS. IK. HNGKLFT. K. LKD. NNN. VTVTETDGKDE. NGLV. AKAVID. . . . .                       K22
                                                                                                        M4071
. . QGINEDNAFVKGLEKAASDNKTKNAAVTVGDLNAVAQTPLTFAG-DT. TT. . KLGETLTI                                     12
. . QGINEDNAFIKGLENAAKDTKTKNAAVTVGDLNAVAQTPLTFAG-DT. TT. . KLGETLTI                                     11
 *                                                    *                                                K9
              370       380       390       400                                                         HSF
. . . NGTNPVKISNVADGTEDIDAVSFKQLKALQDKQVTLSAS                                                           API
. . . . . . . . . . . S. . . . . . . . . . . . . . . . . . . . . . . . T. .                            Rd
. . . S. Q. . . . . . . . . . . . . . E. EN. . . . . . . . T. . .                                      4223
. . . S. Q. . . . . . . . . . . . . . E. EN. . . . . . . . T. . .                                      LESS-1
. . . . . . . . . . . . . . . . . . . . . . . E. . . . . . . N. . . . . . .
. . . VNKTGMR. KTTDANGQNG. ---FATVASGTNVTF-----.
. . . VNKAGMR. KTTGANNQAGQ---FETVTSGTNVTF-----. D
. . . VNKAGMRVKTTGANGQND. ---FATVASGTNVTF-----. D
. . . VNKAGMRVKTTGANGQND. ---FATVASGTNVTF-----. D
. . . KGGQTDTNKLTDNNIGVVAGTDGFTV. LAK. LTNLN. VN
. . . KGGQTDTNKLTDNNIGVVAGTDGFTV. LAK. LTNLN. VN
                                           *
   410       420       430       440       450       460
```

FIG.28T

```
NAYANGGSDADGKATQILGNDLNFFKSTDSELLNIKAAGDTVTFTPKKGSVQVGDDGKAT...         33
.....T.N........S.G........S.G...K.S.T............S........         32
........N.......N.G.........G......VEN....E...............         29
........N.......N.G.........G......VEN....E...............         K22
..............GI..S.G.........G.......EN..................         M4071
........V.V...S.G.........G.......DK....I..--.............         12
                                                                    11
GNGITATVING--TDGITVKYDAKVGDGLKLDGD-KLAADTTALTVNDGKNANNPKGKVADVA...    K9
GNGTTAVVTGDATNGITVKYEAKVGDGLKIGNDQKITADTTALTVTGGK------VTAPD...     HSF
GNGTTAEVTKANDGSITVKYNVKVADGLKLDGD-KIVADTTVLTVADGK------VTAPN...     API
GNGTTAEVTKANDGSITVKYNVKVADGLKLDGD-KIVADTTVLTVADGK------VTAPN...
...............G...S.G.........G.......EN.................

AGGIKIDDKGVSF--............................................
AGGIRIDEKGISFVDANGQAKANTPVLSANGLDLGKRISNIGAAVDDNDAVNFKQFNEVAK...
                                                     *
                           470       480       490       500
                    ..IQDGAKTTTGLVEASELVDSLNKLGWKVGVGKDGTG---AT
                    ...SK.N..E.............E......E.V.S.---EL
                    ....N.T...D..............E.......D..S.---EL
                    ....N.T...D..............E.......D..S.---E.
                    ..................................T.T....V.---
                    ---------------------------------------------
                    ...STDEKK----...T.KG..TA..S.S.TTTAAEADG.---TL
                    ...AINGKK----...N..G.A.A....S.TAK-AEADTANGEL
                    ...NGDGKK----..F.D..G.A.A....S.TATA..E....---EV
                    ...NGDGKK----..F.D..G.A.A....S.TATA..E....---EV
```

FIG.28U

```
                                                                           Rd
                                          ...TVNNINQSNSGASLPFVVTDANGKPIN.TDCKPQKAIKGA    4223
                                          ---------------------------------------       LES-1
                                                            *
              510       520       530       540       550       560
DGIHID-TLVKSGDKVTLKAGDNLKVKQEGINFTYVLRDELTGVKSVEFKDTENGANGASTK...
...SKE-............................A.K...........A.........
..ASNE-.........E........D......A.K...........A...S........
..ASNE-.........E........D......A.K...........A...S........
   -..................................A.K...D.....A.........
.NASE-QE..A......F..K.........A....S.Q.A....LT.ITLGTGN...K---..E...
.ADE-KE..A.ET.F..K.........A....S.Q.A....LT.ITLGTGN...K---..E...
.PANSAGQE..A......F.......I..S.KD...S.KK..KDLT........ANG.TGSE.....
.PANSAGQE..A......F.......I..S.KD...S.KK..KDLT........ANG.TGSE.....
-......................................................................
                                                                                33
                                                                                32
                                                                                29
                                                    ...ANGVP.....               K22
                                                       * * *
              570       580       590       600
...ITKDGLTITPAND-ANGAAATDADKIK---VASDGISAGNKAV
....L..G-.....TV..----------------
....S..G-.........----------------
....S..G-.........----------------
..KYH--------------------------------
**
```

FIG. 28V

```
                                                                                    M4071
                          ......................G-.GA.G.NT.NT.S----.TK.............   12
                          ---------R.SG-........:--............................:...    11
                          ...N..................G-.---G.NN.NT.S---.TK......DQS.....    K9
                          ...N..................G-.---G.NN.NT.S---.TK......DQS.....    HSF
                          ..........................G-.GA.G.NT.NT.S---.TK............ API
                          ..........................G-.GA.G.NT.NT.S---.TK............ Rd
                          .....................................R..................    4223
                          ......F...G-.............................................    LES-1
                          ...VD...KP..D.DKL..L..HGKPLDAGHQV...L.-GNSD-.I
                           .:.**** *** * **                   ** ****  **

610       620       630       640       650       660
KNVVSGLKKFGDANFNPLTSSADNLTKQYDNAYKGLTNLDEKSKGKQTPTVADNTAATVGDL...
................................................................
..................D................GAD..L.....................
..................D................GAD..L.....................
..................D...............................GAD..L........
..................D..............N.D.............GTD...V.......
..................D.................GAD..L.......GADNN-........
...............GHTLANGTV..FE-.H......D.........GADNN-..........
T..............GHTLANGTV..FE-.H......XD.........GADNN-..........
T..-----TLTNIKSTLP.I.TPNT.NA.AGQAQSLPSLSAAQQSN..S.K.V...
```

FIG.28W

```
            *          *  **  *    *     * ****  **
                   670         680        690        700
         ...TGLGWVISADKTIGES-KEYSAQVRNANEVKFKSGNGIN    33
         .........................IN..N...........    32
         .........................IN..N.........H.    29
         .........................IN..N.........H.    K22
         ........................K.IN..N..........    M4071
         ..........................................   12
         .................G.-T..HD.................   11
         ......................LD..N...............   K9
         ......................PNQ.N...............   HSF
         ......................PNQ.N...............   API
         ..........................................   Rd
         ..........................................   4223
         ...LNV.FNLQTNHNQVDFV.A.DTVNFVNGTGADITSVRSA    LES-1
              ***.* .***                       **

710        720        730        740        750        760
         VSGKTLDNGTREITFELAKDENAIAFGSGSKALRDNTVAIGTGNVVNAEKSGAFGDPNYIED...
         ----V-..R.....................Y..................................
         ----V-..R.....................Y..................................
         |--------------------------------------------------------------|
         ..................................................................
         ..................................................................
         ..................................................................
         |--------------------------------------------------------------|
         ......V-..R............G.-------------------------------------
```

FIG.28X

```
         .....V-..R.........G.---    ...............................................    33
         -.........V.........G.---    ...............................................    32
         -.........V.........G.---    ...............................................    29
         --------------------    ...............................................    K22
DGIMSNITVNTALAATDDDGNVL.KAKD.KFYKA.DLMPN.SLKAGKSASDAKTPIGLSLVN...    KAGGSYAFGNDNRITSKNTFVLGNGVNAKYKANGKVDT----    M4071
 ***      **      *       **   **       *      *         *       ****        *         *       *     12
         :         :         :         :         :         ........S....RD..N.L.EE---    11
         770       780       790       800    ...............................................    K9
                                                ...............................................    HSF
                                                ...............................................    API
                                                ...............................................    Rd
                                                ...PNA.KGST.DAVALNNLSKA.FKSKDGTTTTTVSSDGISIQGK    4223
                                                    ***   ****        *      *                    LES-1
```

FIG.28Y

```
                                                                          33
                                                                          32
                                                                          29
..VVKSNEFTVKEINGKETSLVKVGDLYYSKEDIDLTTGQPKLKDGNIVAAKYQDKGGKVVS-V...        K22
..VVKSNEFTVKEINGKETSLVKVGDLYYSKEDIDPATGKPKVTNGNAVAAKYQDKDGKVVSAD...       M4071
..VVKSNEFTVKNADGSETNLVKVGDLYYSKEDIDPATSKPMIGKTE----KYKVENGKVVSAN...TDNTEATTINKGSGYVIGNQ---         12
..VVKSNEFTVKNADGSEINLVKVGDLYYSKEDIDPATSKPMIGKTE----KYKVENGKVVSAN...GSSNTAVTLINKGYGYVIGNQ---        11
                                                                  ...GSK-TEVTLIMKGSGYVIGNQ---         K9
VDSSGQAKANTPVLSANGLDLGGKVISNWGKTKDTDAANVQQLNEVRNLLGLGNAGNDNAD...GSK-TEVTLIMKGSGYVIGNQ---          HSF
DNSSI------TLSKDGLNWGGKVISNWGKTKDTDAANVQQLNEVRNLLGLGNAGNDNAD...                                  API
   **                                          *      *                                         Rd
                                                                  ...GNQVNIADIKKDPNSGSSSNRTVIKAGTVLGGKGNNDT   4223
                                                                  ...GNQVNIADIKKDPNSGSSSNRTVIKAGTVLGGKGNNDT   LES-1
```

FIG. 28Z

```
VADAIAKSGFEKGKADEADAKRAFDD--KTKALSAGITE-TVNAHDKVRFANGLNTKVSAAT...         33
VADAIAKSGFFEKGKADAEKAKAAFGD--ETKALSSDKLE-TVNANDKVRFANGLNTKVSAAT...        32
VADAIAKSGFEKGKADAAEAAEKAFAEKAFAESAKDKQLSKDKAE-TVNAHDKVRFANGLNTKVSAAT...   29
VADAIAKSGFEKGKADAAEAEFAEKAFAESAKDKQLSKDKAE-TVNAHDKVRFANGLNTKVSAAT...      K22
                                                                          M4071
EKLATGGIQVGVDKIGNANGDLSNVWKTQKQGSKKALLATYNAAGQINYLINNPAEAIDRI...          12
EKLATGGVQVGVDKIGNANGDLSNVWKTQKQGSKKALLATYNAAGQINYLINNPAEAIDRI...          11
                                                                          K9
                                                                          HSF
...VESTDANGDKVTTIFVKTDVELPLTQIYNTDANGKKITKVV                              
...VESTDANGDKVTTIFVKTDVELPLTQIYNTDANGKKI---V                              
...VESTDANGDKVTTIFVKTDVELPLTQIYNTDANGKI---V                               
```

FIG.28A'

```
                                                                          ...VESTDANGDKVTTFVKIDVELPLTQIYNIDANGNKI---V    API
                                                        ...NEQGIRFFHVNDGNQEPVVQGRNGIDSSASGKHSVAIGFQ-            Rd
                                                        ...NEQGIRFFHVNDGNQEPVVQGRNGIDSSASGKHSVAIGFQ-            4223
                                                                  *  **                                        LES-1

KDGQTKWYEINADGTADMKEVTLGWDSDGKKVVKIDG----KWYHAKADGTADKITKGEVD...                                              33
KNGD-KWYYTKDDGSTDMKEVTLGWDSDGKKVVKEDN----KWYGVKSDGSTDKIQVVEE...                                              32
KKADGKWYEINADGTASN-KEVTLGWDANGKKVVKVTENGADKWYTNADGAADKITKGEVS...                                              29
KKADGKWYEINADGTASN-KEVTLGWDANGKKVVKVTENGADKWYTNADGAADKITKGEVS...                                              K22
                                                                                                              M4071

AKADGEAAVAIGRQTQAGNQSIAIGINAQATGDQSIAIGINVVAGKHSGAIGDPSTVKADN...
AKADGEAAVAIGRQTQAGNQSIAIGINAQATGDQSIAIGINVVTGKHSGAIGDPSTVKADN...
   **                                                    *
```

FIG.28B'

```
                                                                                                              12
                                                                                                              11
                                                                                                              K9
                                                                                                              HSF
                                                                                                              API
                                                                                                              Rd
                                                                                                              4223
                                                                                                              LES-1

33
                                                                                                              32
                                                                                                              29

810       820       830       840       850       860       870       880       890       900
ETVTVKDGKETTVTVPKALGATVENSVYLGNKSTATKDGKNLKSDGTAGNTTAGTTGT...
..........................................NDKVSTDEKHVVSLDPNDQSKGKGVV
..........................................A-KVSTDEKHVVSLDPNDQSKGKGVV
..EKE.VG..AK.K......Q..E..............................NDKVSTDEKHVVSLDPNDQSKGKGVV
..........................................NDKVSTDEKHVVSLDPNDQSKGKGVV
..............................A...........................................
........................................T....A..............
........................................T....A..............
  *    *   **                              *******************
VTESNSVAL.SNSAISAGTHA.TQAK-.........SYSVGNNQGIDATQIDVFGVGNNIT
VTESNSVAL.SNSAISAGTHA.TQAK-.........SYSVGNNQGIDATQIDVFGVGNNIT
                                    **  **                 *

VNGFAGATAHGAVSVGASGEERRIQNVAAGEISATSTD
                                                       ...........K.........................
```

FIG.28C'

```
                                                                                              K22
                                                                                              M4071
                                                                                              12
                                                                                              11
                                                                                              K9
                                                                    ..D..N.D..........         HSF
                                                                    N.M.N..............        API
                                                                    ..D..N..............       Rd
                                                                    ..D..N..............       4223
                                                                    .....K..............       LES-1
                                        K...Q..V.......A.........V.....
                                        K...Q..V.......A.........V.....
                                        *.****.**.*********.****.***.*********

910       920       930       940       950
AINGSQLYAVAKGVINLAQOVN------KVGKRADAGTASALAASQLPQASMSGKSMVSIA..       K22
..........NLEGKVN.............T.P...................               M4071
-------------------...........P.....................               12
-------------------...........P.....................               11
-------------------...........P.....................               K9
..........NLEGKVN.............P.....................               HSF
..........NLEGKVN.............T.P......A............               API
..........NLEGKVN.............T.P......A............               Rd
..........NLEGKVN.............T.P......A............               4223
-------------------...........P.....................               LES-1
 *********  **    *     *****  *   ******* * **** *

V........ATQSI.NAT.ELDHRIHQNENK.N..IS..M.MASM..YIP.R...TGG.
V........ATQGI.NAT.ELDHRIHQNENK.N..IS..M.MASM..YIP.R...TGG.
*********      *****  ***** ***** *
```

FIG. 28D'

```
         960         970         980         990        1000
...GSSYQGQSGLAIGVSRISDNGKVIIRLSGTINSQGKTGVAAGVGYQW*              33
   .................N.................................*         32
   ......................................................*      29
   ......................................................*      K22
   ......................................................*      M4071
   ...................L..................................*      12
   .................N....................................*      11
   .................N....................................*      K9
   .................N....................................*      HSF
   .................N....................................*      API
   .................N....................................*      Rd
   ...IATHN.GAV.V.L.KL....QWFKIN.SADT..HV.A.V.A.FHF*              4223
   ...IATHN.GAV.V.L.KL....QWFKIN.SADT..HV.A.V.A.FHF*              LES-1
   ******  *************  ********  *  *******  * ** *****  *
```

FIG. 29
Oligonucleotides primers to PCR amplify truncated strain 11 S44 hia gene.

```
        NdeI
        M  S44A  T  V  E  A  N  N  N  T
5' GGGAATTCATATGTCCGCAACGGTTGAGGCAAACAACAATACT 3'      6817.SL    SEQ ID NO:56
                                                                  SEQ ID NO:55

StyI
        H  T  I  T  F  A  L  A  K  D  L  G
   CACACCATTACTTTGCTTTAGCTAAAGACCTTGGT
3' GTGTGGTAATGAAACGAAATCGATTTCTGGAACCACCCTAGGGC 5'     6818.SL    SEQ ID NO:59
                                                                  SEQ ID NO:58
                                                                  SEQ ID NO:57
```

Production of S44 rHia from different vectors 1. pET S44 hia            $t_0$
2. pET S44 hia            $t_4$
3. pBR T7 S44 hia/cer/kanR  $t_4$ pBR T7 S44 hia/cer/KanR        pET S44 hia

RECOMBINANT *HAEMOPHILUS INFLUENZAE* ADHESIN PROTEINS

REFERENCE TO RELATED APPLICATIONS

"This application is a national phase application under 35 U.S.C. 371 of PCT/CA00/00289. This application is a continuation-in-part of U.S. patent application Ser. No. 09/268,347 filed Mar. 16, 1999, now U.S. Pat. No. 6,335,182 issued Jan. 1, 2002."

FIELD OF INVENTION

The present invention relates to the field of molecular genetics and, in particular, to the production of recombinant *Haemophilus influenzae* adhesin (Hia) proteins.

BACKGROUND TO THE INVENTION

*Haemophilus influenzae* is the cause of several serious human diseases, such as meningitis, epiglottitis, septicemia and otitis media. There are six serotypes of *H. influenzae*, designated a to f, that are identified by their capsular polysaccharide. *H. influenzae* type b (Hib) was a major cause of bacterial meningitis until the introduction of several Hib conjugate vaccines in the 1980' s (ref. 1. Throughout this application, various references are referred to in parenthesis to more fully describe the state of the art to which this invention pertains. Full bibliographic information for each citation is found at the end of the specification, immediately preceding the claims. The disclosures of these references are hereby incorporated by reference into the present disclosure). Vaccines based upon *H. influenzae* type b capsular polysaccharide conjugated to diphtheria toxoid (ref. 2), tetanus toxoid (ref. 3 and U.S. Pat. No. 4,496,538), or *Neisseria meningitidis* outer membrane protein (ref. 4) have been effective in reducing *H. influenzae* type b-induced meningitis. The other serotypes of *H. influenzae* are associated with invasive disease at low frequencies, although there appears to be an increase in the incidence in disease caused by these strains as the incidence of Hib disease declines (ref. 5; ref. 6). Non-encapsulated or non-typeable *H. influenzae* (NTHi) are also responsible for a wide range of human diseases including otitis media, epiglottitis, pneumonia, and tracheobronchitis. The incidence of NTHi-induced disease has not been affected by the introduction of the Hib vaccines (ref. 7).

Otitis media is the most common illness of early childhood, with 60 to 70% of all children, of less than 2 years of age, experiencing between one and three ear infections (ref. 8). Chronic otitis media is responsible for hearing, speech and cognitive impairments in children. *H. influenzae* infections account for about 30% of the cases of acute otitis media and about 60% of chronic otitis media. In the United States alone, treatment of otitis media costs between 1 and 2 billion dollars per year for antibiotics and surgical procedures such as tonsillectomies, adenoidectomies and insertion of tympanostomy tubes. It is estimated that an additional $30 billion is spent per annum on adjunct therapies, such as speech therapy and special education classes. Furthermore, many of the causative organisms of otitis media are becoming resistant to antibiotic treatment. An effective prophylactic vaccine against otitis media is thus desirable.

During natural infection by NTHi, surface-exposed outer membrane proteins that stimulate an antibody response are potentially important targets for bactericidal and/or protective antibodies and, therefore, potential vaccine candidates. A family of high molecular weight proteins (HMW1 and HMW2) that are important in attachment of NTHi to epithelial cells has been identified in about 70 to 75% of NTHi strains (ref. 9; ref. 10). These high molecular weight adhesins have been shown to afford some protection in the chinchilla model of otitis media (ref. 11). A second family of high molecular weight adhesion proteins has been identified in about 25% of NTHi and in encapsulated *H. influenzae* strains (ref. 12; ref. 13, ref. 14). The NTHi member of this second family is termed *Haemophilus influenzae* adhesin or Hia and the homologous protein found in encapsulated strains is termed *Haemophilus influenzae* surface fibril protein or Hsf. The hia gene was originally cloned from an expression library using convalescent sera from an otitis media patient, which indicates that it is an important immunogen during disease. The prototype Hia and Hsf proteins demonstrate about 82% sequence similarity, although the Hsf protein is considerably larger. The proteins are comprised of conserved amino and carboxy termini and several repeat motifs, with Hsf containing more repeat sequences than Hia. A high molecular weight protein (200 kDa) has also been identified from *Moraxella catarrhalis* that has some sequence homology with the Hsf and Hia proteins (U.S. Pat. No. 5,808,024).

Since Hia or Hsf is conserved amongst encapsulated strains of *Haemophilus influenzae* and about 20 to 25% of non-encapsulated strains, and has been demonstrated to be an adhesin, the protein has utility in diagnosis of and vaccination against disease caused by *H. influenzae* or other bacterial pathogens that produce Hia or a protein capable of raising antibodies specifically reactive with Hia.

A disadvantage of Hia for use as an antigen in diagnosis, for the generation of anti-Hia antibodies useful in diagnosis and as an immunogen in vaccination is the low recovery of the native protein from *Haemophilus influenzae* species.

It would be advantageous to provide recombinant Hia protein for use as antigens, in immunogenic preparations including vaccines, carriers for other immunogens and in the generation of diagnostic reagents.

SUMMARY OF THE INVENTION

The present invention is directed towards the provision of recombinant *H. influenzae* adhesin (rHia) proteins.

In connection with the provision of such recombinant proteins, the present invention provides certain isolated and purified nucleic acid molecules. Accordingly, in one aspect thereof, the present invention provides an isolated and purified nucleic acid molecule encoding a *Haemophilus influenzae* adhesin (Hia) protein of a strain of *Haemophilus influenzae* having: (a) a DNA sequence selected from the group consisting of those shown in FIGS. 18, 19, 20, 21, 22, 23, 24 and 25 (SEQ ID Nos: 23, 25, 27, 29, 31, 33, 35, 37); or (b) a DNA sequence encoding a *Haemophilus influenzae* adhesin (Hia) protein having an amino acid sequence selected from the group consisting of those shown in FIGS. 18, 19, 20, 21, 22, 23, 24 and 25 (SEQ ID Nos: 24, 26, 28, 30, 32, 34, 36, 38).

Such nucleic acid may be included in a vector, which may be a plasmid vector. In particular, the nucleic acid molecule may encode the Hia protein from strain 11 or 33 of non-typeable *Haemophilus*.

In another aspect of the present invention, there is provided an isolated and purified nucleic acid molecule encoding an N-truncated *Haemophilus influenzae* adhesin (Hia) protein of a strain of *Haemophilus influenzae* which is amplifiable by a pair of nucleotides which are selected from the group consisting of SEQ ID No: 7 and SEQ ID No: 15; SEQ ID No: 9 and SEQ ID No: 15; SEQ ID No: 11 and SEQ ID No: 15; SEQ ID No: 13; SEQ ID No: 15; SEQ ID No: 49; and SEQ ID No: 51.

Such nucleic acid may be included in a vector, which may be a plasmid vector. In particular, the nucleic acid molecule may encode an N-truncated Hia protein from strain 11 or 33 of non-typeable *Haemophilus*, starting at codon V38 or S44.

The plasmid vector incorporating the isolated and purified nucleic acid provided in accordance with these aspects of the invention may have the identifying characteristics of a plasmid which is selected from the group consisting of:

DS-2008-2-3 as shown in FIG. 1A
DS-2186-1-1 as shown in FIG. 5A
DS-2201-1 as shown in FIG. 5A
DS-2186-2-1 as shown in FIG. 5A
DS-2168-2-6 as shown in FIG. 5A
1A-191-3-1 as shown in FIG. 32

The vector provided herein may include the cer gene from *E. coli*. Accordingly, in another aspect of the present invention, there is provided a vector for transforming a host, comprising a nucleic acid molecule encoding a full-length or N-truncated *Haemophilus influenzae* adhesin (Hia) protein, a promoter for expression of said full-length or truncated Hia protein and, optionally, the cer gene of *E. coli*. The vector may be a plasmid vector or other non-replicating vector, which may have the identifying characteristics of a plasmid vector which is selected from the group consisting of:

BK-96-2-11 as shown in FIG. 6A
DS-2242-1 as shown in FIG. 7A
DS-2242-2 as shown in FIG. 7A
DS-2340-2-3 as shown in FIG. 8A
DS-2447-2 as shown in FIG. 9A
DS-2448-17 as shown in FIG. 9B
JB-2930-3 as shown in FIG. 32

The vectors provided herein may comprise a replicating vector, including a vector from *Salmonella*, BCG, adenovirus, poxvirus, vaccinia or poliovirus.

Any of the vectors provided herein may be employed to transform a suitable host cell for expression therein of a protective *Haemophilus influenzae* adhesin (Hia) protein of a non-typeable strain of *Haemophilus*, which may be in full-length or truncated form. Such host conveniently may be *E. coli*. Such expression may be under the control of the T7 promoter and expression of the recombinant Hia from the transformed host may be effected by culturing in an inducing concentration of lactose or other convenient inducing agent.

The present invention further includes, in a further aspect thereof, a recombinant protective *Haemophilus influenzae* adhesin (Hia) protein of a non-typeable *Haemophilus* strain producible by the transformed host, particularly *E. coli*, provided herein. Such Hia protein may be provided in the form of an immunogenic fragment or adhesin-functional analog of the recombinant protein.

The recombinant Hia proteins, full-length or N-truncated, provided herein are useful as antigens in immunogenic compositions, carriers for other immunogens, diagnostic agents and in the generation of diagnostic agents. The nucleic acid molecules which encode the Hia protein, full-length or N-truncated, also are useful as probes for diagnostic use and also in immunogenic compositions.

The present invention, in an additional aspect thereof, provides an immunogenic composition, comprising at least one immunologically active component which is selected from the group consisting of an isolated and purified nucleic acid molecule as provided herein and a recombinant protective Hia protein, full-length or N-truncated, of a strain of *Haemophilus*, as provided herein, and a pharmaceutically-acceptable carrier therefor.

The immunogenic compositions provided herein may be formulated as a vaccine for in vivo administration to a host to provide protection against disease caused by *H. influenzae*. For such purpose, the compositions may be formulated as a microparticle, capsule, ISCOM or liposome preparation. The immunogenic composition may be provided in combination with a targeting molecule for delivery to specific cells of the immune system or to mucosal surfaces.

The immunogenic compositions of the invention (including vaccines) may further comprise at least one other immunogenic or immunostimulating material and the immunostimulating material may be at least one adjuvant or at least one cytokine. Suitable adjuvants for use in the present invention include (but are not limited to) aluminum phosphate, aluminum hydroxide, QS21, Quil A, derivatives and components thereof, ISCOM matrix, calcium phosphate, calcium hydroxide, zinc hydroxide, a glycolipid analog, an octadecyl ester of an amino acid, a muramyl dipeptide, polyphosphazene, ISCOPREP, DC-chol, DDBA and a lipoprotein and other adjuvants.

Advantageous combinations of adjuvants are described in copending U.S. patent application Ser. No. 08/261,194 filed Jun. 16, 1994 and 08/483,856 filed Jun. 7, 1995, assigned to the assignee hereof and the disclosure of which is incorporated herein by reference (WO 95/34308 published Nov. 21, 1995).

In accordance with another aspect of the invention, there is provided a method for generating an immune response in a host, comprising the step of administering to a susceptible host an effective amount of the immunogenic composition as recited above. The immune response may be humoral or a cell-mediated immune response. Hosts in which protection against disease may be conferred include primates, including humans.

In accordance with other aspects of the invention, there is provided the immunogenic compositions provided herein when used as a medicament and the use of these components of the immunogenic compositions in the manufacture of an immunogenic composition.

The present invention includes, in a yet additional aspect thereof, a method for the production of a protective *Haemophilus influenzae* adhesin (Hia) protein of a non-typeable strain of *Haemophilus influenzae*, which comprises:

transforming a host, such as *E. coli*, with a vector comprising a nucleic acid molecule encoding an N-truncated form of the *Haemophilus influenzae* adhesin protein as provided herein, growing the host to express the encoded truncated Hia, and isolating and purifying the expressed Hia protein.

The encoded truncated Hia may be expressed in inclusion bodies. The isolation and purification step may be effected by disrupting the grown transformed cells to produce a supernatant and the inclusion bodies containing the Hia, solubilizing the inclusion bodies after separation from the supernatant, to produce a solution of the recombinant Hia, chromatographically purifying the solution of recombinant Hia free from cell debris, and isolating the purified recombinant Hia protein.

The vector transforming the host cell, such as *E. coli*, may include the T7 promoter and the *E. coli* or other host cell may be cultured in the presence of an inducing amount of lactose or other convenient inducing agent.

The strain of *Haemophilus influenzae* herein may be selected from the group of non-typeable strains consisting of strains 11, 33, 32, 29, M4071, K9, K22 and 12. Specific nucleic acid sequences for the genes encoding the respective Hia proteins from such strains are provided herein and are described below.

The nucleic acid molecules provided herein are useful in diagnostic applications. Accordingly, in a further aspect of the invention, there is provided a method of determining the presence, in a sample, of nucleic acid encoding a *Haemophilus influenzae* adhesin protein, comprising the steps of:

a) contacting the sample with a nucleic acid molecule as provided herein to produce duplexes comprising the nucleic acid molecule provided herein are nucleic acid encoding the Hia protein of a strain of *Haemophilus* present in the sample and specifically hybridizable therewith; and b) determining the production of the duplexes.

In addition, the present invention provides a diagnostic kit for determining the presence, in a sample, of nucleic acid encoding a *Haemophilus influenzae* adhesin protein, comprising:

a) a nucleic acid molecule as provided herein;

b) means for contacting the nucleic acid molecule with the sample to produce duplexes comprising the nucleic acid molecule and any such nucleic acid molecule; and c) means for determining production of the duplexes.

The recombinantly produced truncated Hia proteins provided herein also are useful in diagnostic applications. Accordingly, in another aspect of the invention, there is provided a method of determining the presence of antibodies specifically reactive with the Hia protein in a sample, comprising the steps of (a) contacting the sample with the recombinant Hia protein provided herein to provide complexes of the recombinant Hia protein and any such antibodies present in the sample specifically reactive therewith; and (b) determining production of the complexes.

Advantages of the present invention include:

an isolated and purified nucleic acid molecule encoding a *Haemophilus influenzae* adhesin protein or a fragment or an analog of the Hia protein;

recombinantly-produced Hia proteins, free from any other *Haemophilus* proteins; and diagnostic kits and immunological reagents for specific identification of *Haemophilus*.

BRIEF DESCRIPTION OF DRAWINGS

The present invention will be further understood from the following description with reference to the drawings, in which:

FIG. 4 shows the sites of truncation for the strain 11 Hia protein (SEQ ID No: 6).

FIG. 5B shows the oligonucleotides used to PCR amplify the 5'-fragments for the truncated genes. E21 truncation: Sense (5524.SL): SEQ ID No: 7, encoded amino acids SEQ ID No: 8; T33 truncation: Sense (5525.SL) SEQ ID No: 9, encoded amino acids SEQ ID No: 10; V38 truncation: Sense (5526.SL): SEQ ID No: 11, encoded amino acids, SEQ ID No: 12; N52 truncation: Sense (5527.SL): SEQ ID No: 13, encoded amino acids SEQ ID No: 14; Antisense (5528.SL): SEQ ID No: 15; complement SEQ ID No: 16, encoded amino acids SEQ ID No: 17.

FIG. 7B shows the oligonucleotides used to generate the 5'-end of the strain 33 hia gene coding strand (SEQ ID No.: 52), complementary strand (SEQ ID No.: 53), and encoded amino acid sequence (SEQ ID No.: 54).

FIG. 8B shows the oligonucleotides used to PCR amplify the 5'-end of the truncated hia gene. Sense (6286.SL). SEQ ID No: 60, encoded amino acids SEQ ID No: 61; antisense (6287.SL) SEQ ID No: 18, complement SEQ ID NO: 19, encoded amino acids SEQ ID No: 20.

Restriction enzyme sites are: B, BamH I; Bg, Bgl II; H, Hind III, Ps, Pst I, R EcoR I, S, Sal I, Xb, Xba I. Other abbreviations are, T7p, T7 promoter; ApR, ampicillin resistance, KanR, kanamycin resistance; CAP, calf alkaline phosphatase; tt1, transcription terminator 1 from trpA1 tt2, transcription terminator 2 from T1 gene 10.

Figure 10:
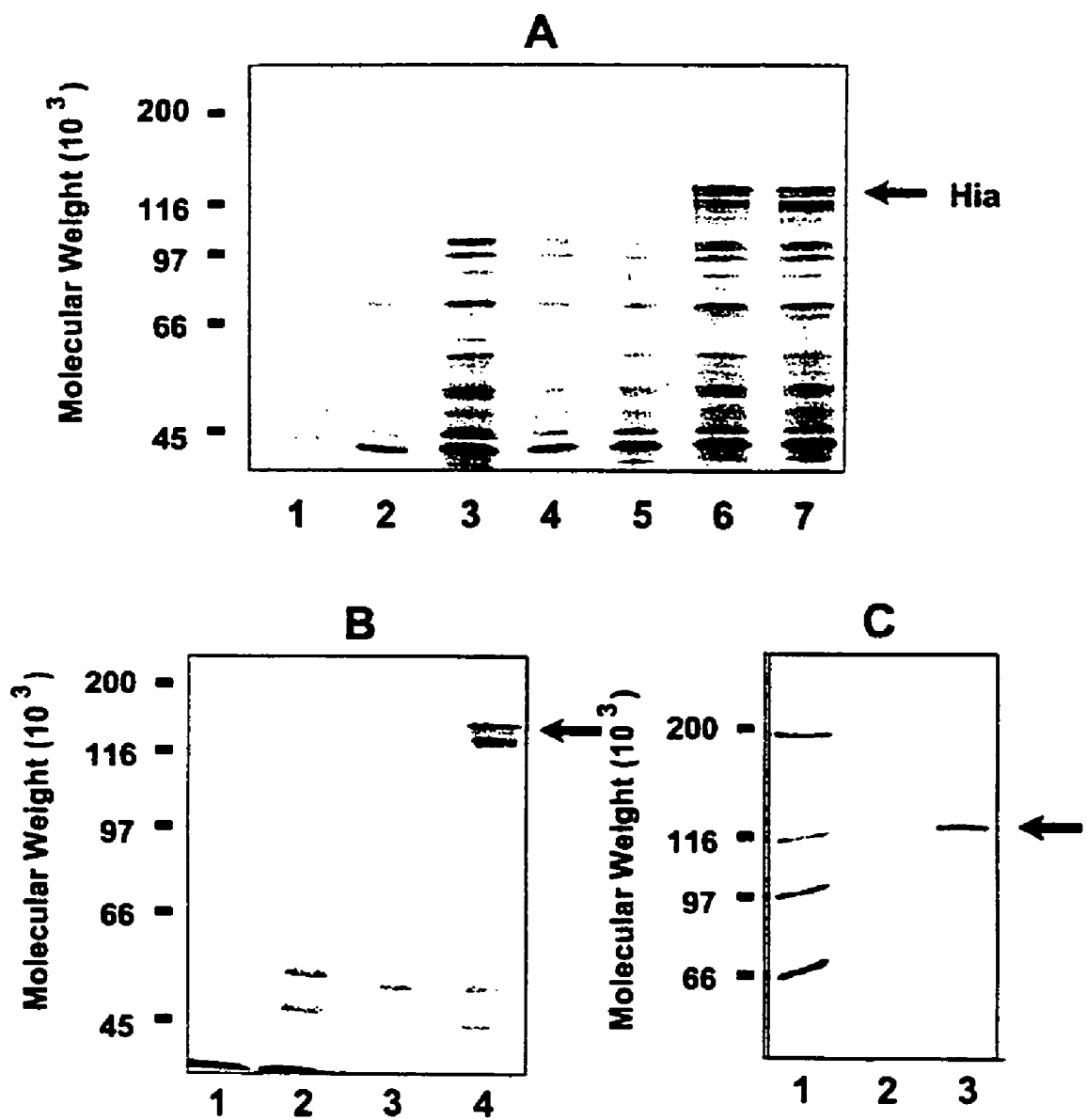

FIG. 10 shows the expression of rHia. Panel A: lane 1, full-length rHia (11) no induction; lane 2, full-length rHia (11) lane 3, E21 rHia (11), lane 4, T33 rHia (11), lane 5, V38 rHia (11), lane 6, N52 rHia (11). Panel B lane 1, V38 rHia (11) no induction; lane 2, V36 rHia (11); lane 3, V38 rHia (11)/cer.

Figure 11:
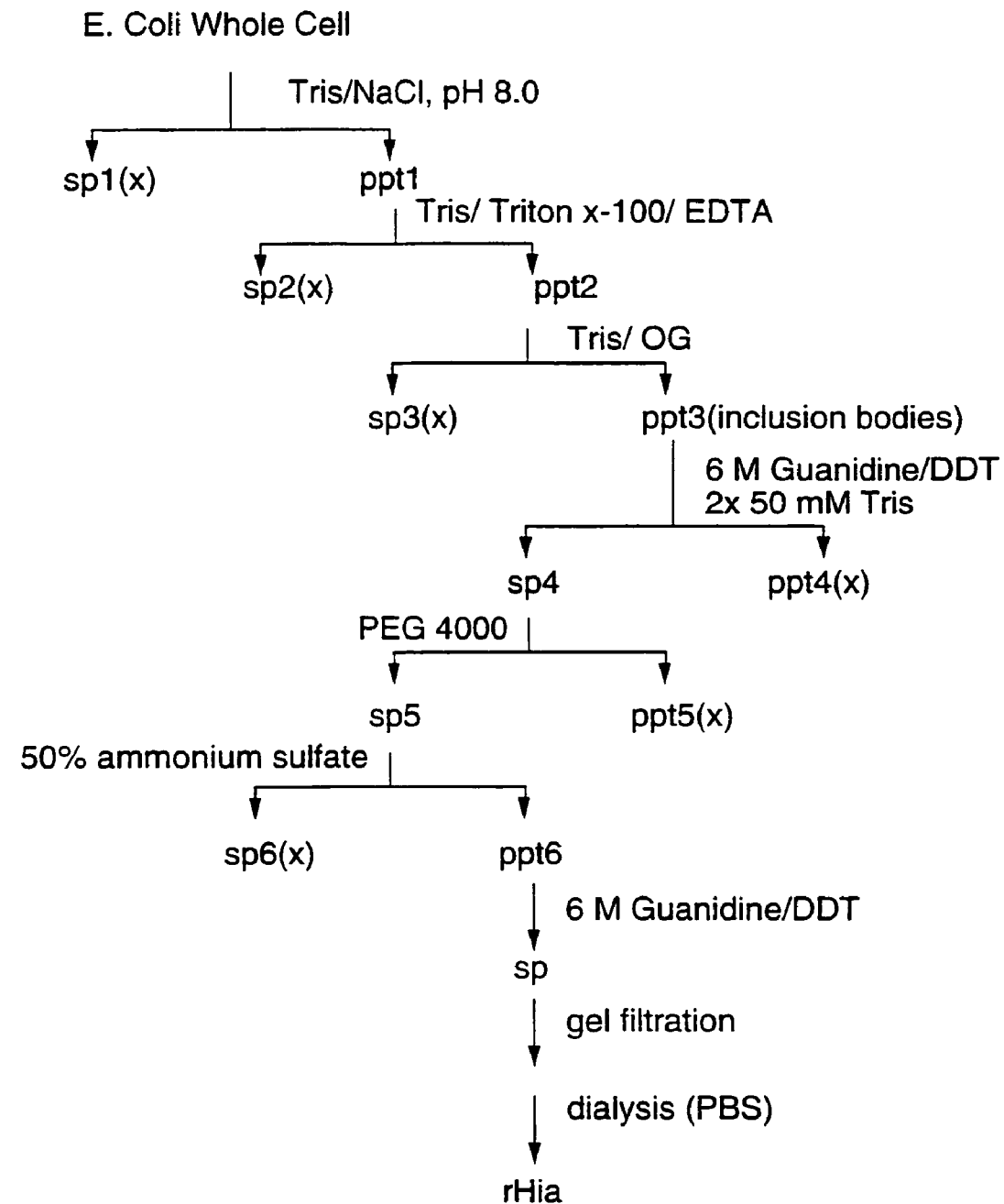

FIG. 11 shows a purification scheme for rHia proteins. Abbreviations are, SP, supernatant; precipitate; DTT, dithiothreitol; OG, octyl glucoside, (x) means discarded.

Figure 12:
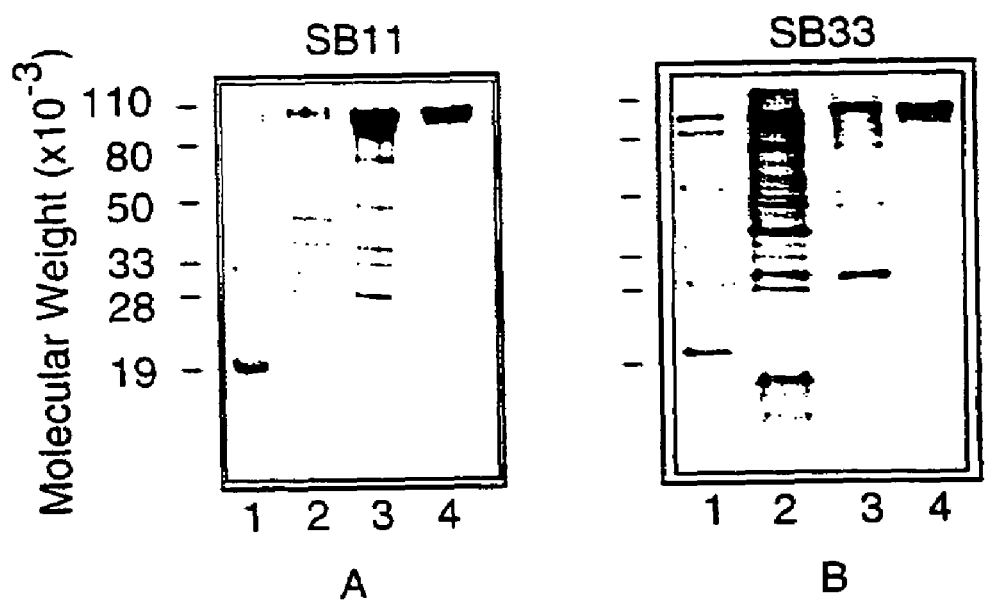

FIG. 12, having panels A and B, shows the SDS-PAGE analysis of purified rHia. Panel A shows purified V38 rHia protein from strain 11 and panel B shows purified V38 rHia protein from strain 33. Lane 1, molecular weight markers; lane 2, whole-cell lysate; lane 3, crude extract; lane 4, purified rHia protein.

Figure 13A:
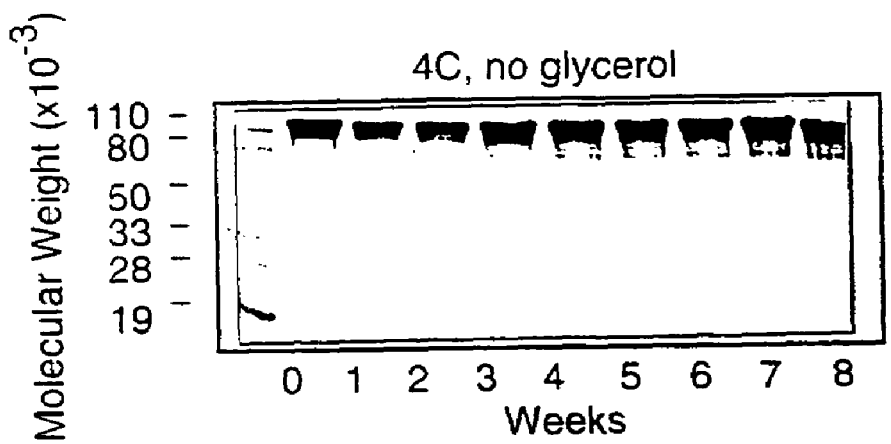
Figure 13B:
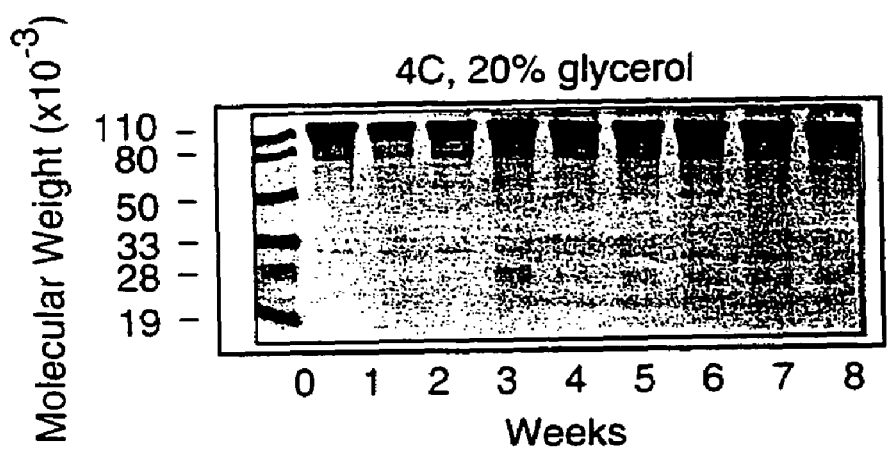
Figure 13C:
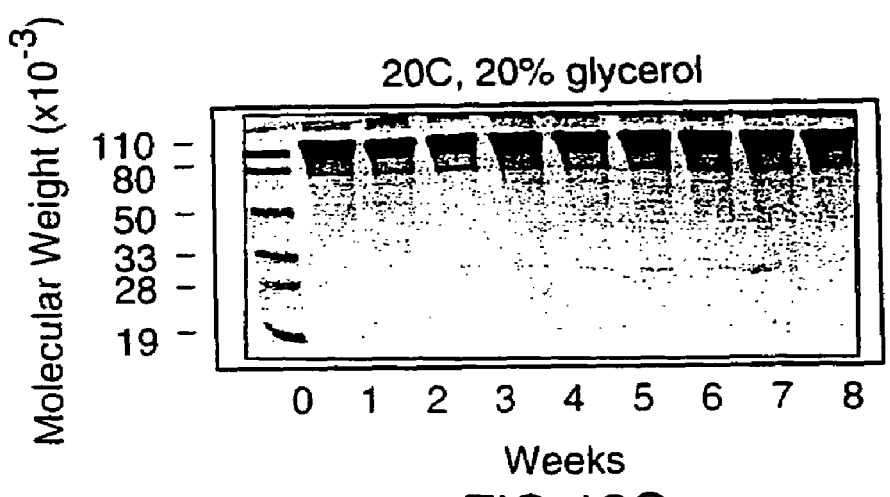

FIG. 13, having panda A, B and C, allows the stability of V38 rHia (11). Panel A shows samples stored at 4° C. without glycerol. Panel B shows samples stored at 4° C., in the presence of 20% glycerol. Panel C shows samples stored at −20° C. in the presence of 20% glycerol. Lane 0 indicates $t_0$; lanes 1 to 8 indicate samples stored for 1 to 8 weeks.

Figure 14A:
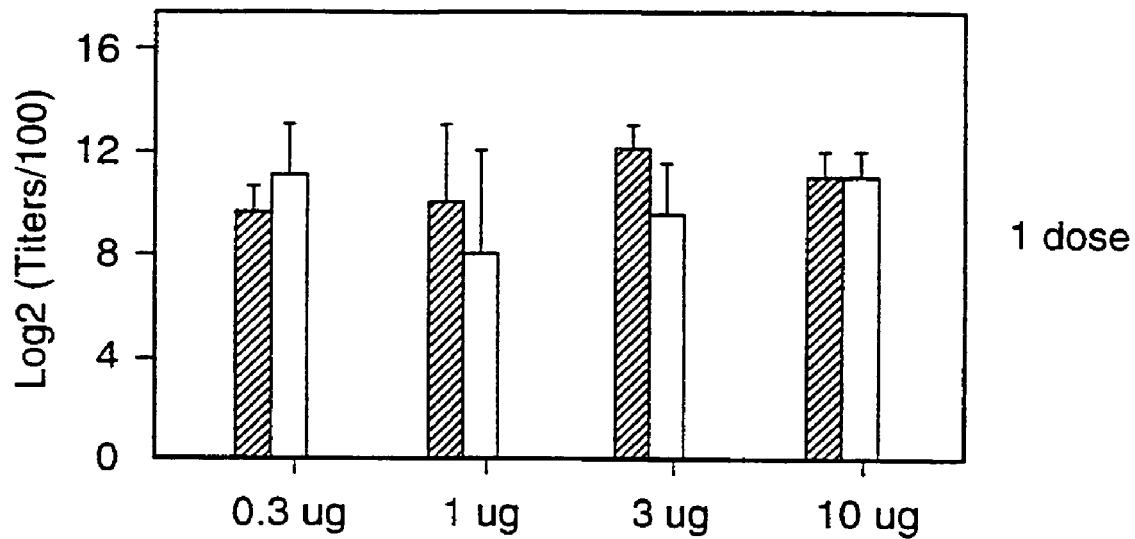
Figure 14B:
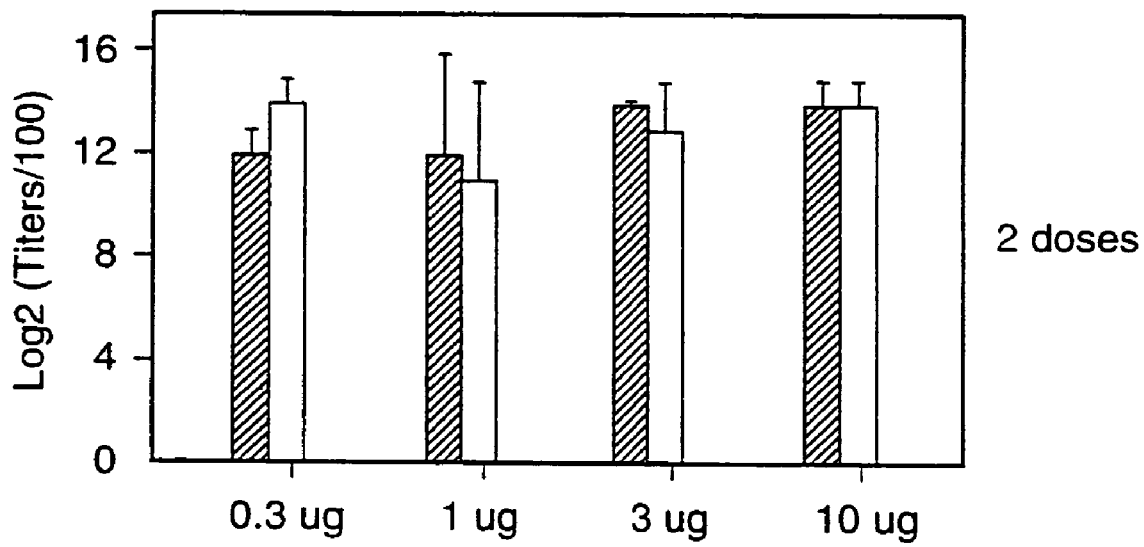

FIG. 14, having panels A and B, shows the immunogenicity of V38 rHia (11) or V38 rHia (33) in CD-mice. Panel A shows the response after a single immunization and panel B shows the response of a prime/boost immunization.

Figure 15A:
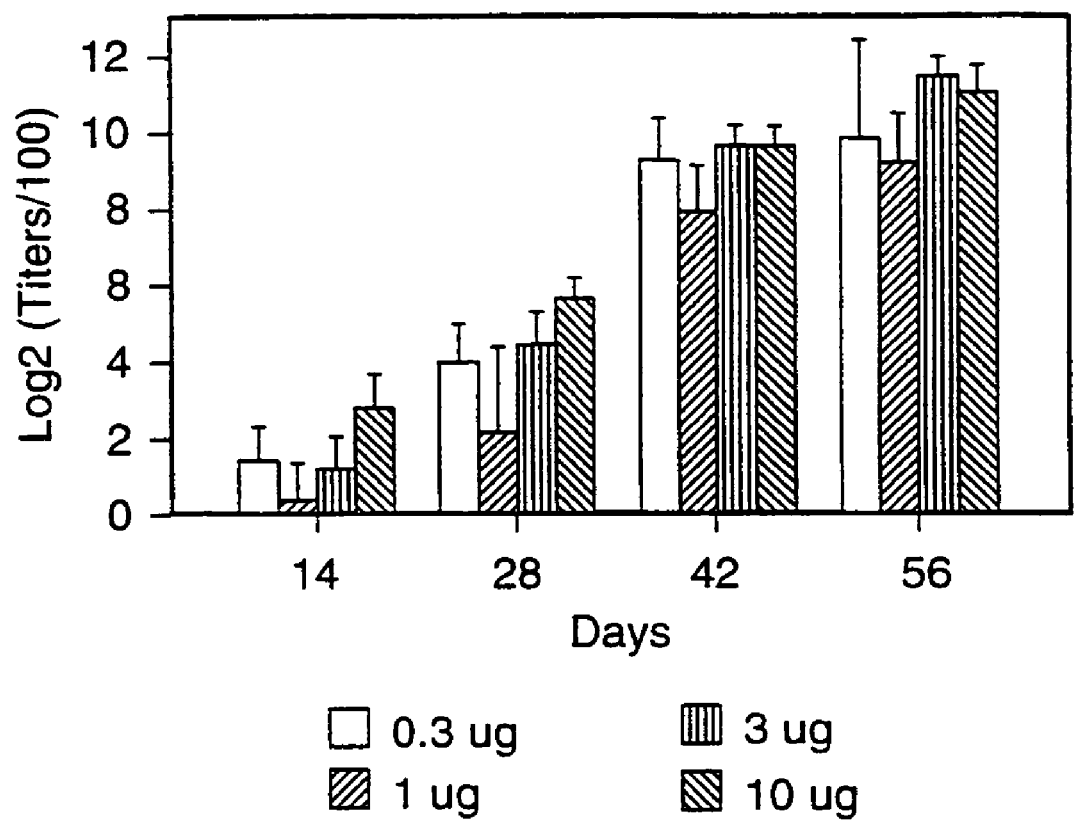

FIGS. 15A and 15B show the immunogenicity of V38 rHia (11) in BALB/c mice and guinea pigs. FIG. 15A shows the antibody response in mice and FIG. 15B shows the response in guinea pigs.

Figure 16:
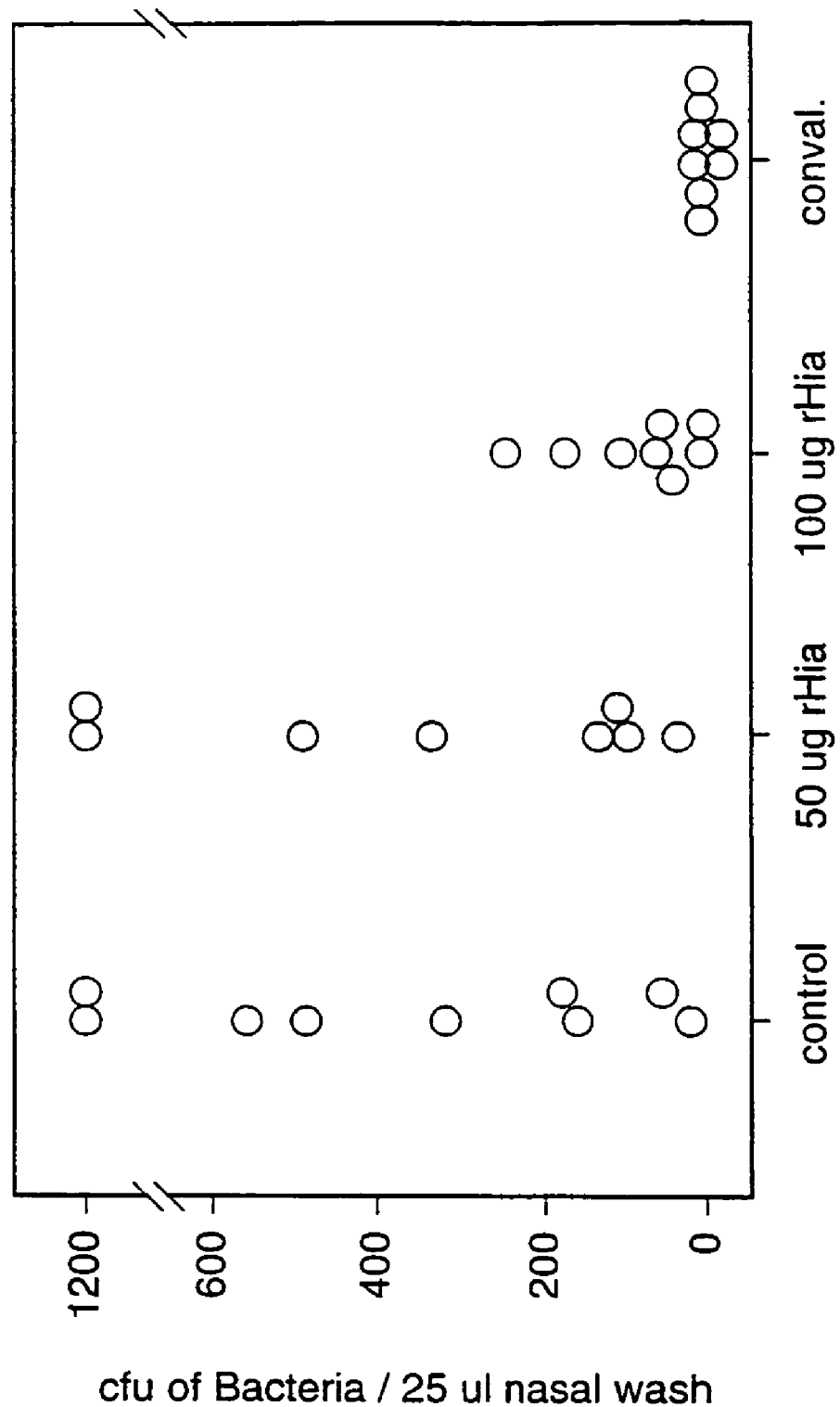

FIG. 16 illustrates the protective ability of V38 rHia (33) against nasopharyngeal colonization in a chinchilla model.

FIG. 17 shows the oligonucleotides used to PCR amplify additional hia genes. Sense (5040.SL), SEQ ID No: 21, encoded amino acids SEQ ID No: 22; Antisense (5039.SL), SEQ ID No: 3, complement SEQ ID No: 4, encoded amino acids SEQ ID No: 5.

FIG. 18 shows the nucleotide sequence (SEQ ID No: 23) and deduced amino acid sequence (SEQ ID No: 24) of the hia gene from NTHi strain 33.

FIG. 19 shows the nucleotide sequence (SEQ ID No: 25) and deduced amino acid sequence (SEQ ID No: 26) of the hia gene from NTHi strain 32.

FIG. 20 shows the nucleotide sequence (SEQ ID No: 27) and deduced amino acid sequence (SEQ ID No: 28) of the hia gene from NTHi strain 29.

FIG. 21 shows the nucleotide sequence (SEQ ID No: 29) and deduced amino acid sequence (SEQ ID No: 30 of the hia gene from NTHi strain M4071.

FIG. 22 shows the nucleotide sequence (SEQ ID No: 31) and deduced amino acid sequence (SEQ ID No: 32) of the hia gene from NTHi strain K9.

FIG. 23 shows the nucleotide sequence (SEQ ID No: 33) and deduced amino acid sequence (SEQ ID No: 34) of the hia gene from NTHi strain K22.

FIG. 24 shows the nucleotide sequence (SEQ ID No: 35) and deduced amino acid sequence (SEQ ID No: 36) of the hia gene from type c strain API.

FIG. 25 shows the nucleotide sequence (SEQ ID No: 37) and deduced amino acid sequence (SEQ ID No: 38) of the hia locus from NTHi strain 12. The overlined or underlined sequences indicate oligonucleotides used to PCR amplify across the junction of the two orfs. Sense (6431.SL) SEQ ID No: 39, (6432.SL) SEQ ID No: 40; antisense (6295.SL) SEQ ID No: 41, (6271.SL) SEQ ID No: 42.

FIG. 26 shows the nucleotide sequence (SEQ ID No.: 43) and deduced amino acid sequence (SEQ ID No.: 44) of the hia locus from NTHi strain 11, as published in U.S. Pat. No. 5,646,259.

FIG. 27 shows the alignment of the upstream ORF from the strain 12 hia locus (SEQ ID No: 45) with part of the HI1732 protein (SEQ ID No: 46) from *H. influenzae* type b strain Rd.

FIG. 28 shows the alignment of amino acid sequences from Hia (SEQ ID Nos. 24, 26, 28, 34, 30, 44, 32), Hsf (SEQ ID No.: 47) and partial sequences from *Moraxella catarrhalis* high molecular weight proteins (200 kDa) from strains 4223 and LES-1 (SEQ ID Nos.: 48, 49). Asterisks within sequences indicate stop codons, but below the sequence they indicated sequence homology. Dots indicate identical residues. The sequence alignments were prepared by direct comparison of the amino acid sequences of the respective proteins.

FIG. 29 shows the oligonucleotides used to PCR amplify the 5'end of the hia gene at the S44 truncated position. Sense (6317.SL) SEQ ID No: 55, encoding amino acids. SEQ ID No: 58; antisense (6818.SL) SEQ ID No: 57, complement SEQ ID No: 58, encoded amino acids SEQ ID No: 59.

Figure 30A:
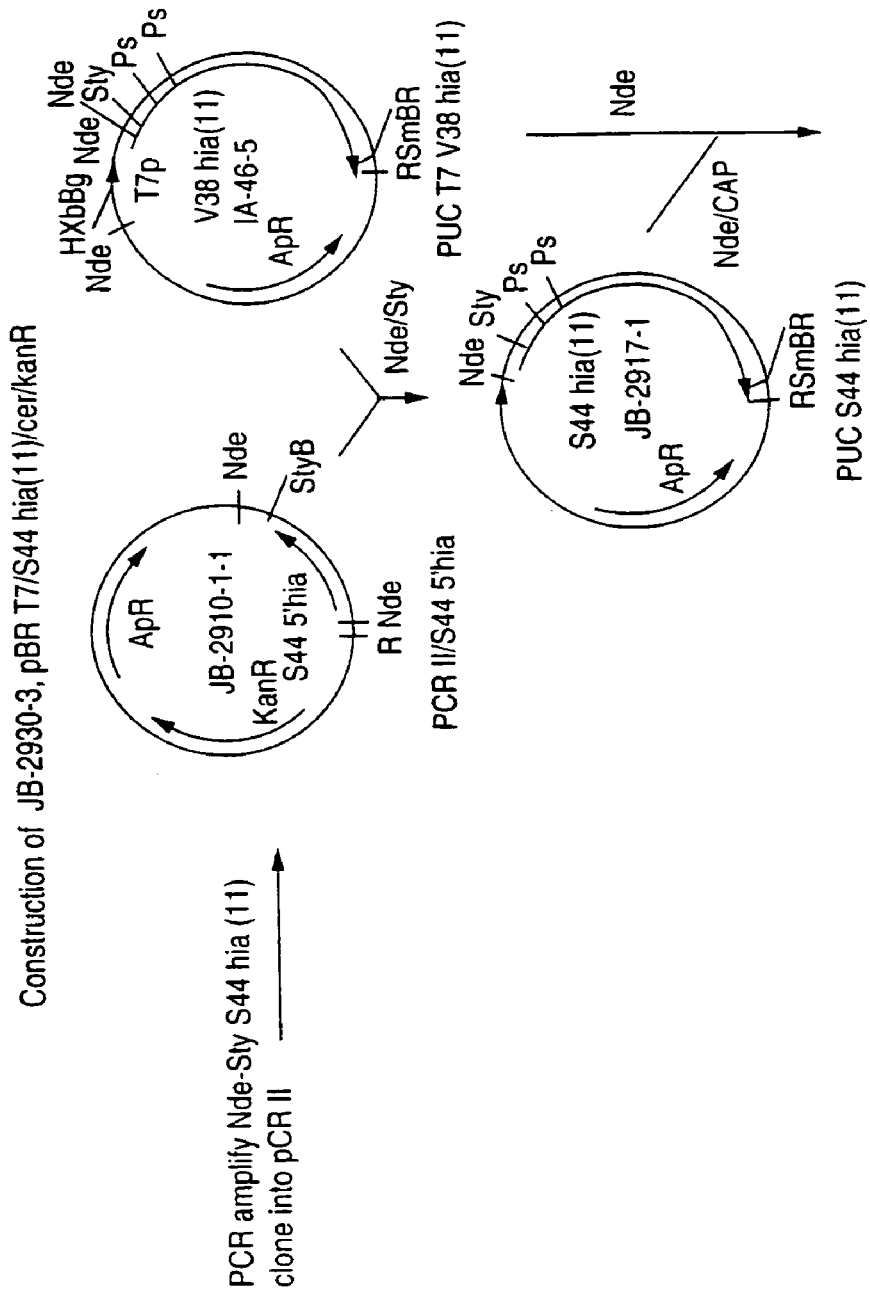
Figure 30B:
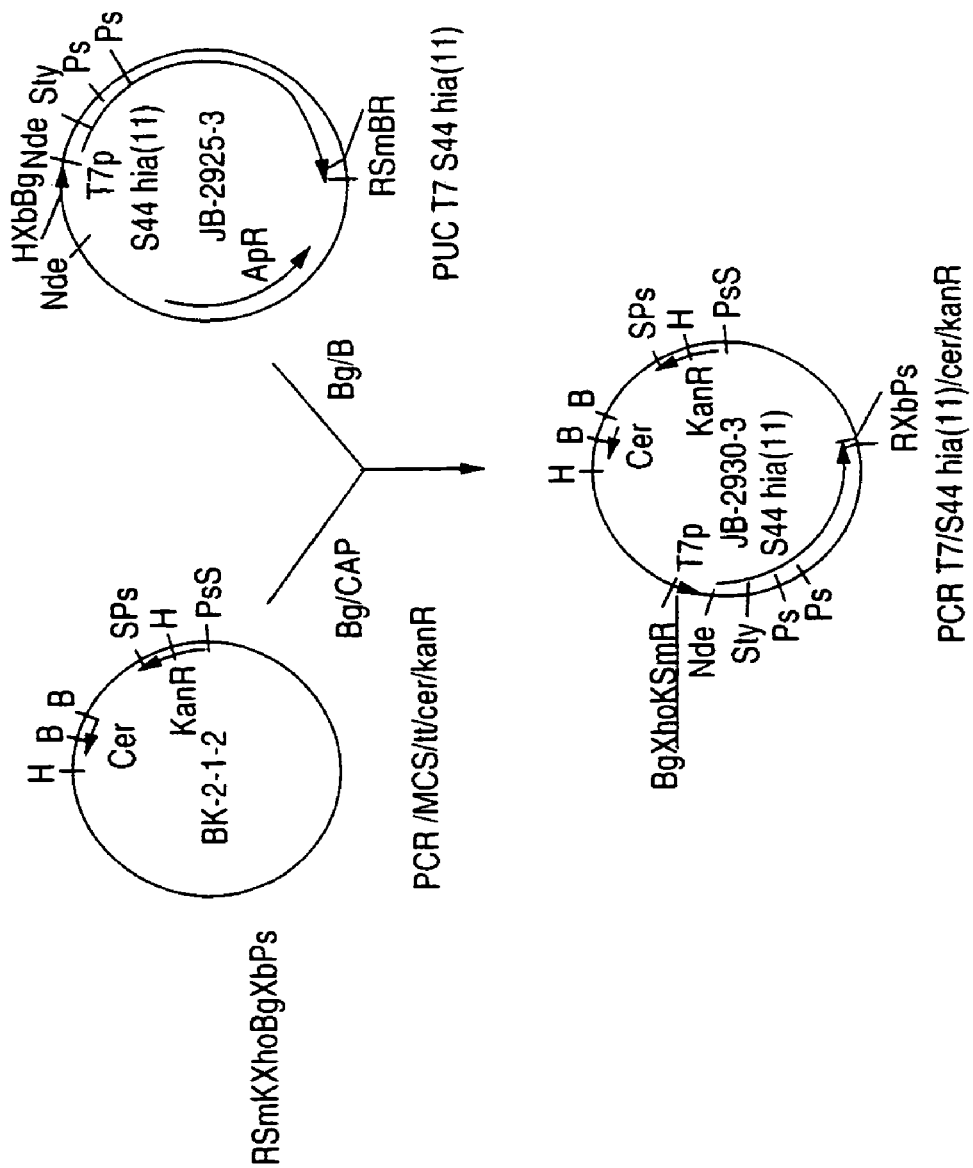

FIG. 30 shows the construction of plasmid JB-2930-3 that contains the S44 hie gene from NTHi strain and the *E. coli* car gene and the T7 promoter. Restriction enzyme sites are: B, BamH I; Bg, Bgl II; K, Kpn I, N, Nde I, P, Pst I, R, EcoR I; S, Sal I, Sm, Sma. Other abbreviations are: T7p; T7 promoter; ApR, ampicillin resistance; KanR, kanamycin resistance; CAP, calf alkaline phosphatase; tt1 transcription terminator 1 from trpA; tt2, transcription terminator 2 from T7 gene 10.

Figure 31:
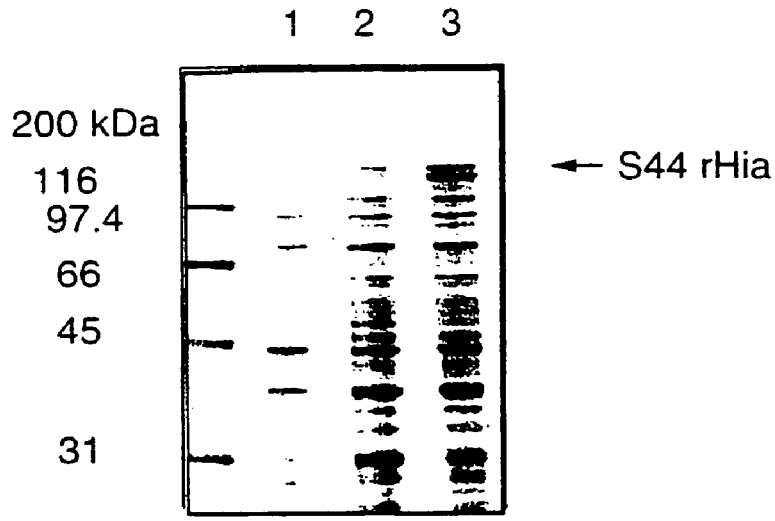

FIG. 31 shows SDS-PAGE analysis of the expression of rHia from S44. Lane 1, expression from pET 844 vector at time 0 (no induction); lane 2 expression from pET S44 vector after 4 hours induction; lane 3 expression from JB-2930-3 after 4 hours induction.

Figure 32:
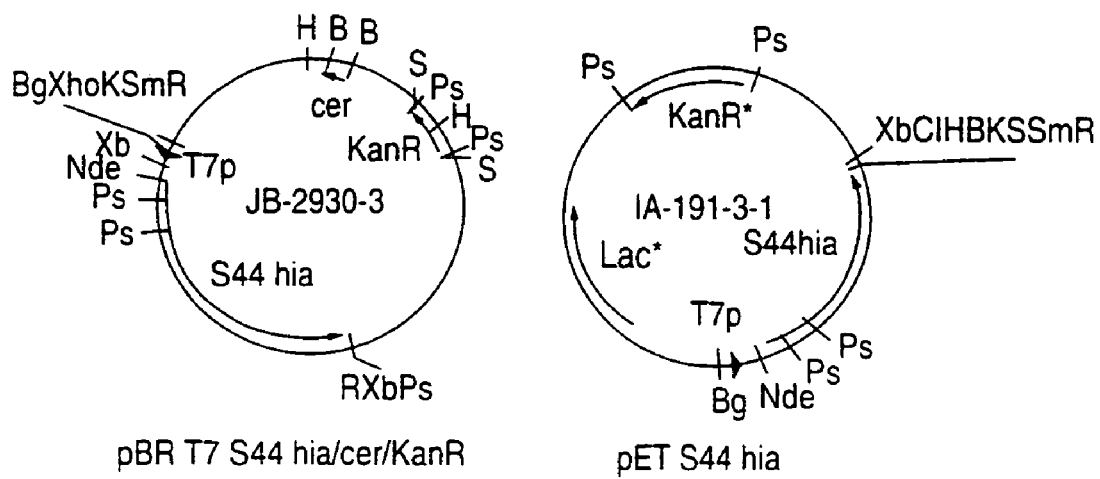

FIG. 32 shows a schematic representation of the two vectors used for the expression study, JB-2930-3 and IA-191-3-1, of S44-truncated rHia.

GENERAL DESCRIPTION OF THE INVENTION

Since *H. influenzae* strains produce low quantities of the Hia and Hsf proteins, the hia gene from NTHi strains was cloned into an expression vector for overproduction of the recombinant protein in *E. coli*. When the full-length recombinant Hia (rHia) protein was expressed, it was made in relatively low quantities. In order to confirm that there was expression of the recombinant protein, an immunoblot was performed using antibody raised to a *Moraxella catarrhalis* high molecular weight adhesin protein identified as 200 kDa in U.S. Pat. No. 5,808,024, assigned to the assignee and the disclosure of which is incorporated herein by reference. Antibody against the gel-purified native 200 kDa protein recognized a specific induced band in the rHia protein sample. The yield of rHia was not significantly improved by increasing the gene copy number of the T7 hia gene cassette.

The *E. coli* cer gene has been shown to stabilize plasmids containing large inserts (ref. 15), but the yield of rHia was not significantly improved by adding the *E. coli* cer gene to the expression vector. However, the *E. coli* cells were observed to clump during culture, suggesting that there was surface expression of the Hia adhesin protein. The apparent toxicity of the rHia protein might be overcome if it were made as inclusion bodies, so truncations were made at the 5'-end of the gene to delete putative signal sequences. This modification resulted in good production and recovery of truncated rHia starting from the V38 position.

The full-length and V38-truncated rHia proteins were immunogenic and the resultant anti-rHia antibodies were protective in passive infant rat models of bacteremia due to *H. influenzae* type a or type b strains. In addition, the truncated V38 rHia protein was found to be partially protective against nasopharyngeal colonization in an active challenge model in chinchillas. The protection afforded by rHia derived from an NTHi strain against disease caused by NTHi and encapsulated type a or type b strains, indicates that there may be common protective epitopes. The cloning and sequence analysis of additional hia genes may help to identify conserved regions. The full-length or N-terminal truncated rHia proteins may be used as vaccine components to protect against *Haemophilus influenzae* disease.

Any *Haemophilus* strains that have hia genes may be conveniently used to provide the purified and isolated nucleic acid molecules (which may be in the form of DNA molecules), comprising at least a portion coding for a Hia protein as typified by embodiments of the present invention. Such strains are generally available from clinical sources and from bacterial culture collections, such as American Type Culture Collection. Appropriate strains of *Haemophilus* include:

Non-typeable *Haemophilus* strain 11;
Non-typeable *Haemophilus* strain 33;
Non-typeable *Haemophilus* strain 32;
Non-typeable *Haemophilus* strain 29;
Non-typeable *Haemophilus* strain M4071;
Non-typeable *Haemophilus* strain K9;
Non-typeable *Haemophilus* strain K22;
Non-typeable *Haemophilus* strain 12;
Type C *Haemophilus* strain API.

In this application, the term "Hia" protein is used to define a family of Hia proteins that includes those having naturally occurring variations in their amino acid sequences as found in various strains of *Haemophilus*.

Figure 1A:
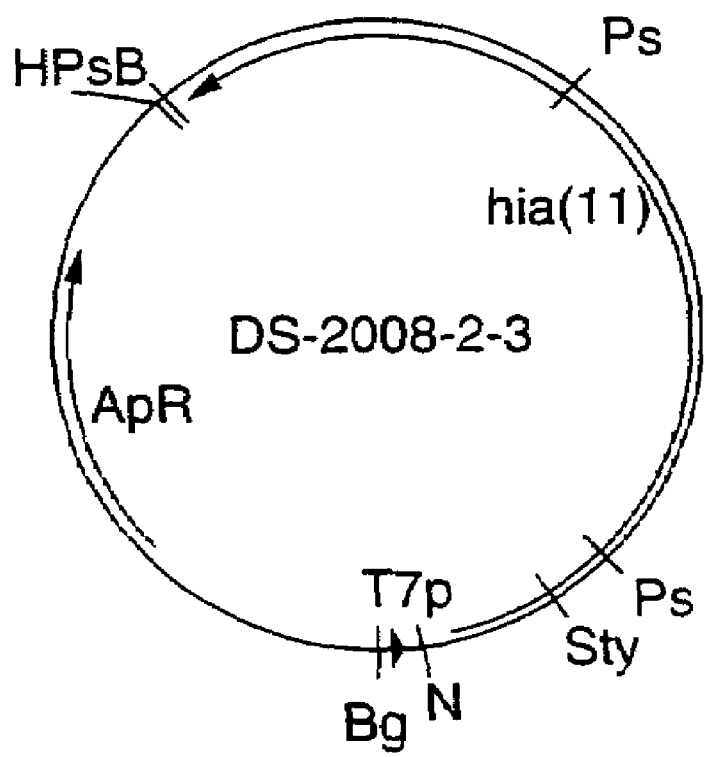
FIG. 1A shows a restriction map for plasmid DS-2008-2-3 that contains the T7 promoter and the full-length NTHi strain 11 hia gene.
Figure 1B:
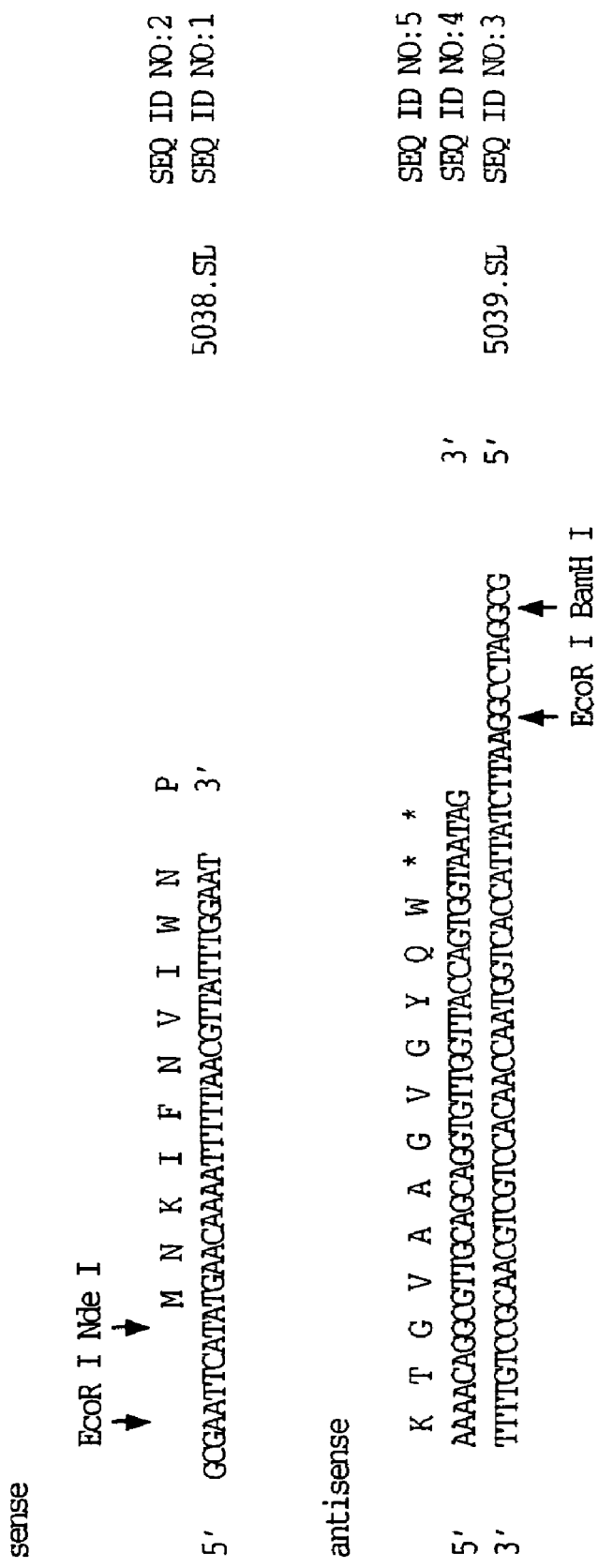
FIG. 1B shows the oligonucleotides used to PCR amplify the strain 11 hia gene. Sense Strand (5038.SL): SEQ ID No: 1, encoded amino acids SEQ ID No: 2; Antisense Strand (5039.SL): SEQ ID No: 3, complement SEQ ID No: 4, encoded amino acids SEQ ID No: 5. Restriction enzyme sites are: B, BamH I; Bg, Bgl II; H, Hind III; N, Nde I; Ps, Pst I; Sty, Sty I. Other abbreviations are: T7p, T7 promoter; ApR, ampicillin resistance.

Referring to FIG. 1A, there is illustrated a restriction map of plasmid DS-2008-2-3 that contains a full-length hia gene from non-typeable. *Haemophilus influenzae* strain 11, under the influence of the T7 promoter. The nucleic acid (SEQ ID No.: 43) and deduced amino acid sequence (SEQ ID No.: 44) of the hia gene from strain 11, are described in the aforementioned U.S. Pat. No. 5,646,259 (and identified therein as "HAI"). The oligonucleotides used to PCR amplify the hia gene from the ATG start codon of the gene of strain 11 are shown in FIG. 1B.

Figure 2:
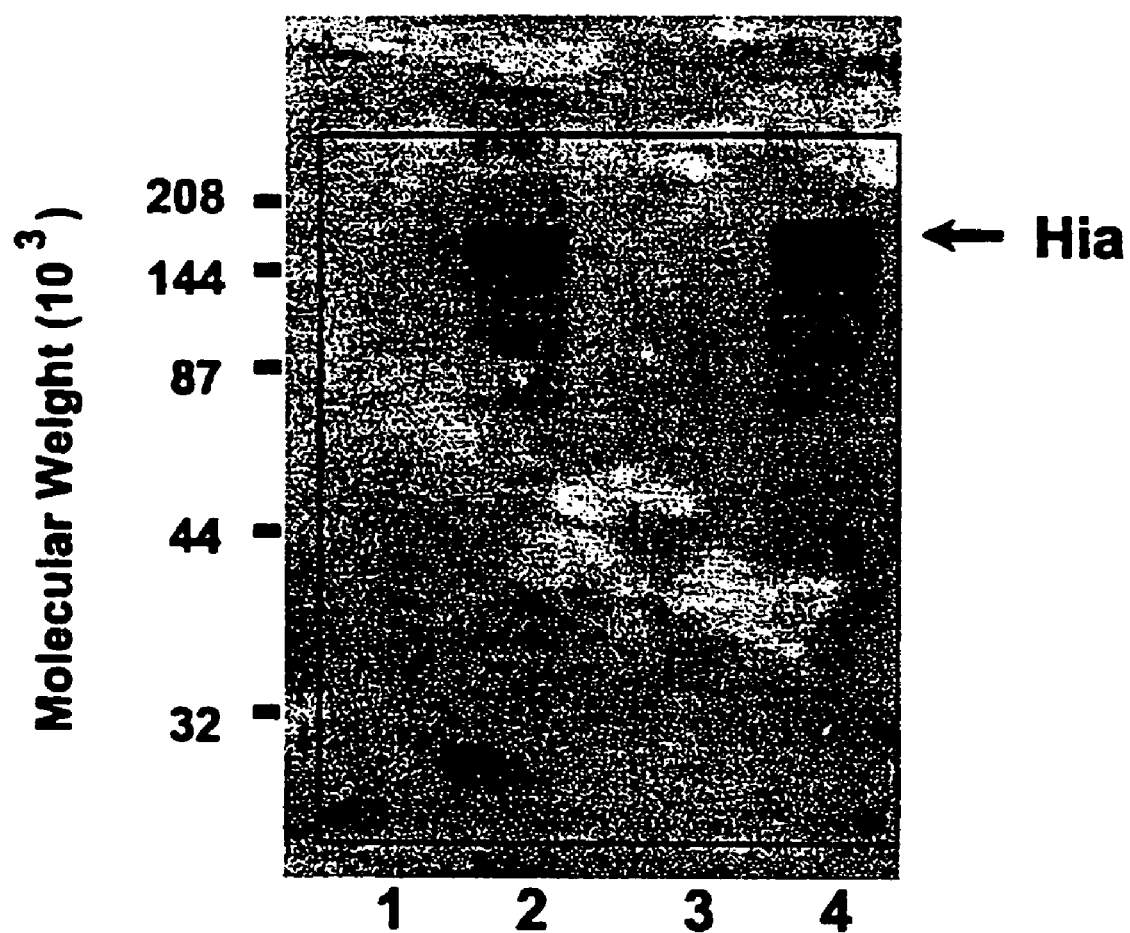
FIG. 2 shows an immunoblot of the recognition of full-length rHia protein by anti-native *Moraxella catarrhalis* high molecular weight adhesin antibody. Lane 1, DS-2043-1 uninduced; lane 2, DS-2043-1, induced for 4 h; lane 3, DS-2043-2 uninduced; lane 4, DS-2043-2, induced for 4 h; lane 5, molecular weight markers. DS-2043-1 and DS-2043-2 are independent clones of p17 hia(11) in BL21 (DE3).

Referring to FIG. 2, there is illustrated an immunoblot demonstrating the recognition of the rHia (11) protein by anti-native *Moraxella catarrhalis* high molecular weight adhesin antibody. The *M. catarrhalis* high molecular weight adhesin or 200 kDa protein described in the aforementioned U.S. Pat. No. 5,808,024 has some sequence homology with the Hia and Hsf proteins, especially at the carboxy terminus (FIG. 28).

Figure 3:
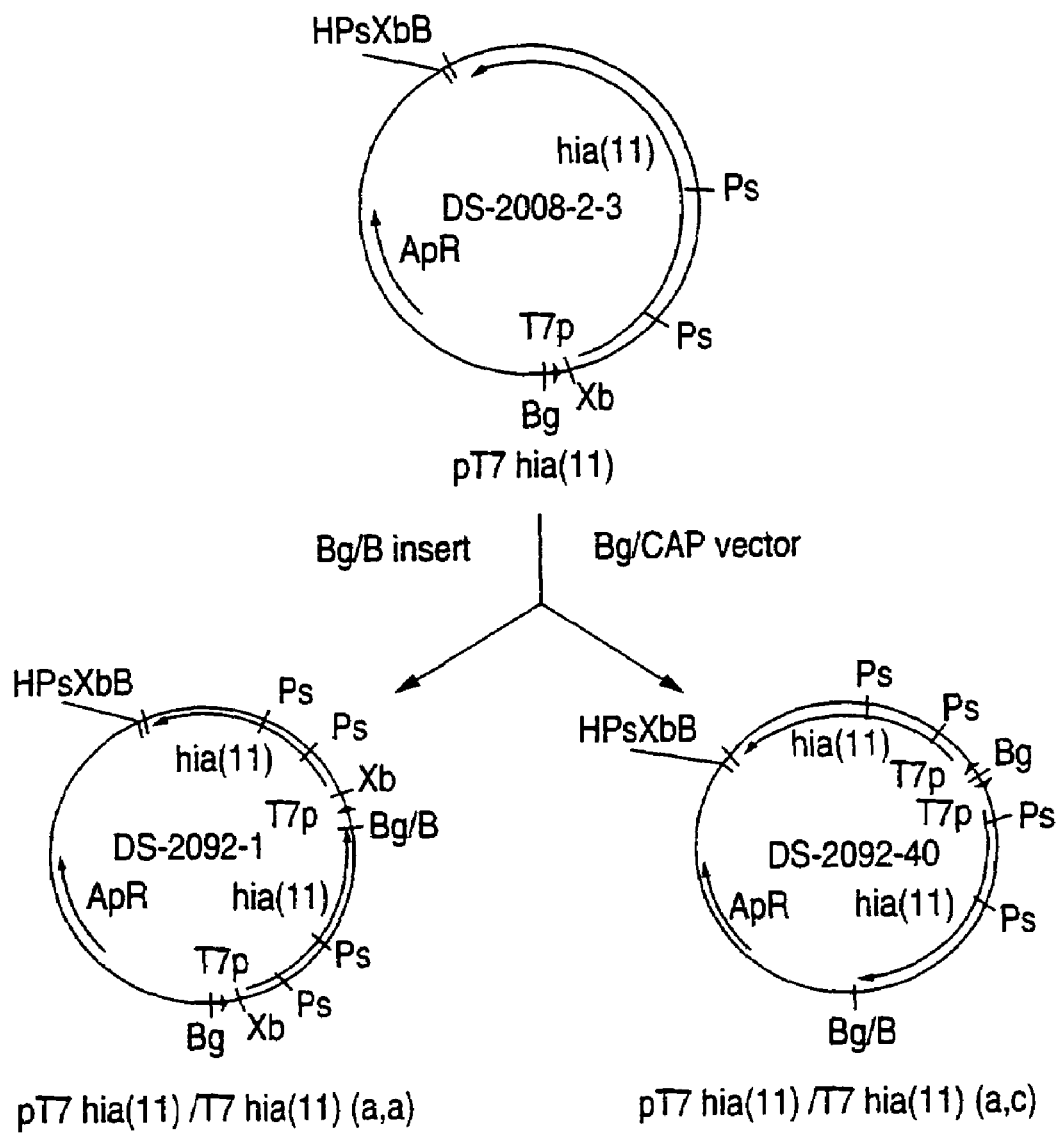
FIG. 3 shows the construction of plasmids DS-2092-1 and DS-2092-40 that contain tandem copies of the T7 hia gene cassette for the strain 11 hia gene. Restriction enzyme sites are: B, BamH I; Bg, Bgl II; H, Hind III; Ps, Pst I; Xb, Xba I. Other abbreviations are: CAP, calf alkaline phosphatase; T7p, T7 promoter; ApR, ampicillin resistance.

Referring to FIG. 3, there is illustrated a construction scheme for plasmids DS-2092-1 and DS-2092-40 that contain tandem copies of T7 hia gene cassettes comprising the full-length hia gene from NTHi strain 11. Such plasmids that contain increased copy numbers of genes often have enhanced production levels for recombinant proteins. However, as seen below, the low yield of recombinant Hia was not significantly improved by increasing the gene copy number.

Referring to FIG. 4, there is illustrated the N-terminal sequence of the NTHi strain 11 protein and the position of time N-terminally truncated rHia proteins. The N-terminal truncation up to position E21 deletes a long hydrophobic region that may constitute part of a signal sequence for Hia. The deletion up to position T33 includes a long hydrophobic region and follows a potential Ala-X-Ala signal cleavage site. The deletion up to position V38 includes a long hydrophobic region and follows a potential Ala-X-Ala signal cleavage site. The recombinant Hia protein starting at position S44 includes a long hydrophobic region and follows a potential Ala-X-Ala signal cleavage site. The recombinant Hia protein starting at position N52 mimics the approximate start of the related high molecular weight (200 kDa) adhesin from *Moraxella catarrhalis* described in the aforementioned U.S. Pat. No. 5,808,024, which recombinant protein is over-produced if truncated at its N-terminus to start at V56.

Figure 5A:
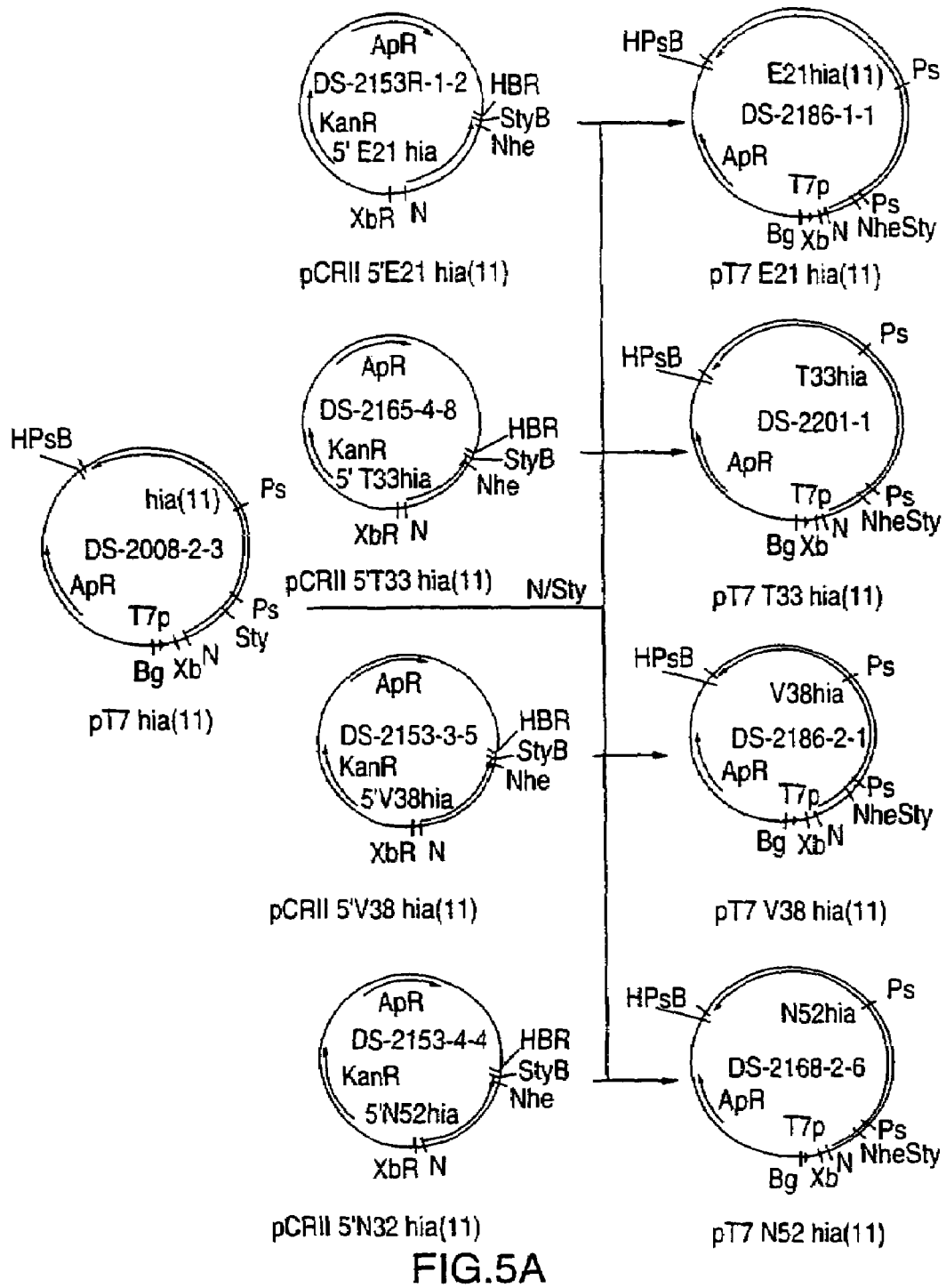
FIG. 5A shows the construction of plasmids expressing truncated hia genes from strain 11. Restriction enzyme sites are: B, BamH I; Bg, Bgl II; H, Hind III; N, Nde I; Nhe, Nhe I; Ps, Pst I; R, EcoR I; Sty, Sty I; Xb, Xba I. Other abbreviations are: T7p, T7 promoter; ApR, ampicillin resistance; KanR, kanamycin resistance.

Referring to FIG. 5A, there is illustrated the construction scheme for the generation of plasmids DS-2186-1-1, DS-2201-1, DS-2186-2-1, and DS-2168-2-6 producing four of the N-terminal truncated rHia proteins. The oligonucleotides used to PCR amplify the 5'-fragments are shown in FIG. 5B. In FIG. 30, there is illustrated the construction scheme for the generation of plasmids JB-2930-3, which produces the S44 deletion. The oligonucleotides used to PCR amplify the 5'-fragments are shown in FIG. 29.

Figure 6A:
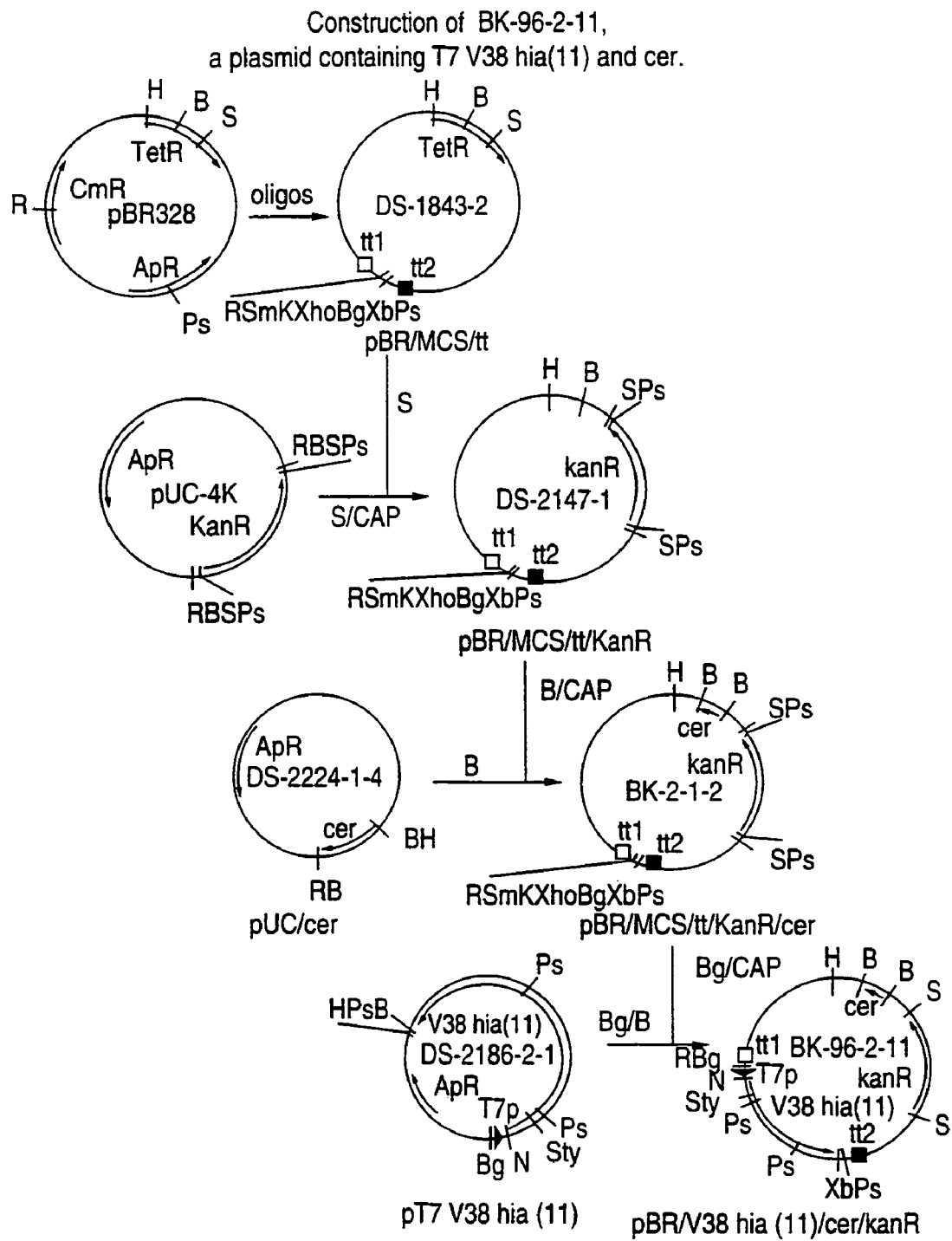
FIG. 6A shows the construction of plasmid BK-96-2-11 that contains the V38 hia gene from NTHi strain 11 and the *E. coli* cer gene. Restriction enzyme sites are: B, BamH I; Bg, Bgl II; K, Kpn I; N, Nde I; P, Pst I; R, EcoR I; S, Sal I; Sm, Sma I; Sty, Sty I; Xb, Xba I; Xho, Xho I. Other abbreviations are: T7p, T7 promoter; ApR, ampicillin resistance; KanR, kanamycin resistance; CAP, calf alkaline phosphatase; tt1 transcription terminator 1 from trpA; tt2, transcription terminator 2 from T7 gene 10.
Figure 6B:
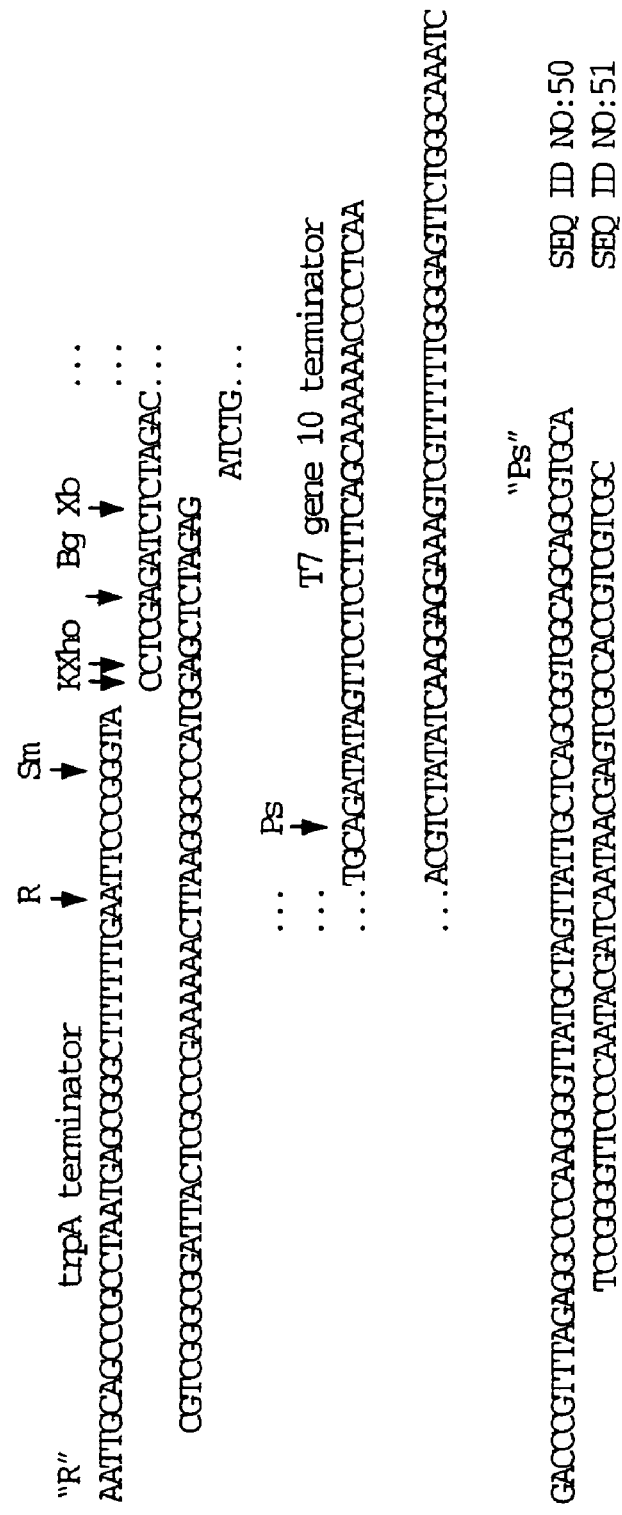
FIG. 6B shows the oligonucleotides used to construct the multiple cloning site and transcription terminators. "R" and "Ps" indicate termini that will overlap with EcoR I or Pst I ends, but will not re-generate the sites. Upperstrand (SEQ ID NO.: 50) lower strand (SEQ ID No.: 51).

Referring to FIG. 6A, there is illustrated a construction scheme for the generation of plasmid BK-96-2-11 that contains the V38 hia gene from NTHi strain 11 as well as the *E. coli* cer gene that has been shown to stabilize plasmids. The introduction of the cer gene into plasmids producing toxic proteins, was predicted to enhance protein production. There was an observed change in the morphology of the *E. coli* cells producing full-length rHia in the presence of the cer gene, in that they clumped. This suggests that there was enhanced expression of the adhesin at the surface of the cells that caused the clumping. The expression plasmid BK-96-2-11 also contains transcription terminators upstream and downstream of the T7 V38 hia gene cassette that were predicted to enhance the gene stability. The oligonucleotides used to generate the multiple cloning site and transcription terminators are shown in FIG. 6B.

Figure 7A:
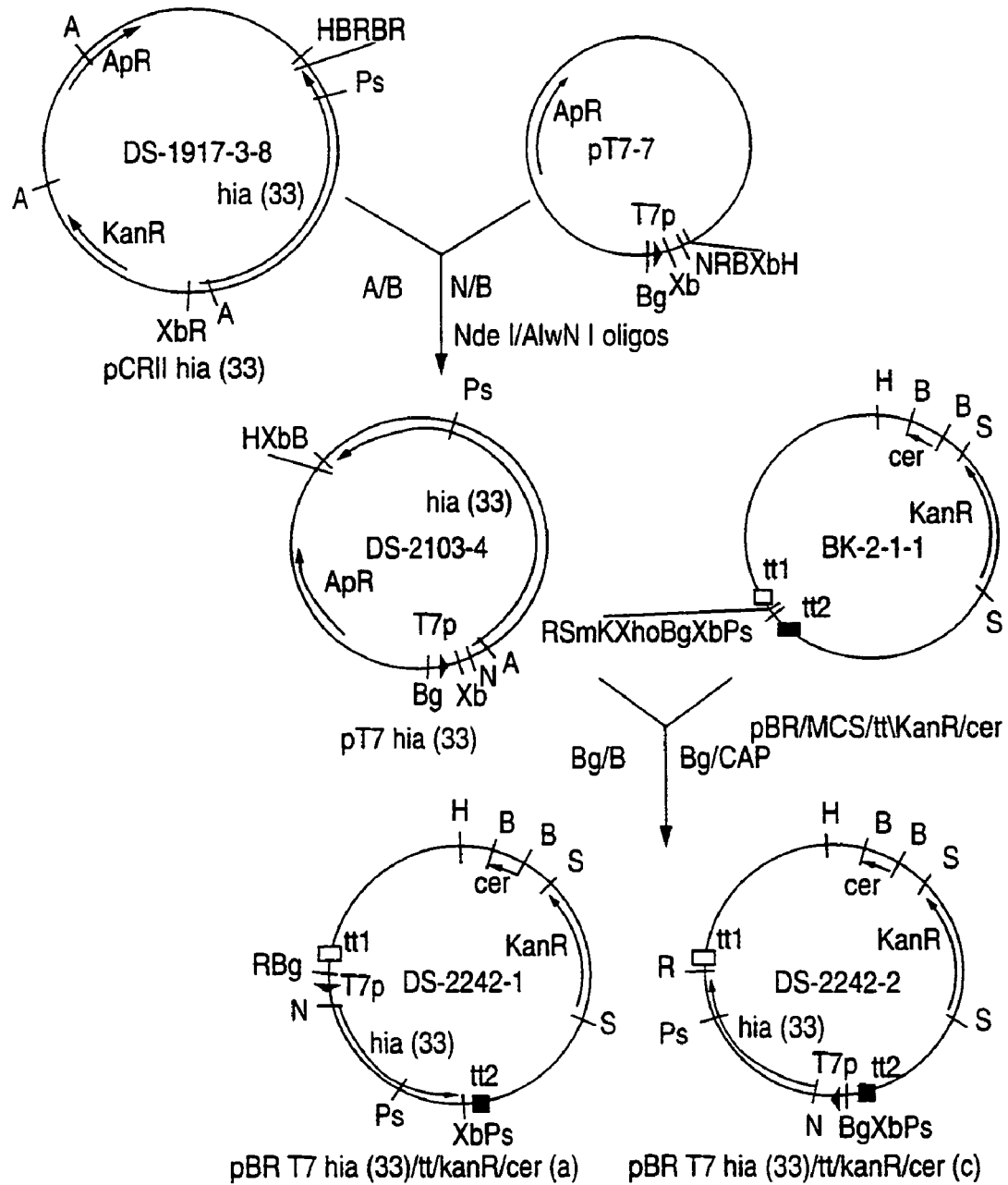
FIG. 7A shows the construction of plasmids DS-2242-1 and DS-2242-2 that contain the T7 promoter and full-length NTHi strain 33 hia gene, the *E. coli* cer gene and the kanamycin resistance gene. Restriction enzyme sites are: A, AlwN I, B, BamH I, Bg, Bgl II, H, Hind III; K, Kpn I, N, Nde I, Ps, Pst I, R, EcoR, S, Sal I, Sm, Sma I, Xb, Xba I, Xho, Xho I. Other abbreviations are: T7p, T7 promoter; ApR, ampicillin resistance; KanR, kanamycin resistance; tt1, transcription terminator 1 from trpA; tt2, transcription terminator 2 from T7 gene 10.

Referring to FIG. 7A, there is illustrated a construction scheme for plasmids DS-2242-1 and DS-2242-2 that contain a full-length hia gene from non-typeable *Haemophilus influenzae* strain 33, under the influence of the T7 promoter. The expression plasmids also contain the *E. coli* cer gene and transcription terminators upstream and downstream of the T7 hia (33) gene cassette. DS-2242-1 has the terminators coded on the same strand as the T7 hia (33) gene. However, there was no observable difference in the expression of rHia from the two plasmids. The oligonucleotides used to construct the authentic 5'-end of the NTHi strain 33 gene are shown in FIG. 7B.

Figure 8A:
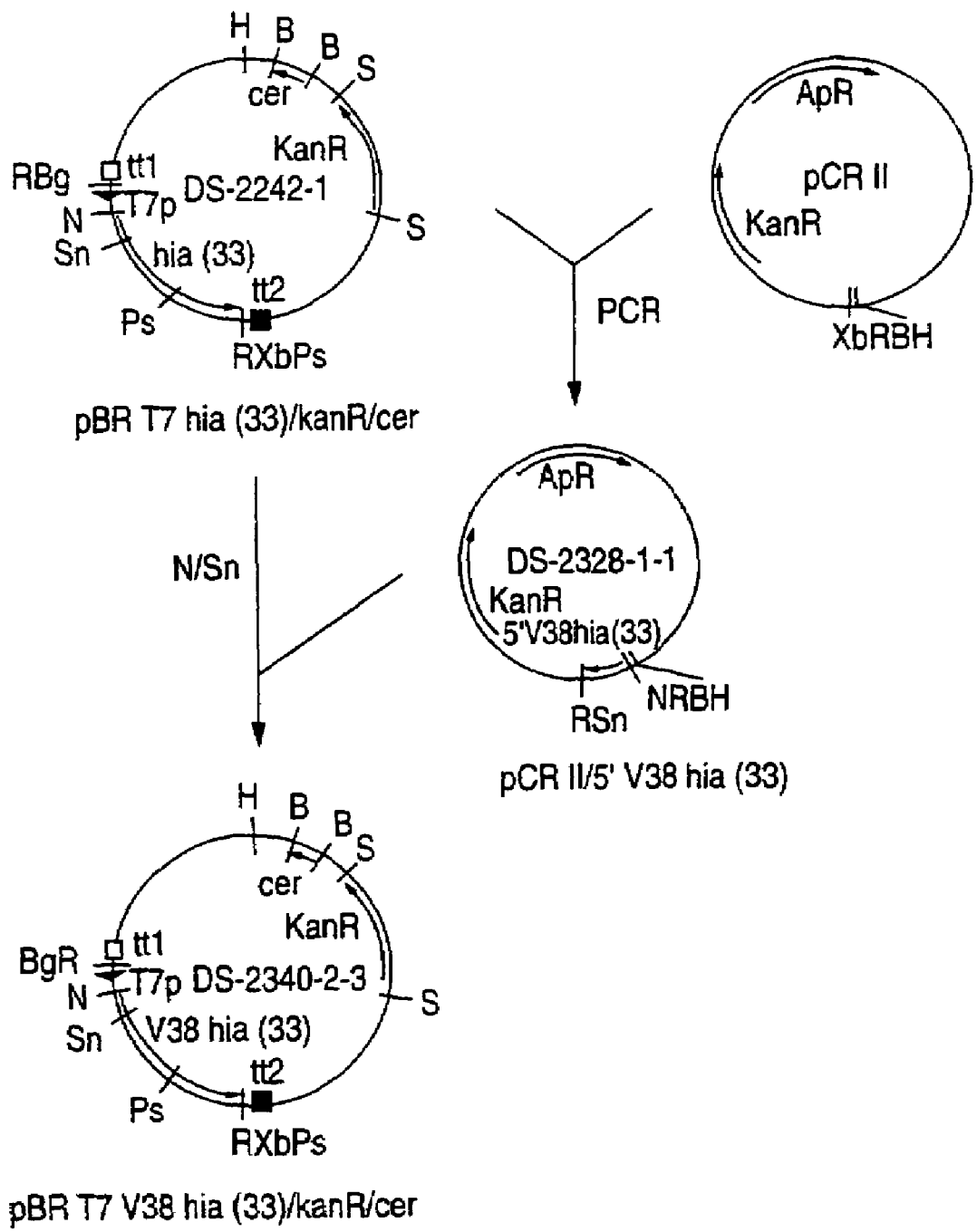
FIG. 8A shows the construction of plasmid DS-2340-2-3 that contains the T7 promoter and the V38 hia gene from strain 33, the *E. coli* cer gene and the kanamycin resistance gene. Restriction enzyme sites are: B, BamH I, Bg, Bgl II, H, Hind III; N, Nde I, Ps, Pst I, R, EcoR I), S, Sal I, Sn, SnaB I; Xb, Xba I, Other abbreviations are: T7p, T7 promoter; ApR, ampicillin resistance; KanR, kanamycin resistance; tt1, transcription terminator 1 from trpA; tt2, transcription terminator 2 from T7 gene 10.

Referring to FIG. 8A, there is illustrated a construction scheme for plasmid DS-2340-2-3 that contains the V38 hia gene from NTHi strain 33 as well as the *E. coli* cer gene. There are also transcription terminators located upstream and downstream of the T7 V38 hia gene cassette, on the same strand. The oligonucleotides used to PCR amplify the NTHi strain 33 hia gene from the V38 codon, are shown in FIG. 8B.

Referring to FIG. 9, there is shown the construction of plasmids DS-2447-2 and DS-2448-17 that contain tandem copies of the T7 V38 hia (11) or T7 V38 hia (33) gene cassettes, respectively.

Referring to FIG. 10, panel A, there is illustrated the production of rHia proteins from plasmids encoding full-length or truncated hia genes from NTHi strain 11. The production of the full-length rHia (11) protein was very low. There was also low expression observed for the E21 and T33 truncated rHia proteins. However, the V38 and N52 truncated rHia proteins have significantly improved expression levels. As shown in FIG. 10, panel B, the production of V38 rHia (11) appears to be enhanced when the *E. coli* cer gene is added to the expression plasmid.

Referring to FIG. 11, there is illustrated a purification scheme for rHia proteins, produced as inclusion bodies. Cells were lysed by sonication and the inclusion bodies purified by serial extractions. The inclusion bodies were solubilized in guanidinium chloride and impurities precipitated by the addition of polyethlyene glycol (PEG). Addition of $(NH_4)_2SO_4$ resulted in precipitation of rHia and the crude rHia was further purified by gel filtration.

Referring to FIG. 12, there is illustrated the purified V38 rHia proteins from strains 11 and 33. The inclusion bodies are shown in lane 3 and the final purified protein in lane 4. The estimated purity of the purified protein is greater than about 90% as determined by SDS-PAGE densitometry.

Referring to FIG. 13, there is shown the SDS-PAGE analysis of the stability of rHia proteins produced as described herein during 8 weeks of storage with or without glycerol at 4° C. and with glycerol at −20° C. The protein is stable under any of these conditions.

Referring to FIG. 14, there is illustrated the immunogenicity of V38 rHia proteins from strains 11 and 33 in CD-1 mice. At doses from 0.3 to 10 µg, there is a strong immune response after one or two doses with either protein. There is no obvious dose response at these levels. Similar results were observed in BALB/c mice (FIG. 15A) and in guinea pigs (FIG. 15B), indicating that rHia was very immunogenic, even at 0.3 µg per dose.

Referring to FIG. 16, there is illustrated the protection afforded by V38 rHia (33) against colonization by NTHi strain 33. As described by Yang et al (ref. 20), a chinchilla nasopharyngeal colonization model has been developed to assess protection against this earliest stage of disease. The model was initially established for NTHi strains that express hmw genes and had to be adapted for NTHi strains expressing hia genes. For the prototype hmw-expressing strain (NTHi 12), $10^2$ to $10^8$ cfu could be used to establish infection, but $5 \times 10^8$ cfu of NTHi strain 33 was required, and even at this high level no infection could be established with the prototype hia-expressing strain 11. At a 100 µg dose, it is evident that there is partial protection in the immunized cohort, although there is no protection at a 50 lag dose. Such protection against the early stages of disease illustrates the utility of the rHia adhesins as vaccine antigens.

Referring to FIG. 17, there is illustrated the oligonucleotides used to PCR amplify additional *Haemophilus influenzae* hia genes. The sequences are based upon the conserved amino and carboxy terminal sequences of the Hia and Hsf proteins.

Referring to FIG. 18, there is illustrated the complete nucleotide sequence and deduced amino acid sequence of the NTHi strain 33 hia gene. Referring to FIG. 19, there is illustrated the complete nucleotide sequence and deduced amino acid sequence of the NTHi strain 32 hia gene. Referring to FIG. 20, there is illustrated the complete nucleotide sequence and deduced amino acid sequence of the NTHi strain 29 hia gene. Referring to FIG. 21, there is illustrated the complete nucleotide sequence and deduced amino acid sequence of the NTHi strain M4071 hia gene. Referring to FIG. 22, there is illustrated the complete nucleotide sequence and deduced amino acid sequence of the NTHi strain K9 hia gene. Referring to FIG. 23, there is illustrated the complete nucleotide sequence and deduced amino acid sequence of the NTHi strain K22 hia gene. Referring to FIG. 24, there is illustrated the complete nucleotide sequence and deduced amino acid sequence of the *Haemophilus influenzae* type c strain API hia gene. Referring to FIG. 25, there is illustrated the complete nucleotide sequence and deduced amino acid sequence of the hia locus from NTHi strain 12. The PCR amplified fragment contains the 3'-end of a gene related to HI1733 gene of the *Haemophilus influenzae* type d strain Rd genome joined to the 3'-end of an hia gene. An alignment of the upstream ORF with the HI1733 protein is shown in FIG. 27.

FIG. 26 shows the complete nucleotide sequence and the deduced amino acid sequence of the Hia gene from NTHi strain 11, as published in the aforementioned U.S. Pat. No. 5,646,259.

Referring to FIG. 28, there is illustrated an alignment of the deduced protein sequences from Hsf, Hia, and partial sequences of the *M. catarrhalis* 200 kDa protein.

It is clearly apparent to one skilled in the art, that the various embodiments of the present invention have use in applications in the fields of vaccination, diagnosis, treatment of *Haemophilus* infection and the generation of immunological agents. A further non-limiting discussion of such uses is further presented below.

Vaccine Preparation and Use

Immunogenic compositions, suitable to be used as vaccines, may be prepared from immunogenic recombinant *Haemophilus influenzae* adhesin (rHia) proteins of non-typeable *Haemophilus* strains, immunogenic analogs and fragments thereof and/or immunogenic peptides as disclosed herein. The vaccine elicits an immune response which produces antibodies, including anti-rHia antibodies and antibodies that are opsonizing or bactericidal.

Immunogenic compositions, including vaccines, may be prepared as injectables, as liquid solutions or emulsions. The rHia protein, immunogenic analogs and fragments thereof and/or immunogenic peptides may be mixed with pharmaceutically acceptable excipients which are compatible with the rHia protein, immunogenic fragments analogs or immunogenic peptides. Such excipients may include, water, saline, dextrose, glycerol, ethanol and combinations thereof.

The immunogenic compositions and vaccines may further contain auxiliary substances such as wetting or emulsifying agents, pH buffering agents, or adjuvants to enhance the effectiveness of the vaccines.

Immunogenic compositions and vaccines may be administered parenterally, by injection subcutaneously or intramuscularly. Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes.

The immunogenic composition may be provided in combination with a targeting molecule for delivery to specific cells of the immune system or to mucosal surfaces. Some such targeting molecules include vitamin B12 and fragments of bacterial toxins, as described in WO 92/17167 (Biotech Australia Pty. Ltd.), and monoclonal antibodies, as described in U.S. Pat. No. 5,194,254 (Barber et al).

Alternatively, other modes of administration including suppositories and oral formulations may be desirable. For suppositories, binders and carriers may include, for example polyalkalene glycols or triglycerides. Oral formulations may include normally employed incipients such as, for example pharmaceutical grades of saccharine, cellulose and magnesium carbonate. These compositions take the form of solutions, suspensions, tablets, pills, capsules, sustained release formulations or powders and contain about 1 to 95% of the rHia protein, fragment analogs and/or peptides.

The vaccines are administered in a manner compatible with the dosage formulation, and in such amount as will be therapeutically effective, protective and immunogenic. The quantity to be administered depends on the subject to be treated, including, for example, the capacity of the individual's immune system to synthesize antibodies, and if needed, to produce a cell-mediated immune response. Precise amounts of active ingredient required to be administered depend on the judgment of the practitioner. However, suitable dosage ranges are readily determinable by one skilled in the art and may be of the order of micrograms of the rHia, analogs and fragments thereof and/or peptides. Suitable regimes for initial administration and booster doses are also variable, but may include an initial administration followed by subsequent administrations. The dosage of the vaccine may also depend on the route of administration and will vary according to the size of the host.

The nucleic acid molecules encoding the rHia proteins of non-typeable *Haemophilus* may also be used directly for immunization by administration of the DNA directly, for example by injection for genetic immunization or by constructing a live vector, such as *Salmonella*, BCG, adenovirus, poxvirus, vaccinia or poliovirus, containing the nucleic acid molecule. A discussion of some live vectors that have been used to carry heterologous antigens to the immune system is contained in, for example, O'Hagan (1992) (ref. 16). Processes for the direct injection of DNA into test subjects for genetic immunization are described in, for example, Ulmer et al., 1993 (ref. 17).

Immunogenicity can be significantly improved if the antigens are co-administered with adjuvants, commonly used as an 0.05 to 1.0 percent solution in phosphate—buffered saline. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. Intrinsic adjuvants, such as lipopolysaccharides, normally are the components of the killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established.

A wide range of extrinsic adjuvants can provoke potent immune responses to antigens. These include the specific adjuvants detailed above as well as saponins complexed to membrane protein antigens (immune stimulating complexes), pluronic polymers with mineral oil, killed mycobacteria and mineral oil, Freund's complete adjuvants, bacterial products, such as muramyl dipeptide (MDP) and lipopolysaccharide (LPS), as well as lipid A, and liposomes.

To efficiently induce humoral immune responses (HIR) and cell-mediated immunity (CMI), immunogens are emulsified in adjuvants. Many adjuvants are toxic, inducing granulomas, acute and chronic inflammations (Freund's complete adjuvant, FCA), cytolysis (saponins and pluronic polymers) and pyrogenicity, arthritis and anterior uveitis (LPS and MDP). Although FCA is an excellent adjuvant and widely used in research, it is not licensed for use in human or veterinary vaccines because of its toxicity.

Desirable characteristics of ideal adjuvants include:

(1) lack of toxicity;

(2) ability to stimulate a long-lasting immune response;

(3) simplicity of manufacture and stability in long-term storage;

(4) ability to elicit both CMI and HIR to antigens administered by various routes, if required;

(5) synergy with other adjuvants;

(6) capability of selectively interacting with populations of antigen presenting cells (APC);

(7) ability to specifically elicit appropriate $T_H1$ or $T_H2$ cell-specific immune responses; and (8) ability to selectively increase appropriate antibody isotype levels (for example, IgA) against antigens.

U.S. Pat. No. 4,855,283 granted to Lockhoff et al on Aug. 8, 1989 which is incorporated herein by reference thereto teaches glycolipid analogues including N-glycosylamides, N-glycosylureas and N-glycosylcarbamates, each of which is substituted in the sugar residue by an amino acid, as immunomodulators or adjuvants. Thus, Lockhoff et al. 1991 (ref. 18) reported that N-glycolipid analogs displaying structural similarities to the naturally-occurring glycolipids, such as glycosphingolipids and glycoglycerolipids, are capable of eliciting strong immune responses in both herpes simplex virus vaccine and pseudorabies virus vaccine. Some glycolipids have been synthesized from long chain-alkylamines and fatty acids that are linked directly with the sugars through the anomeric carbon atom, to mimic the functions of the naturally occurring lipid residues.

U.S. Pat. No. 4,258,029 granted to Moloney, assigned to the assignee hereof and incorporated herein by reference thereto, teaches that octadecyl tyrosine hydrochloride (OTH) functions as an adjuvant when complexed with tetanus toxoid and formalin inactivated type I, II and III poliomyelitis virus vaccine. Also, Nixon-George et al. 1990 (ref. 19), reported that octadecyl esters of aromatic amino acids complexed with a recombinant hepatitis B surface antigen, enhanced the host immune responses against hepatitis B virus.

Immunoassays

The rHia protein of a non-typeable strain of *Haemophilus*, analogs and fragments thereof produced according to the present invention are useful as immunogens, as antigens in immunoassays including enzyme-linked immunosorbent assay (ELISA), RIAs and other non-enzyme linked antibody binding assays or procedures known in the art for the detection of anti-bacterial, *Haemophilus*, and/or Hia antibodies. In ELISA assays, the Hia protein, analogs and fragments are immobilized onto a selected surface, for example a surface capable of binding proteins or peptides, such as the wells of a polystyrene microtiter plate. After washing to remove incompletely adsorbed Hia protein, analogs and/or fragments, a nonspecific protein such as a solution of bovine serum albumin (BSA) or casein that is known to be antigenically neutral with regard to the test sample may be bound to the selected surface. This allows for blocking of nonspecific adsorption sites on the immobilizing surface and thus reduces the background caused by nonspecific bindings of antisera onto the surface.

The immobilizing surface is then contacted with a sample, such as clinical or biological materials, to be tested in a manner conducive to immune complex (antigen/antibody) formation. This may include diluting the sample with diluents, such as BSA, bovine gamma globulin (BGG) and/or phosphate buffered saline (PBS)/Tween. The sample is then allowed to incubate for from about 2 to about 4 hours, at temperature such as of the order of about 25° to about 37° C. Following incubation, the sample-contacted surface is washed to remove non-immunocomplexed material. The washing procedure may include washing with a solution such as PBS/Tween, or a borate buffer.

Following formation of specific immunocomplexes between the test sample and the bound Hia protein, analogs and/or fragments, and subsequent washing, the occurrence, and even amount, of immunocomplex formation may be determined by subjecting the immunocomplex to a second antibody having specificity for the first antibody. If the test sample is of human origin, the second antibody is an antibody having specificity for human immunoglobulins and in general IgG. To provide detecting means, the second antibody may have an associated activity, such as an enzymatic activity, that will generate, for example, a color development, upon incubating with an appropriate chromogenic substrate. Quantification may then achieved by measuring the degree of color generation using, for example, a visible spectra spectrophotometer.

Use of Sequences as Hybridization Probes

The nucleotide sequences of the present invention, comprising the newly-isolated and characterized sequences of the hia genes, allow for the identification and cloning of the hia genes from other non-typeable strains of *Haemophilus*.

The nucleotide sequences comprising the sequence of hia genes of the present invention are useful for their ability to selectively form duplex molecules with complementary stretches of other hia genes. Depending on the application, a variety of hybridization conditions may be employed to achieve varying degrees of selectivity of the probe toward the other hia genes in other strains of non-typeable *Haemophilus*. For a high degree of selectivity, relatively stringent conditions are used to form the duplexes, such as low salt and/or high temperature conditions, such as provided by 0.02 M to 0.15 M NaCl at temperatures of between about 50° C. to 70° C. For some applications, less stringent hybridization conditions are required such as 0.15 M to 0.9 M salt, at temperatures ranging from between 20° C. to 55° C. Hybridization conditions can also be rendered more stringent by the addition of increasing amount of formamide, to destabilize the hybrid duplex. Thus, particular hybridization conditions can be readily manipulated, and will generally be a method of choice depending on the desired results. In general, convenient hybridization temperatures in the presence of 50% formamide and 0.15 M NaCl are: 42° C. for an hia gene which is about 95 to 100% homologous to the target nucleic acid fragment, 37° C. for about 90 to 95 homology and 32° C. for about 85 to 90% homology.

In a clinical diagnostic embodiment, the nucleic acid sequences of the hia genes of the present invention may be used in combination with an appropriate means, such as a label, for determining hybridization. A wide variety of appropriate indicator means are known in the art, including radioactive, enzymatic or other ligands, such as avidin/biotin, which are capable of providing a detectable signal. In some diagnostic embodiments, an enzyme tag, such as urease, alkaline phosphatase or peroxidase, instead of a radioactive tag may be used. In the case of enzyme tags, colorimetric indicator substrates are known which can be employed to provide a means visible to the human eye or spectrophotometrically, to identify specific hybridization with samples containing Hia genes sequences.

The nucleic acid sequences of Hia genes of the present invention are useful as hybridization probes in solution hybridizations and in embodiments employing solid-phase procedures. In embodiments involving solid-phase procedures the test DNA (or RNA) from samples, such as clinical samples, including exudates, body fluids (e.g., serum, amniotic fluid, middle ear effusion, sputum, bronchoalveolar lavage fluid) or even tissues, is adsorbed or otherwise affixed to a selected matrix or surface. The fixed, single-stranded nucleic acid is then subjected to specific hybridization with selected probes comprising the nucleic acid sequences of the hia genes or fragments thereof of the present invention under desired conditions. The selected conditions will depend on the particular circumstances based on the particular criteria required depending on, for example, the G+C contents, type of target nucleic acid, source of nucleic acid, size of hybridization probe etc. Following washing of the hybridization surface so as to remove non-specifically bound probe molecules, specific hybridization is detected, or even quantified, by means of the label. It is preferred to select nucleic acid sequence portions which are conserved among species of *Haemophilus*. The selected probe may be at least 18 by in length and may be in the range of 30 by to 90 by long.

Expression of the *Haemophilus influenzae* Adhesin Genes

Plasmid vectors containing replicon and control sequences which are derived from species compatible with the host cell may be used for the expression of the hia genes in expression systems. The vector ordinarily carries a replication site, as well as marking sequences which are capable of providing phenotypic selection in transformed cells. For example, *E. coli* may be transformed using pBR322 which contains genes for ampicillin and tetracycline resistance and thus provides easy means for identifying transformed cells. The pBR322 plasmid, or other microbial plasmid or phage, must also contain, or be modified to contain, promoters which can be used by the host cell for expression of its own proteins.

In addition, phage vectors containing replicon and control sequences that are compatible with the host can be used as a transforming vector in connection with these hosts. For example, the phage in lambda GEM™-11 may be utilized in making recombinant phage vectors which can be used to transform host cells, such as *E. coli* LE392.

Promoters commonly used in recombinant DNA construction include the β-lactamase (penicillinase) and lactose promoter systems and other microbial promoters, such as the T7 promoter system employed herein in preferred embodiments (U.S. Pat. No. 4,952,496). Details concerning the nucleotide sequences of promoters are known, enabling a skilled worker to ligate them functionally with genes. The particular promoter used will generally be a matter of choice depending upon the desired results. Hosts that are appropriate for expression of the Hia protein and immunological fragments or analogs thereof include *E. coli, Bordetella* species, *Bacillus* species, *Haemophilus*, fungi, yeast or the baculovirus expression system may be used. *E. coli* is the preferred host used herein.

In accordance with this invention, it is preferred to produce the Hia proteins by recombinant methods, particularly when the naturally occurring Hia protein as purified from a culture of a species of *Haemophilus* may include trace amounts of toxic materials or other contaminants. This problem can be avoided by using recombinantly produced Hia protein in heterologous systems which can be isolated from the host in a manner to minimize contaminants in the purified materials, specifically employing the constructs described herein.

Biological Deposits

A vector that contains nucleic acid coding for a high molecular weight protein of a non-typeable strain of *Haemophilus* that is described and referred to herein has been deposited with the America Type Culture Collection (ATCC) located at 10801 University Boulevard, Manassas, Va. 20110-2209, USA, pursuant the Budapest Treaty and prior to the filing of this application. Samples of the deposited vector will become available to the public and all restrictions imposed or access to the deposits will be received upon grant of a patent based on this U.S. patent application. In addition, the deposit will be replaced if viable samples cannot be dispensed by the Depository. The invention described and claimed herein is not limited in scope by the biological materials deposited, since the deposited embodiment is intended only as an illustration of the invention. Any equivalent or similar vectors that contain nucleic acid which encodes equivalent or similar antigens as described in this application are within the scope of the invention.

| Deposit Summary | | |
|---|---|---|
| Plasmid | ATCC | Deposit Date |
| BK-96-2-11 | 203771 | Feb. 11, 1999 |

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Methods of molecular genetics, protein biochemistry, immunology and fermentation technology used, but not explicitly described in this disclosure and these Examples, are amply reported in the scientific literature and are well within the ability of those skilled in the art.

Example 1

This Example describes the construction of plasmid DS-2008-2-3 that expresses full-length rHia proteins from NTHi strain 11.

Chromosomal DNA was purified from NTHi strain 11 and the full-length hia gene was PCR amplified using the oligonucleotides (5038.SL and 5039.SL) described in FIG. 1B. An Nde I site was engineered at the 5'-end of the gene and a BamH I site was engineered at the 3'-end for cloning into the pT7-7 expression vector (ref. 21). The amplified fragment was digested with Nde I/BamH I and cloned into pT7-7 that had been digested with the same enzymes. Plasmid DS-2008-2-3 contains a 3.4 kb strain 11 hia gene downstream of the T7 promoter (FIG. 1A). The plasmid was used to express recombinant Hia (Example 9 below).

Example 2

This Example illustrates the recognition of rHia by anti-native *Moraxella catarrhalis* high molecular weight adhesin antibody.

There is some sequence conservation observed between the *Haemophilus influenzae* Hia proteins and a *Moraxella catarrhalis* high molecular weight adhesin identified as the *M. catarrhalis* 200 kDa protein in aforementioned U.S. Pat. No. 5,808,024 (FIG. 28). The native *M. catarrhalis* 200 kDa protein was gel purified as described in U.S. Pat. No. 5,808,024 and guinea pig anti-native 200 kDa antibody was generated. The T7 hia gene was expressed from plasmid DS-2008-2-3 and the cell culture containing the rHia protein was electroblotted to nitrocellulose membrane. Immunoblot analysis using anti-native 200 kDa antibody showed that the antibody recognized the rHia protein, as seen in FIG. 2.

Example 3

This Example describes the construction of plasmids DS-2092-1 and DS-2092-40 that contain tandem copies of T7 hia (11) gene cassettes.

In order to improve the production of full-length recombinant Hia protein, tandem copies of the T7 hia gene cassette containing the strain 11 hia gene (Example 1) were inserted into a single vector. Plasmid DS-2008-2-3 was linearized with Bgl II and dephosphorylated. Plasmid DS-2008-2-3 was also digested with Bgl II and BamH I to excise the T7 hia gene cassette. The T7 hia fragment was ligated into the linearized vector to generate plasmid DS-2092-1 that contains two copies of the T7 hia gene in the anti-clockwise orientation (a,a) and plasmid DS-2092-40 that contains tandem copies in opposite orientations (a,c) (FIG. 3). There was no obvious improvement in expression of rHia from either construct (see Example 9 below).

Example 4

This Example describes the construction of plasmids expressing truncated strain 11 hia genes.

The production of the rHia protein from single or tandem copies of the T7 hia gene cassette was very low and the protein seemed to be toxic to *E. coli* (as described below in Example 9). Since *H. influenzae* Hia is a surface-exposed adhesin molecule, it must either utilize a signal sequence or accessory protein(s) for secretion, but there are no known accessory genes involved. If the signal sequence were removed for expression of the recombinant protein in *E. coli*, the rHia might be expressed as inclusion bodies and the toxic effect reduced. A putative signal sequence and cleavage sites were identified and four constructs expressing N-terminally truncated rHia proteins were designed (FIG. 4). There is a unique Sty I site in the strain 11 hia gene about 500 by from the start codon. Plasmid DS-2008-2-3 was digested with Nde I and Sty I and the 5.7 kb vector fragment purified (FIG. 5A). PCR primers were designed to amplify from the truncation site to the Sty I site and a unique Nhe I site was introduced into the antisense primer for screening truncated clones (FIG. 5B). The amplified fragments were subcloned into pCR11 for easier manipulation, generating plasmids DS-2153R-1-2 (E21), DS-2165-4-8 (T33), DS-2153-3-5 (V38), and DS-2153-4-4 (N52). The pCRII hia plasmids were digested with Nde I and Sty I and the fragments ligated with the vector piece from DS-2008-2-3. Plasmids DS-2186-1-1 (E21), DS-2201-1 (T33), DS-2186-2-1 (V38), and DS-2168-2-6 (N52) were generated that contained the T7 promoter and truncated hia genes as indicated in parentheses. These plasmids were used to express recombinant Hia (see Example 9 below).

Example 5

This Example describes the construction of plasmid BK-96-2-11 that contains the T7 V38 hia (11) cassette, the *E. coli* cer gene, and the kanamycin resistance gene.

Plasmid DS-1843-2 is a pBR328-based plasmid in which a multiple cloning site and two transcription terminators have been introduced on oligonucleotides, between the EcoR I and Pst I sites, thus destroying both the chloramphenicol and ampicillin resistance genes (FIG. 6B). The kanamycin resistance gene from pUC-4K was inserted at the Sal I site, to generate plasmid DS-2147-1 that is kanamycin resistant and tetracycline sensitive. Plasmid DS-2224-1-4 is a pUC plasmid containing a synthetic *E. coli* cer gene (ref. 15) constructed from oligonucleotides and flanked by BamH I sites. The 290 by BamH I fragment of the cer gene was inserted into the BamH I site of DS-2147-1 creating plasmid BK-2-1-2. This pBR-based plasmid thus contains a multiple cloning site, the kanamycin resistance gene and the cer gene. Plasmid BK-2-1-2 was linearized with Bgl II and dephosphorylated. Plasmid DS-2186-2-1 was digested with Bgl II and BamH I and the 3.6 kb T7 V38 hia fragment was inserted into BK-2-1-2, creating plasmid BK-96-2-11 (FIG. 6A).

Example 6

This Example describes the construction of plasmids DS-2242-1 and DS-2242-2 that express the full-length NTHi strain 33 hia gene in the presence of the *E. coli* cer gene.

Chromosomal DNA was purified from NTHi strain 33 and PCR amplification was performed using oligonucleotides 5039.SL and 5040.SL (FIG. 17). The sense primer (5040.SL) was designed based upon the 5'-flanking sequence of strain 11 hia and the conserved amino terminal sequences of the NTHi Hia and Hib Hsf proteins. The antisense primer (5039.SL) was the same as that described in Example 1 and was based upon the conserved carboxy terminal sequences of the Hia and Hsf proteins. The 3 kb strain 33 hia PCR fragment was cloned into pCR II, generating plasmid DS-1917-3-8.

In order to express the full-length strain 33 hia gene, approximately 106 by of the 5'-end of the gene was synthesized from oligonucleotides, from the start codon to an AlwN I site (FIG. 7B). Plasmid DS-1917-3-8 was digested with AlwN I and BamH I and the approximately 2.9 kb fragment containing the hia gene was purified. Plasmid pT7-7 was digested with Nde I and BamH I. The Nde 1-AlwN I oligonucleotides and AlwN I-amH I hia fragment were ligated into the pT7-7 vector, generating plasmid DS-2103-4.

In order to include the *E. coli* cer gene and utilize kanamycin selection, the Bgl II-BamH I fragment containing the T7 hia (33) gene cassette was excised from DS-2103-4 and cloned into BK-2-1-1 that had been digested with Bgl II and dephosphorylated. Plasmids DS-2242-1 and DS-2242-2 contain single copies of the T7 hia (33) gene cassette in opposite orientations, the *E. coli* cer gene, and the kanamycin resistance gene (FIG. 7A).

Example 7

This Example describes the construction of plasmid DS-2340-2-3 that contains a T7 hia gene cassette with a truncated V38 strain 33 hia gene, the *E. coli* cer gene, and the kanamycin resistance gene.

PCR primers were designed to amplify a 250 by fragment of the 5'-end of the NTHi strain 33 hia gene from a V38 start codon up to an internal SnaB I site. An Nde I site was added at the 5'-end for cloning purposes and the fragment was amplified using plasmid DS-2242-1 as template. The construction scheme is shown in FIG. 8A and the PCR primers are shown in FIG. 8B. The fragment was cloned into pCR II generating plasmid DS-2328-1-1. DS-2242-1 was digested with Nde I and SnaB I and the 8.5 kb vector fragment purified. DS-2328-1-1 was digested with Nde I and SnaB I and the 0.25 kb 5' hia fragment was ligated with the 8.5 kb vector fragment from DS-2242-1, to generate plasmid DS-2340-2-3.

Example 8

This Example illustrates the construction of plasmids DS-2447-2 and DS-2448-17 that contain tandem copies of T7 V38 hia (11) or T7 V38 hia (33) gene cassettes, respectively, the *E. coli* cer gene, and a kanamycin resistance gene.

Figure 9A:
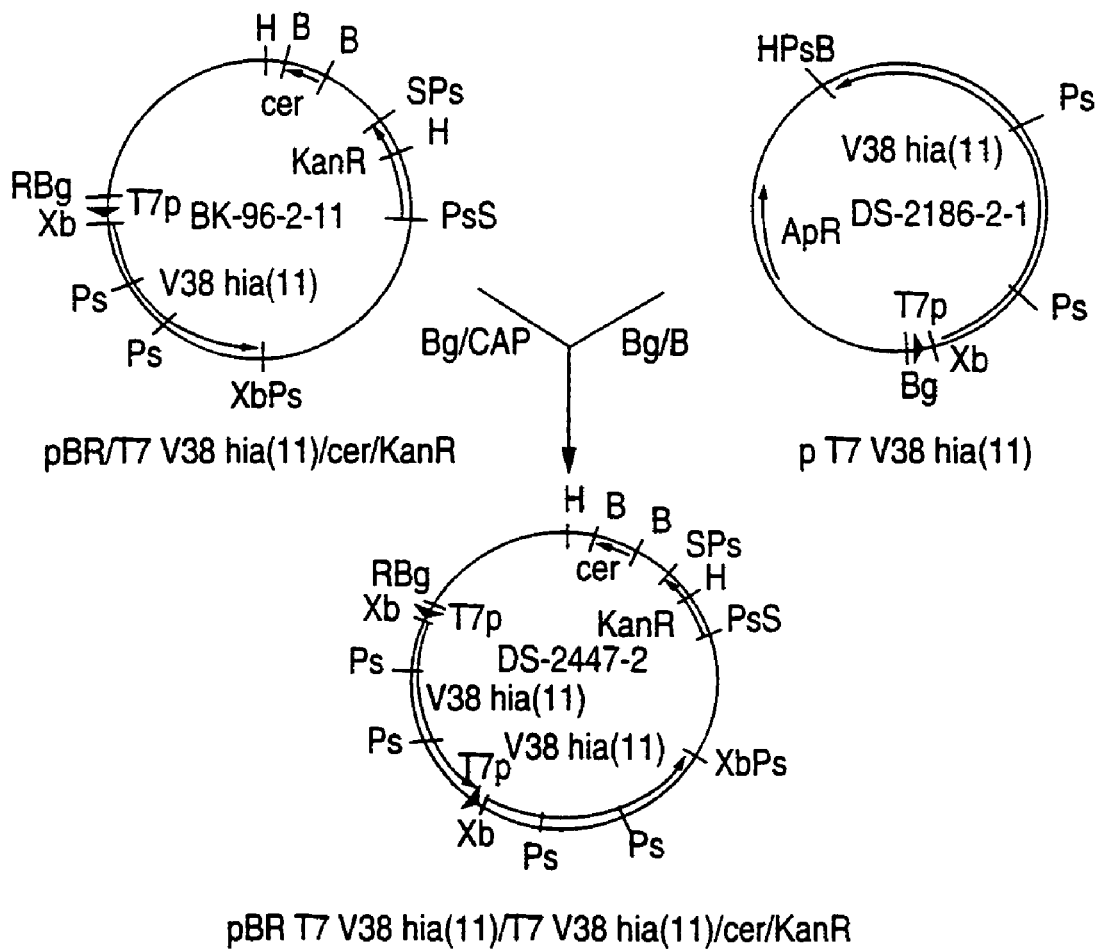
FIGS. 9A and 9B show the construction of plasmids DS-2447-2 and DS-2448-17, that contain tandem copies of the T7 V38 hia (11) and T7 V38 WA (33) genes, respectively.

Plasmid BK-96-2-11, that contains a T7 V38 hia (11) gene cassette, was linearized with Bgl II and dephosphorylated. The Bgl II-BamH I T7 V38 hia (11) gene cassette from DS-2186-2-1 was ligated into BK-96-2-11, generating plasmid DS-2447-2 that contains tandem copies of the T7 V38 hia (11) gene in the same orientation (FIG. 9A).

Figure 9B:
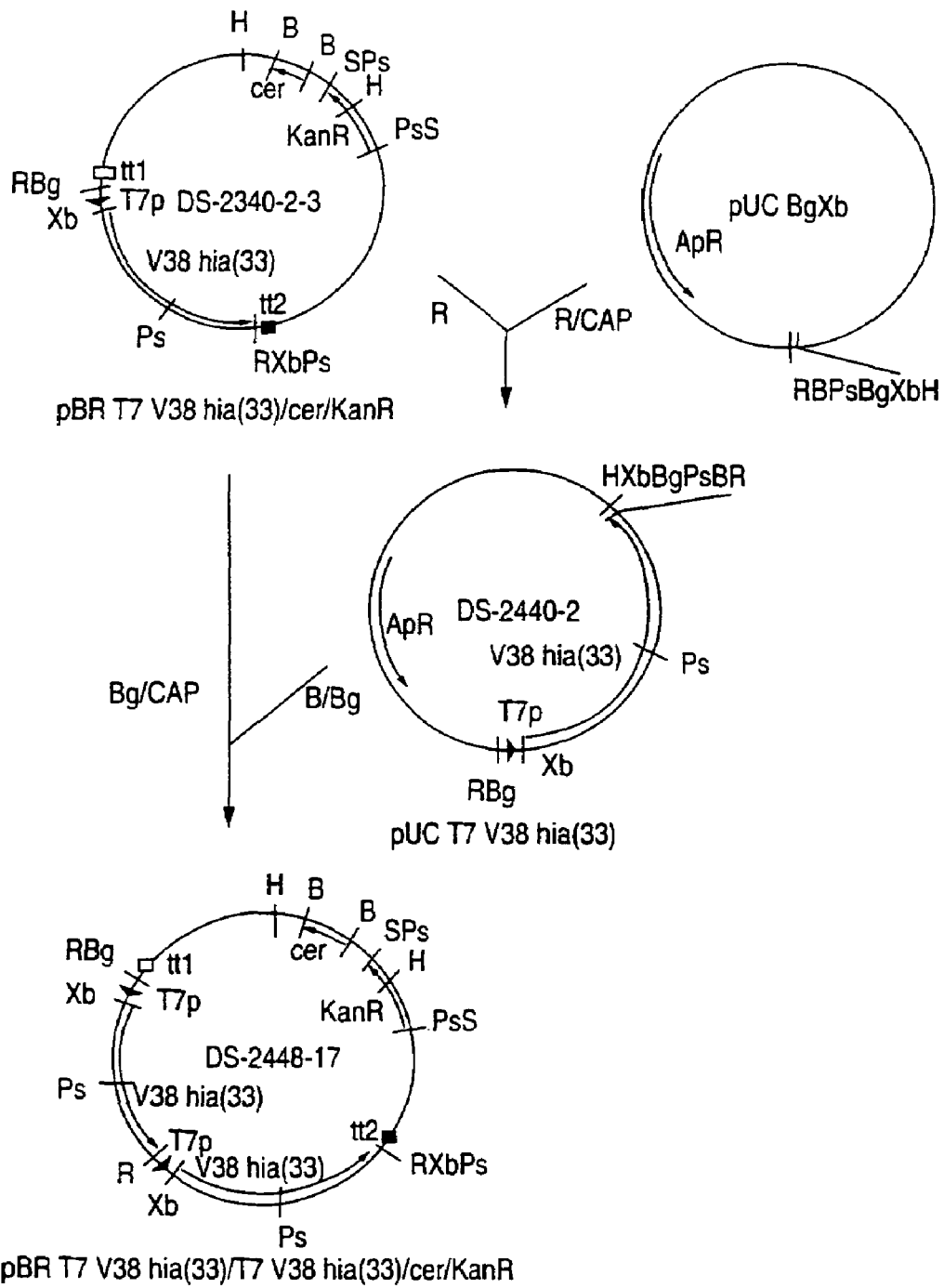

Plasmid DS-2340-2-3 was digested with EcoR I and the T7 V38 hia (33) gene cassette was subcloned into pUC-BgXb that had been digested with EcoR I and dephosphorylated. The resultant plasmid, DS-2440-2 was digested with Bgl II and BamH I to release the T7 V38 hia (33) cassette that was ligated with DS-2340-2-3 that had been linearized with Bgl II and dephosphorylated. Plasmid DS-2448-17 contains tandem T7 V38 hia(33) genes in the same orientation (FIG. 9B).

Example 9

This Example illustrates the expression of full-length and truncated recombinant hia genes.

DNA from expression plasmids prepared as described in the preceding Examples, was introduced into electrocompetent *E. coli* BL21 (DE3) cells using a BioRad electroporator. Cells were grown at 37° C. in NZCYM medium using the appropriate antibiotic selection to $A_{578}$ of 0.3 before the addition of lactose to 1.0% for 4 hours. Samples were adjusted to 0.2 OD/µl with SDS-PAGE lysis+loading buffer and the same amount of each protein sample was loaded onto SDS-PAGE gels (ref. 22). FIG. 10 illustrates the relative production of rHia (11) proteins from various constructs. As seen in panel A, there is an increase in production with decreased size of rHia. V38-(lane 5) and N52-truncated rHia (lane 6) have significantly higher expression levels than their longer counterparts (lanes 2, 3, 4). In addition, panel B demonstrates that the production of V38 rHia is apparently increased in the presence of the cer gene.

Example 10

This Example illustrates the purification of rHia proteins.

All the recombinant Hia proteins were expressed as inclusion bodies in *E. coli* and were purified by the same procedure (FIG. 11). *E. coli* cell pellets from 500 ml culture were resuspended in 50 ml of 50 mM Tris-HCl, pH 8.0, containing 0.1 M NaCl, and disrupted by sonication. The extract was centrifuged at 20,000 g for 30 min and the resultant supernatant was discarded. The pellet ($PPT_1$) was further extracted, in 50 ml of 50 mM Tris-HCl, pH 8.0 containing 0.5% Triton X-100 and 10 mM EDTA, then centrifuged at 20,000 g for 30 min, and the supernatant was discarded. The pellet ($PPT_2$) was further extracted in 50 ml of 50 mM Tris-HCl, pH 8.0, containing 1% octylglucoside, then centrifuged at 20,000 g for 30 min, and the supernatant was discarded.

The resultant pellet ($PPT_3$) obtained after the above extractions contains the inclusion bodies. The pellet was solubilized in 6 ml of 50 mM Tris-HCl, pH 8.0, containing 6 M guanidine and 5 mM DTT. Twelve ml of 50 mM Tris-HCl, pH 8.0 was added to this solution and the mixture was centrifuged at 20,000 g for 30 min. The supernatant ($SUP_4$) was precipitated with polyethylene glycol (PEG) 4000 at a final concentration of 7%. The resultant pellet ($PPT_5$) was removed by centrifugation at 20,000 g for 30 min and the supernatant was precipitated by $(NH_4)_2SO_4$ at 50% saturation. The $(NH_4)_2SO_4$ precipitate was collected by centrifugation at 20,000 g for 30 min. The resultant pellet ($PPT_6$) was dissolved in 2 ml of 50 mM Tris-HCl, pH 8.0, containing 6 M guanidine HCl and 5 mM DTT and the clear solution was purified on a Superdex 200 gel filtration column equilibrated in 50 mM Tris-HCl, pH 8.0, containing 2 M guanidine HCl. The fractions were analysed by SDS-PAGE and those containing the purified rHia were pooled and dialysed overnight at 4° C. against PBS, then centrifuged at 20,000 g for 30 min. The protein remained soluble under these conditions and glycerol was added to the rHia preparation at a final concentration of 20% for storage at −20° C. SDS-PAGE analysis of purified V38 rHia (11) and V38 rHia (33) is illustrated in FIG. 12. The average yield of the purified V38 rHia proteins is about 10 mg $l^{-1}$ culture.

In order to study the stability of rHia, the purified V38 rHia (11) protein was stored at 4° C. with or without glycerol and at −20° C. with glycerol. The protein was found to be stable under all three conditions and remained intact for at least eight weeks with repeated freezing and thawing (FIG. 13).

Example 11

This Example illustrates the immunogenicity of V38 rHia (11) and V38 rHia (33) proteins.

Hyperimmune antisera against rHia proteins were produced by immunizing two guinea pigs (Charles River) intramuscularly (i.m.) with 5 µg doses of antigen emulsified in complete Freund's adjuvant (CFA, Difco) on day 1. Animals were boosted on days 14 and 28 with 5 µg doses of protein in incomplete Freund's adjuvant (IFA) and sera were collected on day 42. Anti-Hib strain MinnA and anti-*Haemophilus* type a strain ATCC 9006 antisera were generated using the same protocol, except that a heat-inactivated bacterial preparation was used as the immunogen ($1 \times 10^8$ cfu per dose).

To study the immunogenicity of the V38 rHia proteins, groups of five CD-1 mice (Charles River, Quebec) were immunized s.c. on days 1 and 28 with 0.3, 1, 3, and 10 µg of antigen, in the presence of $AlPO_4$ (alum) (1.5 mg per dose). Blood samples were collected on days 1, 28 and 42. Mice generated significant anti-V38 rHia antibody responses even with a single injection of 0.3 µg antigen (FIG. 14, panel A), suggesting that both proteins had retained immunogenicity after inclusion body extraction and solubilization. No statistically significant difference was found in the antibody titers induced by the V38 rHia proteins derived from strains 11 or 33.

To study the immunogenicity of the V38 rHia (11) protein in BALB/c mice, groups of five animals (Charles River, Quebec) were immunized s.c. on days 1, 28 and 42 with 0.3, 1, 3, and 10 µg of antigen, in the presence of $AlPO_4$ (1.5 mg per dose). Blood samples were collected on days 1, 14, 28, 42 and 56. High antibody titers were observed in all groups, indicating that the protein is very immunogenic even at 0.3 µg per dose (FIG. 15, panel A).

To study the immunogenicity of the V38 rHia (11) protein in guinea pigs, groups of five animals (Charles River, Quebec) were immunized s.c. on days 1, 28 and 42 with 0.3, 1, 3, and 10 µg of antigen, in the presence of $AlPO_4$ (1.5 mg per dose). Blood samples were collected on days 1, 14, 28, 42 and 56. High antibody titers were observed in all groups, indicating that the protein is also very immunogenic in guinea pigs (FIG. 15, panel B).

Example 12

This Example illustrates the analysis of the protection afforded by anti-rHia antibodies in passive infant rat models of bacteremia.

Pregnant Wistar rats were purchased from Charles River. In the *H. influenzae* type b bacteremia model, groups of 6 to 10 five-day old infant rats were injected s.c. in the dorsal region with 0.1 ml of guinea pig anti-rHia or anti-strain MinnA antiserum. The control animals received injections with pre-immune sera only. Twenty hours later, the animals were challenged intraperitoneally (i.p.) with 200 to 240 colony-forming units (cfu) of freshly grown Hib strain MinnA (0.1 ml). Blood samples were collected 20 h post-challenge, via cardiac puncture under isoflurane anesthesia and plated on chocolate agar plates. Colonies were counted after one day and the results were statistically analyzed by Fisher's Exact test.

In the *H. influenzae* type a bacteremia model (ref. 23), groups of 9 to 10 five-day old infant rats were injected s.c. in the dorsal region with 0.1 ml of guinea pig anti-rHia or anti-strain ATCC 9006 antiserum. The animals in the control group were injected with guinea pig pre-immune serum. Twenty hours later, the animals were challenged i.p. with 100,000 cfu of freshly grown *H. influenzae* type a strain ATCC 9006 (0.1 ml). Blood samples were collected 20 h post-challenge and analysed as described above.

As shown in Tables 1 and 2 below, the infant rats that were passively immunized with either guinea pig anti-rHia (11) or anti-V38 rHia (11) antisera, were all significantly protected against type a or type b *H. influenzae* caused bacteremia. These results demonstrate that antibodies raised to the slightly truncated Hia protein (V38 rHia) are as efficacious as those raised to the full-length protein at protecting animals against bacteremia caused by type a or type b *H. influenzae*. Such protection afforded by an NTHi-derived recombinant protein against invasive disease caused by encapsulated bacteria, illustrates the utility of the rHia proteins as vaccine antigens.

Example 13

This Example illustrates the protection afforded by immunization with V38 rHia protein in a chinchilla model of nasopharyngeal colonization.

A nasopharyngeal colonization model has been described by Yang et al (ref. 20). The model works well for those NTHi strains that produce the HMW adhesins, but reproducible colonization could not be established with Hia-producing strains under the same conditions. Repeated attempts to colonize with the prototype Hia-producing NTHi strain 11, were unsuccessful. Colonization was achieved with NTHi strain 33 at $5 \times 10^8$ cfu per inoculum, compared with only $10^8$ cfu required for the prototype HMW-producing NTHi strain 12. Under these conditions, partial protection was observed in animals immunized with 100 μg of V38 rHia (33) and challenged with the homologous NTHi strain 33.

Example 14

This Example illustrates the cloning and sequence analysis of additional hia genes from *H. influenzae* strains.

Oligonucleotides (5040.SL and 5039.SL) for PCR amplification were designed based upon the conserved promoter, N-terminal and C-terminal sequences of the hia and hsf genes and proteins (FIG. 17). The strains chosen for PCR amplification were chosen based upon their reactivity with anti-rHia (11) antisera.

Chromosomal DNA was prepared from NTHi strains 12, 29, 32, M4071, K9 and, K22 and *Haemophilus* type c strain API. PCR amplification was performed as follows: each reaction mixture contained 5 to 100 ng of DNA, 1 lag of each primer, 5 units of taq+ or tsg+(Sangon) or taq plus long (Stratagene), 2 mM dNTPs, 20 mM Tris-HCl (pH 8.8), 10 mM KCl, 10 mM $(NH_4)_2SO_4$, 2 mM $MgSO_4$, 0.1% Triton X-100, BSA. Cycling conditions were: 95° C. for 1 min, followed by 25 cycles of 95° C. for 30 sec, 45° C. for 1 min, 72° C. for 2 min; then 72° C. for 10 min.

The nucleotide and deduced amino acid sequences of the hia gene from strain 33 are shown in FIG. 18. The predicted Hia protein from strain 33 has a molecular weight of 103.6 kDa and a pI of 9.47. The nucleotide and deduced amino acid sequences of the hia gene from strain 32 are shown in FIG. 19. The predicted Hia protein from strain 32 has a molecular weight of 70.4 kDa and a pI of 5.67. There is a KDEL sequence present between residues 493 and 496. Such sequences have been associated with anchoring proteins to the endoplasmic reticulum. The deduced strain 32 Hia protein is significantly smaller and has a significantly different pI, however it does contain many of the motifs present in other Hia molecules.

The nucleotide and deduced amino acid sequences of the hia gene from strain 29 are shown in FIG. 20. The predicted Hia protein from strain 29 has a molecular weight of 114.4 kDa and a pI of 7.58. The nucleotide and deduced amino acid sequences of the hia gene from strain K22 are shown in FIG. 23. The predicted Hia protein from strain K22 has a molecular weight of 114.4 kDa and a pI of 7.58. The deduced Hia sequences from NTHi strains 29 and K22 were found to be identical. Strain 29 was isolated from a 7-month old child with otitis media in Cleveland, Ohio, while strain K22 was isolated from an aborigine near Kimberly, Australia.

The nucleotide and deduced amino acid sequences of the hia gene from strain 4071 are shown in FIG. 21. The predicted Hia protein from strain M4071 has a molecular weight of 103.4 kDa and a pI of 9.49. There is a KDEL sequence present between residues 534 and 537.

The nucleotide and deduced amino acid sequences of the hia gene from strain K9 are shown in FIG. 22. The predicted Hia protein from K9 has a molecular weight of 113.8 kDa and a pI of 6.45.

The nucleotide and deduced amino acid sequences of the hia gene from strain type c *Haemophilus* API are shown in FIG. 24. The predicted Hia protein from API has a molecular weight of 249.4 kDa and a pI of 5.34. The deduced Hia/Hsf sequence from the type c strain API is nearly identical to the published type b Hsf sequence except for a 60 residue insert. Since the NTHi-based Hia protein provided herein protects in passive models of type a and type b infection, it is likely that it will also protect against type c disease due to sequence similarity between the type b and type c proteins.

The nucleotide and deduced amino acid sequences of the hia locus from strain 12 are shown in FIG. 25. NTHi strain 12 does not produce Hia. However, part of the hia gene can be PCR amplified, there is inconsistent positive reactivity of SB12 cell lysates with anti-rHia antibody, and there is reactivity with a DNA probe derived from the 3'-end of the strain 11 hia gene, on Southern blots. Analysis of the PCR amplified DNA, revealed a 1.8 kb fragment that contains 1 kb of the 3'-end of the upstream HI1732-related gene and 0.8 kb of the 3'-end of the hia gene.

PCR amplification using primers that would amplify across the putative junction of these two genes in strain 12, confirmed the genetic composition of the locus. Thus it would appear that strain 12 does not produce Hia because it has suffered a deletion of the 5'-end of the hia gene. FIG. 27 shows a sequence comparison between the upstream orf of strain 12 and the Rd genome deduced HI1733 protein. Over the region of homology, the two proteins are 95% identical.

An alignment of the deduced Hia sequences from NTHi strains 33, 32, 29, K22, M4071, 11 and K9 and type c strain API compared with *H. influenzae* type b Hsf, the aidA-like (Hsf/Hia) HI1732 gene from the Rd genome, and the *M. catarrhalis* 200 kDa protein from strains 4223 and LES-1 is shown in FIG. 28. There is a frame shift in the Rd genome sequence resulting in premature truncation of the HI1732 protein. Additional downstream sequence related to hia, is included here. The asterisks below the sequence indicate conserved residues. The N-terminal (approximately 50 residues) and C-terminal sequences (approximately 150 residues) are highly conserved amongst the *Haemophilus* strains, while some similarity is evident with the *M. catarrhalis* counterpart. Sequence analysis reveals that there are two potential gene families of Hia proteins, one related to the prototype strain 11 and the other more closely related to strain 33. The strains 11 and K9 proteins appear to be more like the Hsf proteins from the type b, type c or type d *Haemophilus* strains while the strains 33, 32, 29, K22 and M4071 proteins appear to form a second family.

Example 15

This Example describes the construction of plasmid JB-2930-3 that contains a T7 hia gene cassette with a truncated S44 strain 11 hia gene, the *E. coli* cer gene, and the kanamycin antibiotic resistance gene, and expression of S44 Hia proteins.

PCR primers were designed to amplify the S44 Hia N-terminus of the NTHi strain 11 hia gene from the S44 amino acid to an internal Sty I site (FIG. 29). An Nde I site was added at the 5'-end for cloning purposes and the fragment was amplified using plasmid DS-2242-1 as a template. The fragment was cloned into pCR II generating plasmid JB-2910-1-1. The construction scheme is shown in FIG. 30. Plasmid JB-2910-1-1 was digested with Nde I and Sty I and the 5' PCR hia fragment isolated. Plasmid IA-46-5 containing the V38 hia gene was digested with Nde I and Sty I and the larger approximately 8.5 kb fragment purified. The two purified fragments were ligated together to produce plasmid JB-2917-1. This plasmid was then digested with Nde I and treated with calf intestinal phosphatase (CAP), and into it was cloned the T7 promoter from plasmid IA-46-5. The promoter was cut out using Nde I digestion of IA-46-5. The resulting plasmid, JB-2925-3, was digested with Bgl II and Bam HI and the hia gene was isolated. This fragment was ligated into the Bgl II/CAP-treated plasmid BK-2-1-2 to produce plasmid JB-2930-3. This plasmid contains the T7 promoter S44 hia gene and *E. coli* cer gene and kanamycin resistance.

The recombinant S44 hia vector was transformed into *E. coli* BL21(DE3) for expression studies. The procedure for expression in *E. coli* was as described in Example 9. FIG. 31 SDS-PAGE analysis of shows the expression of recombinant S44 hia from two different vectors, JB-2930-3 (described above) and pET vector IA-191-3-1. Plasmid TA-191-3-1 is identical to JB-2930-3 except it is a pET vector containing the lacI$^g$ repressor and, therefore, the amount of S44 Hia produced is less than the T7 S44 from JB-2930-3. The plasmid is shown, along with plasmid JB-2930-3, FIG. 32. FIG. 31 shows the S44 Hia as a doublet band (lane 3) at approximately 116 kDa. Upon further analysis using purified S44 hia from JB-2930-3, the lower band of the doublet was found to have a C-terminal truncation of 94 amino acids, while retaining the expected N-terminus. The purification process used for isolation of the truncated Hia was as described in Example 10.

SUMMARY OF THE DISCLOSURE

In summary of this disclosure, the present invention provides novel isolated and purified nucleic acid molecules encoding full-length and N-terminal truncated *Haemophilus influenzae* adhesin (Hia) proteins from *Haemophilus* which enable protective Hia proteins to be produced recombinantly. Modifications are possible within the scope of this invention.

REFERENCES

1. Barbour, M. L., R. T. Mayon-White, C. Coles, D. W. M. Crook, and E. R. Moxon. 1995. The impact of conjugate vaccine on carriage of *Haemophilus influenzae* type b. J. Infect. Dis. 171:93-98.
2. Berkowitz et al. 1987. J. Pediatr. 110:509.
3. Claesson et al. 1989. J. Pediatr. 114:97.
4. Black, S. B., H. R. Shinefield, B. Fireman, R. Hiatt, M. Polen, E. Vittinghoff, The Northern California Kaiser Permanent Vaccine Study Center Pediatrics Group. Efficacy in infancy of oligosaccharide conjugate *Haemophilus influenzae* type b (HbOC) vaccine in a United States population of 61,080 children. 1991. Pediatr. Infect. Dis. J. 10:97-104.
5. Nitta, D. M., M. A. Jackson, V. F. Burry, and L. C. Olson. 1995. Invasive *Haemophilus influenzae* type f disease. Pediatr. Infect. Dis. J. 14:157-160.
6. Waggoner-Fountain, L. A., J. O. Hendley, E. J. Cody, V. A. Perriello, and L. G. Donowitz. 1995. The emergence of *Haemophilus influenzae* types e and f as significant pathogens. Clin. Infect. Dis. 21:1322-1324.
7. Madore, D. V. 1996. Impact of immunization on *Haemophilus influenzae* type b disease. Infectious Agents and Disease 5:8-20.
8. Bluestone, C. D. 1982. Current concepts in otolaryngology. Otitis media in children: to treat or not to treat? N. Engl. J. Med. 306:1399-1404.
9. Barenkamp, S. J., and E. Leininger. 1992. Cloning, expression, and DNA sequence analysis of genes encoding nontypeable *Haemophilus influenzae* high-molecular-weight surface-exposed proteins related to filamentous hemagglutinin of *Bordetella pertussis*. Infect. Immun. 60:1302-1313.
10. St. Geme III, J. W., S. Falkow, and S. J. Barenkamp. 1993. High-molecular-weight proteins of nontypeable *Haemophilus influenzae* mediate attachment to human epithelial cells. Proc. Natl. Acad. Sci. USA 90:2875-2879.
11. Barenkamp, S. J. 1996. Immunization with high-molecular-weight adhesion proteins of nontypeable *Haemophilus influenzae* modifies experimental otitis media in chinchillas. Infect. Immun. 64:1246-1251.
12. St. Geme, J. W. and D. Cutter. 1995. Evidence that surface fibrils expressed by *Haemophilus influenzae* type b promote attachment to human epithelial cells. Molec. Microbiol. 15:77-85.
13. Barenkamp, S. J. and J. W. St. Geme. 1996. Identification of a second family of high-molecular-weight adhesion proteins expressed by non-typable *Haemophilus influenzae*. Molec. Microbiol. 19:1215-1223.
14. St. Geme, J. W., D. Cutter, and S. J. Barenkamp. 1996. Characterization of the genetic locus encoding *Haemophilus influenzae* type b surface fibrils. J. Bact. 178:6281-6287.
15. Patient, M. E., and D. K. Summers. 1993. ColE1 multimer formation triggers inhibition of *Escherichia coli* cell division. Molec. Microbiol. 9:1089-1095.
16. O'Hagan, D T. 1992. Oral delivery of vaccines. Formulation and clinical pharmaco kinetic considerations. Clin. Pharmacokinet 22(t): 1-10.
17. Ulmer et al. 1993. Curr. Opinion Invest. Drugs 2:983-989.
18. Lockhoff, O., 1991. Glycolipids as immunomodulators: Synthesis and properties.
19. Nixon-George A., et al., 1990. The adjuvant effect of stearyl tyrosine on a recombinant subunit hepatitis B surface antigen. J. Immunol. 144 (12):4798-4802.
20. Yang, Y-P., S. M. Loosmore, B. J. Underdown, and M. H. Klein. 1998. Nasopharyngeal colonization with nontypeable *Haemophilus influenzae* in chinchillas. Infect. Immun. 66:1973-1980.
21. Tabor, S., and C. C. Richardson. 1985. A bacteriophage T7 RNA polymerase/promoter system for controlled exclusive expression of specific genes. Proc. Natl. Acad. Sci. USA 82:1074-1078.
22. Laemmli, U. K. 1970. Cleavage of structural proteins during the assembly of the head of bacteriophage T4. Nature 227:680-685.
23. Loosmore, S. M., Y—P. Yang, D. C. Coleman, J. M. Shortreed, D. M. England, and M. H. Klein. 1997. Outer membrane protein D15 is conserved among *Haemophilus influenzae* species and may represent a universal protective antigen against invasive disease. Infect. Immun. 65:3701-3707.
24. Needleman, S. B. and Wunsch, C. D. 1970, J. Mol. Biol. 48:443-453.
25. Sellers, P. H. 1974 On the theory and computation of evolutionary distances. J. Appl. Math(Siam) 26:787-793.
26. Waterman, M. S., Smith, T. F. and Beyer, W. A. 1976. Advan. Math. 20:367-387.
27. Smith, T. F. and Waterman, M. S. 1981 Identification of common molecular subsequences. J. Mol. Biol. 147:195-197.
28. Sobel, E. and Martinez, H. M. 1985 A multiple Sequence Alignment Program. Nucleic Acid Res. 14:363-374.

TABLE 1

Protective effect of guinea pig anti-rHia (full-length) antiserum against type a or b *H. influenzae* in the infant rat model of bacteremia

| Group (#) | Guinea pig serum | Anti-rHia antibody titers | No. bacteremic/ No. challenged | Mean cfu/ 100 µl blood |
|---|---|---|---|---|
| 1 | Anti-type a | nd | 0/10* | 0** |
| 2 | Anti-rHia | 204,800 | 1/10* | 0** |
| 3 | Preimmune | <100 | 7/10 | 88 |

TABLE 1-continued

Protective effect of guinea pig anti-rHia (full-length)
antiserum against type a or b H. influenzae in the
infant rat model of bacteremia

| Group (#) | Guinea pig serum | Anti-rHia antibody titers | No. bacteremic/ No. challenged | Mean cfu/ 2.5 µl blood |
|---|---|---|---|---|
| 4 | Anti-MinnA | nd | 0/10* | 0** |
| 5 | Anti-rHia | 204,800 | 1/10* | 2** |
| 6 | Preimmune | <100 | 10/10 | 600 |

Five-day old infant rats were passively immunized s.c. with 0.1 ml of indicated guinea pig antiserum or preimmune serum. Twenty hours later, infant rats were challenged i.p. with either freshly grown H. influenzae type a strain ATCC 9006 ($10^5$ cfu, 0.1 ml) for groups #1 to 3; or with freshly grown Hib strain MinnA (240 cfu, 0.1 ml) for groups #4 to 6. Infected animals are defined as >20 cfu recovered from 100 µl of blood for groups #1 to 3; or >30 cfu recovered from 2.5 µl of blood for groups #4 to 6.
*Fisher exact test. Statistical significance compared to animals in group 3 or 6 was found (P < 0.05).
**Student's unpaired t test. Statistical significance compared to animals in group 3 or 6 was found (P < 0.05).
nd: not determined.

TABLE 2

Protective effect of guinea pig anti-V38 rHia (SB11)
antiserum against type a or b H. influenzae in the
infant rat model of bacteremia

| Group (#) | Guinea pig serum | Anti-rHia antibody titers | No. bacteremic/ No. challenged | Mean cfu/ 20 µl blood |
|---|---|---|---|---|
| 1 | Anti-type a | nd | 0/6* | 0** |
| 2 | Anti-rHia | 204,800 | 1/9* | 5** |
| 3 | Preimmune | <100 | 5/8 | 165 |
|   |   |   |   | Mean cfu/ 2 µl blood |
| 4 | Anti-MinnA | nd | 0/6* | 0** |
| 5 | Anti-rHia | 204,800 | 1/9* | 2** |
| 6 | Preimmune | <100 | 10/10 | 820 |

Five-day old infant rats were passively immunized s.c. with 0.1 ml of indicated guinea pig antiserum or preimmune serum. Twenty hours later, infant rats were challenged i.p. with either freshly grown H. influenzae type a strain ATCC 9006 ($10^5$ cfu, 0.1 ml) for groups #1 to 3; or with freshly grown Hib strain MinnA (190 cfu, 0.1 ml) for groups #4 to 6. Infected animals is defined as >20 cfu recovered from 20 µl of blood for groups #1 to 3; or >30 cfu recovered from 2 µl of blood for groups #4 to 6.
*Fisher exact test. Statistical significance compared to animals in group 3 or 6 was found (P < 0.05)
**Student's unpaired t test. Statistical significance compared to animals in group 3 or 6 was found (P < 0.05).
nd: Not determined.

The invention claimed is:

1. An immunogenic composition comprising a recombinant *Haemophilus influenzae* adhesion (Hia) protein of non-typeable strain 33 encoded by SEQ ID.: 23, and a pharmaceutically acceptable carrier therefor.

2. The immunogenic composition of claim 1 formulated as a vaccine for in vivo administration such that, upon administration of the composition to a host, the host is protected against disease caused by *Haemophilus influenzae* non-typeable strain 33.

3. The immunogenic composition of claim 1 formulated as a microparticle, capsule or liposome preparation.

4. The immunogenic composition of claim 1 further comprising an adjuvant.

5. A method for inducing protection against disease caused by *Haemophilia influenzae* non-typeable strain 33, comprising administering to a susceptible host an effective amount of the immunogenic composition of claim 1.

6. The method of claim 5 wherein the susceptible host is a human.

7. An immunogenic composition comprising a recombinant *Haemophilia influenzae* adhesion (Hia) protein of non-typeable strain 33 having the amino acid sequence of SEQ ID NO: 24, and a pharmaceutically acceptable carrier therefor.

8. The immunogenic composition of claim 7 formulated as a vaccine for in vivo administration such that, upon administration of the composition to a host, the host is protected against disease caused by *Haemophilus influenzae* non-typeable strain 33.

9. The immunogenic composition of claim 7 formulated as a microparticle, capsule or liposome preparation.

10. The immunogenic composition of claim 7 further comprising an adjuvant.

11. A method for inducing protection against disease caused by *Haemophilus influenzae* non-typeable strain 33, comprising administering to a susceptible host an effective amount of the immunogenic composition of claim 7.

12. The method of claim 11 wherein the susceptible host is a human.

13. An immunogenic composition comprising a truncated recombinant *Haemophilia influenzae* adhesion (Hia) protein of non-typeable strain 33 having the amino acid sequence of SEQ. ID NO.: 24, beginning at valine 38.

14. The immunogenic composition of claim 13 formulated as a vaccine for in vivo administration such that, upon administration of the composition to a host, the host is protected against disease caused by *Haemophilus influenzae* non-typeable strain 33.

15. The immunogenic composition of claim 13 formulated as a microparticle, capsule or liposome preparation.

16. The immunogenic composition of claim 13 further comprising an adjuvant.

17. A method for inducing, protection against disease caused by *Haemophilus influenzae* non-typeable strain 33, comprising administering to a susceptible host an effective amount of the immunogenic composition of claim 13.

18. The method of claim 17 wherein the susceptible host is a human.

* * * * *